US010646452B2

(12) United States Patent
Dave et al.

(10) Patent No.: US 10,646,452 B2
(45) Date of Patent: May 12, 2020

(54) SYSTEM AND METHOD FOR FABRICATION OF UNIFORM POLYMER FILMS CONTAINING NANO AND MICRO PARTICLES VIA CONTINUOUS DRYING PROCESS

(71) Applicant: New Jersey Institute of Technology, Newark, NJ (US)

(72) Inventors: Rajesh N. Dave, Princeton, NJ (US); Ramani Susarla, Broad View Heights, OH (US); Boris Khusid, New Providence, NJ (US); Anagha A. Bhakay, Philadelphia, PA (US); Ecevit A. Bilgili, Woodbridge, NJ (US); Fernando Muzzio, Pennington, NJ (US)

(73) Assignees: New Jersey Institute of Technology, Newark, NJ (US); Rutgers, The State University of New Jersey, New Brunswick, NJ (US)

( * ) Notice: Subject to any disclaimer, the term of this patent is extended or adjusted under 35 U.S.C. 154(b) by 584 days.

(21) Appl. No.: 14/777,191

(22) PCT Filed: Mar. 17, 2014

(86) PCT No.: PCT/US2014/030506
§ 371 (c)(1),
(2) Date: Sep. 15, 2015

(87) PCT Pub. No.: WO2014/145699
PCT Pub. Date: Sep. 18, 2014

(65) Prior Publication Data
US 2016/0022599 A1    Jan. 28, 2016

Related U.S. Application Data

(60) Provisional application No. 61/791,752, filed on Mar. 15, 2013.

(51) Int. Cl.
*B29C 39/14* (2006.01)
*A61K 9/70* (2006.01)
(Continued)

(52) U.S. Cl.
CPC ............ *A61K 9/7007* (2013.01); *A61K 9/006* (2013.01); *A61K 9/0056* (2013.01);
(Continued)

(58) Field of Classification Search
CPC .... A61K 8/0208; A61K 8/731; A61K 9/0056; A61K 9/006; A61K 9/7007; A61Q 11/00
(Continued)

(56) References Cited

U.S. PATENT DOCUMENTS

| 4,136,145 A | 7/1979 | Fuchs et al. |
| 4,849,246 A | 7/1989 | Schmidt |
(Continued)

FOREIGN PATENT DOCUMENTS

| WO | 2011/131943 | 10/2011 |
| WO | 2012/042224 | 4/2012 |

OTHER PUBLICATIONS

Jerez-Rozo et al., Complementary Near-Infrared and Raman Chemical Imaging of Pharmaceutical Thin Films, Journal of Pharmaceutical Sciences, Pharmaceutical Technology, vol. 100, No. 11, Nov. 2011.
(Continued)

*Primary Examiner* — Christina A Johnson
*Assistant Examiner* — Xue H Liu
(74) *Attorney, Agent, or Firm* — McCarter & English, LLP

(57) ABSTRACT

The present disclosure provides improved stripfilm based pharmaceutical products (e.g., for enhancing dissolution and bioavailability). More particularly, the present disclosure provides improved systems/methods for fabricating stripfilm
(Continued)

US 10,646,452 B2

Page 2 based pharmaceutical products by utilizing higher viscosity film forming precursors and drying methods that accomplish improved/faster drying and provide improved/excellent content uniformity of active pharmaceutical agents in the strip-film based pharmaceutical products. Exemplary systems/methods advantageously use high viscosity, bio-compatible polymeric precursors, (optional use of surface modified drug powders), and convective drying for fabrication of thin films loaded with nano and/or micro sized particles of poorly water-soluble active pharmaceutical ingredients (APIs) to achieve improved active content uniformity and very fast dissolution from poorly water soluble actives, while accomplishing fast drying during the fabrication process. The present disclosure provides for the fast drying (e.g., via low temperature forced convection) of biocompatible polymer films loaded with poorly water-soluble drug nano-particles.

33 Claims, 40 Drawing Sheets

(51) Int. Cl.
  *A61K 9/00* (2006.01)
  *A61K 31/216* (2006.01)
  *A61K 31/343* (2006.01)
  *A61K 47/32* (2006.01)
  *A61K 47/38* (2006.01)
  *B29C 39/00* (2006.01)
  *A61F 13/00* (2006.01)
  *B29L 7/00* (2006.01)

(52) U.S. Cl.
  CPC .......... *A61K 31/216* (2013.01); *A61K 31/343* (2013.01); *A61K 47/32* (2013.01); *A61K 47/38* (2013.01); *B29C 39/003* (2013.01); *B29C 39/14* (2013.01); *A61F 13/00063* (2013.01); *B29L 2007/008* (2013.01)

(58) Field of Classification Search
  USPC .......... 424/49, 400, 435, 439, 443; 514/781
  See application file for complete search history.

(56) References Cited

U.S. PATENT DOCUMENTS

| | | |
|---|---|---|
| 5,589,195 A | 12/1996 | Potter |
| 5,629,003 A | 5/1997 | Horstmann et al. |
| 5,948,430 A | 9/1999 | Zerbe et al. |
| 6,046,277 A | 4/2000 | Kolter et al. |
| 6,368,625 B1 | 4/2002 | Siebert et al. |
| 6,419,903 B1 | 7/2002 | Xu et al. |
| 6,596,298 B2 | 7/2003 | Leung et al. |
| 7,182,955 B2 | 2/2007 | Hart et al. |
| 7,241,411 B2 | 7/2007 | Berry et al. |
| 7,276,249 B2 | 10/2007 | Ryde et al. |
| 7,648,712 B2 | 1/2010 | Bess et al. |
| 7,824,588 B2 | 11/2010 | Yang et al. |
| 7,972,618 B2 | 7/2011 | Fuisz et al. |
| 8,252,370 B1 | 8/2012 | Young et al. |
| 8,778,382 B2 | 7/2014 | Howard et al. |
| 2003/0206942 A1 | 11/2003 | Kulkarni et al. |
| 2004/0258896 A1* | 12/2004 | Yang ............. A61K 9/006 428/220 |
| 2007/0053846 A1 | 3/2007 | Dave et al. |
| 2007/0087036 A1 | 4/2007 | Durschlag et al. |
| 2008/0014224 A1 | 1/2008 | Boyd et al. |
| 2008/0220078 A1 | 9/2008 | Vodden Morton et al. |
| 2009/0196907 A1* | 8/2009 | Bunick ............. A61K 9/0056 424/439 |
| 2011/0223153 A1 | 9/2011 | Lu et al. |
| 2011/0305768 A1 | 12/2011 | Mao et al. |
| 2013/0137698 A1 | 5/2013 | Zerbe et al. |
| 2014/0065217 A1 | 3/2014 | Zerbe et al. |

OTHER PUBLICATIONS

PCT International Search Report and Written Opinion, PCT/US2014/030506 dated Aug. 8, 2014.
Di Benedetto, G., Precipitation of Micro/Nanoparticles in Enhanced High Energy Dissipation Mixing Systems, A Dissertation Submitted to the Faculty of New Jersey Institute of Technology, submitted Jan. 2009, available online Jul. 2010.
Meng, X. et al., Simultaneous Synthesis, Stabilization, and Self-Assembly of Microscale Drug Particles in Polymer Films, Journal of Applied Polymer Science, vol. 120, Issue 4, (2011) 2082-2089.
Meng, X. et al., Synthesis and immobilization of micro-scale drug particles in cellulosic films, Colloids and Surfaces B: Biointerfaces 86 (2011) 181-188.
Meng, X., Anti-Solvent Precipitation and Subsequent Film Formation of Hydrophobic Drugs for Drug Delivery, A Dissertation Submitted to the Faculty of New Jersey Institute of Technology, submitted May 2011, available online Apr. 2012.
Susarla, R. et al., Fast drying of biocompatible polymer films loaded with poorly water-soluble drug nano-particles via low temperature forced convection, International Journal of Pharmaceutics 455 (2013) 93-103.
PCT/US2014/030506, filed Mar. 17, 2014, WO 2014/145699 A1.
U.S. Appl. No. 61/791,752, filed Mar. 15, 2013.

\* cited by examiner

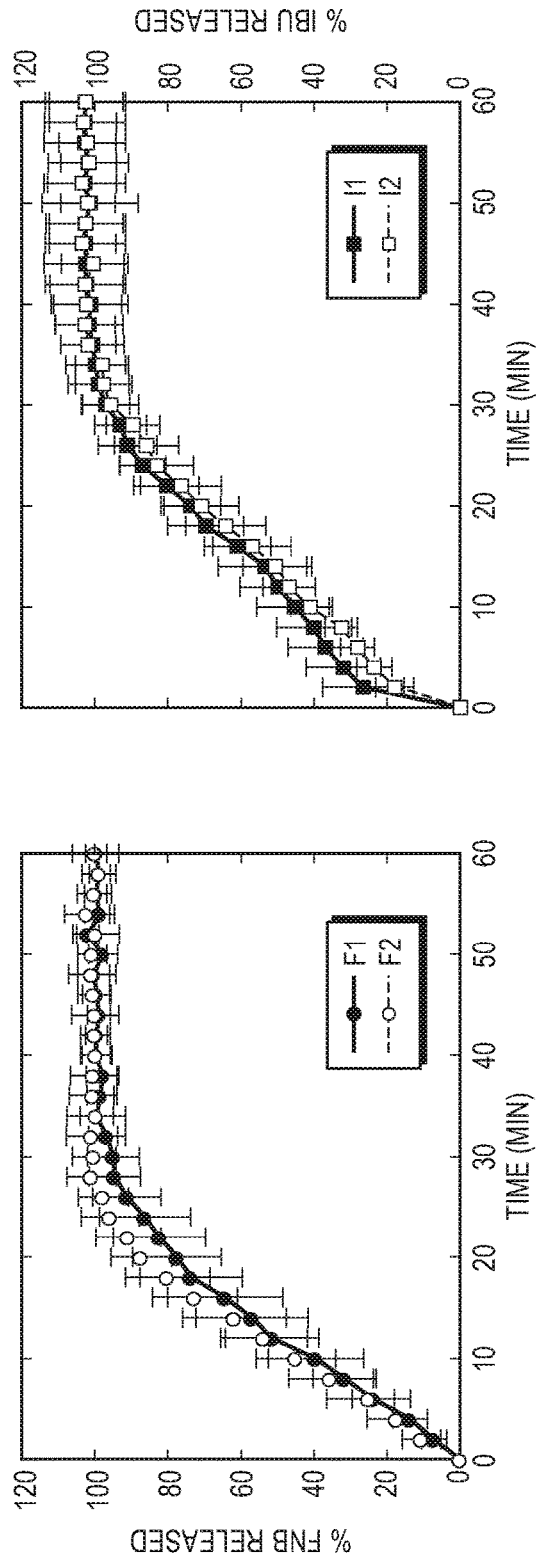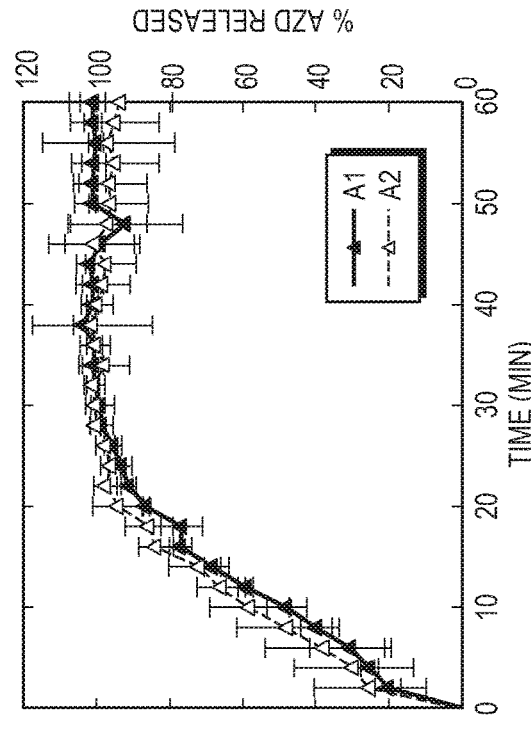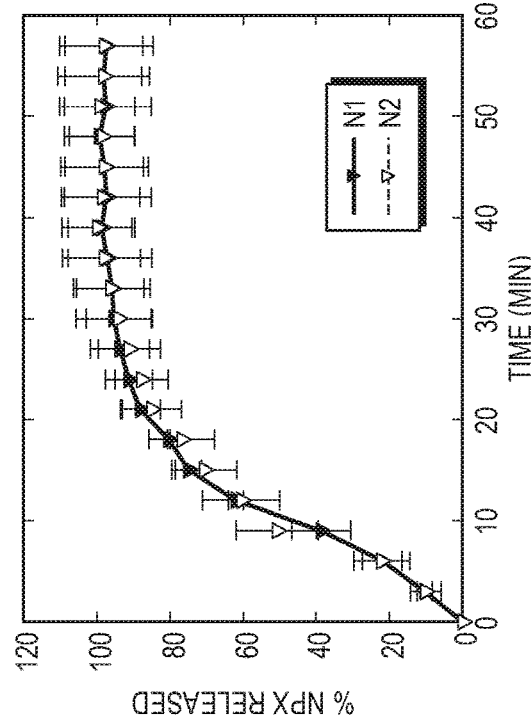
FIG. 25A
FIG. 25B
FIG. 25C
FIG. 25D

SYSTEM AND METHOD FOR FABRICATION OF UNIFORM POLYMER FILMS CONTAINING NANO AND MICRO PARTICLES VIA CONTINUOUS DRYING PROCESS

CROSS-REFERENCE TO RELATED APPLICATIONS

This application claims the benefit of U.S. Provisional Application Ser. No. 61/791,752 filed Mar. 15, 2013, the entire contents of which is herein incorporated by reference in its entirety.

STATEMENT REGARDING FEDERALLY SPONSORED RESEARCH

The research leading to the present disclosure was supported in part by federal grants, including the NSF Grant # EEC-0540855. Accordingly, the United States Government may have certain rights in the disclosure.

FIELD OF THE DISCLOSURE

The present disclosure relates to stripfilm based pharmaceutical products (e.g., for enhancing dissolution and bioavailability) and, more particularly, to improved systems and methods for fabricating stripfilm based pharmaceutical products by utilizing higher viscosity film forming precursors and drying methods that accomplish improved/faster drying and provide improved/excellent content uniformity of active pharmaceutical agents in the stripfilm based pharmaceutical products.

BACKGROUND OF THE DISCLOSURE

In general, there are some routes for attempting to increase bioavailability of poorly water soluble drugs, amongst which formation of nano-composite particles has attracted interest, and nano-milled suspensions have been utilized (see, e.g., U.S. Pat. No. 7,276,249, which discloses a process of spray coating nano-suspensions onto large carrier particles). The coated fibrate compositions are alleged to have improved pharmacokinetic profiles and reduced fed/fasted variability. There are some related prior-art documents cited in U.S. Pat. No. 7,276,249 dealing with various aspects of production of nano-suspensions and formation of nano-composite powders. However, these references do not demonstrate the forming of films based on nano-suspensions, or more preferably films containing dry nano/micro drug powders, while most of the references require spray coating to produce the final product that may have improved bioavailability due to faster dissolution.

In general, pharmaceutical thin films have attracted attention recently because of their improved patient compliance and the potential for scaling, continuous processing and cost-effective manufacturing. When administered via the buccal route, these thin films rapidly disintegrate in the oral cavity, thereby typically avoiding first pass metabolism and enhancing dissolution and bioavailability of active pharmaceutical ingredients (API).

In general, a desired requirement for incorporating API nanoparticles into thin films is to ensure the drug content uniformity in a film and the stability of its crystalline form. Two commonly used methods for fabrication of pharmaceutical films are hot melt extrusion (HME) and solvent casting technique (SCT). In HME, an API is mixed with a polymer (and excipients) following which both are melted and extruded together through an orifice or die. Broad applications of HME are however limited due to the difficulty in preserving the API in amorphous form and maintaining long term stability. In SCT, polymer-API suspensions or solutions are typically cast on a substrate and dried either via conventional drying techniques (oven drying) or by using a continuous film casting line.

Most of the articles related to SCT address the incorporation of either water soluble APIs or dissolved APIs, where a BCS class II and IV drug compound is dissolved in a suitable non-aqueous solvent. Some of these studies focus on the formulation aspects of films and the impact of processing parameters, and content uniformity are not discussed. U.S. Pat. No. 5,948,430 proposes the use of substantially water soluble low molecular polymers and poly-alcohols for forming films intended for quick disintegration and release of active agents. U.S. Pat. Pub. No. 2007/0087036 discloses the preparation of polymer film coated with water soluble nutritional supplement to at least one side of the film layer. The films were prepared separately, and the nutrient mixture in the powder form having an adhesive was coated on the film.

U.S. Pat. No. 7,241,411 discloses the preparation of pullulan and hydroxypropyl cellulose based edible films loaded with water soluble skin care ingredients and other ingredients. U.S. Pat. No. 6,419,903 proposes the use of low molecular weight HPMC along with pre-gelated starch for formation of quick release films with improved texture and patient compliance. U.S. Pat. Pub. No. 2003/0206942 discloses methods for forming buccal films with improved muco-adhesion and longer retention time in the oral cavity. U.S. Pat. No. 7,648,712 discloses the use of AMBERLITE for taste masking active agents such as dextromethorphan. Water soluble polymers including pullulan are used as film formers for buccal delivery. U.S. Pat. No. 6,596,298 discloses methods for forming pullulan films containing antibacterial agents for dental applications. Most of these disclosures adopt conventional drying techniques or coating processes for film formation, and a primary focus is placed on improvement of texture, disintegration and muccoadhesion of films for buccal applications. These disclosures do not discuss the impact of processing parameters or drying methods on final film quality.

In one of the earlier works on SCT, U.S. Pat. No. 4,136,145 disclosed the use of convective drying methods for fabrication of orally dissolving films containing an active agent. However, in a later study conducted by Schmidt (U.S. Pat. No. 4,849,246) it was reported that the processing regimes suggested by U.S. Pat. No. 4,136,145 resulted in non-uniform films. These drawbacks were attributed to long drying times associated with the processing conditions suggested by the '145 patent.

U.S. Pat. No. 5,629,003 discusses the importance of film precursor viscosity on final uniformity of film, and proposes the use of film modifiers or viscosity enhancing agents in the film formulation. This method also proposes the use of a film coating unit for drying of the films. U.S. Pat. No. 7,824,588 discloses the preparation of pullulan and hydroxypropyl cellulose based edible films loaded with water insoluble pharmaceutical active ingredients. Films having different thicknesses loaded with active ingredients were prepared at different drying conditions. The uniformity of active ingredient in the films was measured by weight measurements of cut films, and with UV absorption studies. U.S. Patent Pub. No. 2008/0075825 discloses the use of flavoring agents like orange flavor, mint flavor, etc., as de-foaming agents.

The use of de-foaming agents could lead to inhomogeneous film as these agents impact the spreading of suspensions onto the substrate. This disclosure discusses in detail, various problems associated with air entrapment in films. However, the drying techniques discussed in the disclosures of U.S. Pat. No. 7,824,588, U.S. Patent Pub. 2008/0075825 and U.S. Pat. No. 5,629,003 are applied to melted suspensions obtained through HME techniques. As mentioned previously, this method leads to amorphous APIs, which tend to re-crystallize. Thus, maintaining the long-term stability of these dosages remains a challenge. Moreover, these drying methods use high temperatures (beyond the melting point of the API) and harsh drying conditions, which cannot be applied for SCT or even in cases where the API is protein based (like insulin) or heat sensitive.

The prior art does not discuss the incorporation and stabilization of nano and/or micro BCS class II API particles in strip films. As can be inferred from the discussions above, there are some challenges associated with strip film technology, e.g., maintenance of API content uniformity and retaining the API structure or form. Yang (U.S. Pat. No. 7,824,588) discusses the various factors that could affect the final content uniformity of the film: formation of air pockets during mixing, improper casting, viscosity of the starting precursor solutions, improper drying methods (associated with long drying times), final water content of films, etc. These challenges escalate when API is to be incorporated in nano or micro form.

These particles can aggregate or grow if the film processing conditions are not favorable. U.S. Pat. Pub. No. 2011/0305768 discloses the preparation of quick dissolving films containing pH-sensitive micro particles encapsulated with bioactive agents. The pH-sensitive micro particles were prepared by a double emulsion solvent evaporation method. Though this method offers targeted release of protein-based compounds, it is a complicated and time-consuming process. Further, this method is not cost effective, and the final product may contain residual organic solvents. Researchers have discussed the incorporation and stabilization of micro griseofulvin (GF) particles produced via a liquid anti-solvent precipitation (LASP) method into HPMC strip films, which also suffers from the potential problem of residual organic solvents.

Thus, an interest exists for improved systems and methods for improved stripfilm based pharmaceutical products. These and other inefficiencies and opportunities for improvement are addressed and/or overcome by the systems, assemblies and methods of the present disclosure.

SUMMARY OF THE DISCLOSURE

The present disclosure provides improved stripfilm based pharmaceutical products (e.g., for enhancing dissolution and bioavailability). More particularly, the present disclosure provides improved systems/methods for fabricating stripfilm based pharmaceutical products by utilizing higher viscosity film forming precursors and drying methods that accomplish improved/faster drying and provide improved/excellent content uniformity of active pharmaceutical agents in the fabricated stripfilm based pharmaceutical products.

In exemplary embodiments, the present disclosure provides for the fast drying (e.g., via low temperature forced convection with or without gentle infra-red heating) of biocompatible polymer films loaded with poorly water-soluble drug nano-particles.

In the present disclosure, a novel and versatile format based on strip-films is provided, the improved stripfilm offering many advantages, as well as offering easy and economically feasible manufacturability.

The present disclosure provides for a method for fabricating a stripfilm based pharmaceutical product including providing a film forming precursor composition; providing active agent particles; mixing the film forming precursor composition with the active agent particles to form a mixture, the mixture of the film forming precursor composition and the active agent particles having a viscosity of from about 100 cP to about 25,000 cP; drying and fabricating the mixture of the film forming precursor composition and the active agent particles to form a film; wherein the mixture of the film forming precursor composition and the active agent particles is dried at about 0° C. to about 80° C. for about 10 minutes to about 90 minutes to form the film.

The present disclosure also provides for a method for fabricating a stripfilm based pharmaceutical product wherein the mixture of the film forming precursor composition and the active agent particles has a viscosity of at least 2,500 cP. The present disclosure also provides for a method for fabricating a stripfilm based pharmaceutical product wherein the mixture of the film forming precursor composition and the active agent particles has a viscosity of at least 6,000 cP. The present disclosure also provides for a method for fabricating a stripfilm based pharmaceutical product wherein the mixture of the film forming precursor composition and the active agent particles has a viscosity of from about 4,000 cP to about 25,000 cP.

The present disclosure also provides for a method for fabricating a stripfilm based pharmaceutical product wherein the film forming precursor composition includes one or more water-soluble polymers, or one or more water-insoluble polymers. The present disclosure also provides for a method for fabricating a stripfilm based pharmaceutical product wherein the film forming precursor composition includes one or more surface modifying agents. The present disclosure also provides for a method for fabricating a stripfilm based pharmaceutical product wherein the film forming precursor composition includes one or more plasticizers.

The present disclosure also provides for a method for fabricating a stripfilm based pharmaceutical product wherein the active agent particles include one or more active agent micro-particles. The present disclosure also provides for a method for fabricating a stripfilm based pharmaceutical product wherein the active agent particles include one or more active agent nano-particles. The present disclosure also provides for a method for fabricating a stripfilm based pharmaceutical product wherein the active agent particles include one or more pharmaceutical active agent particles.

The present disclosure also provides for a method for fabricating a stripfilm based pharmaceutical product wherein the active agent particles include one or more poorly water-soluble drug particles. The present disclosure also provides for a method for fabricating a stripfilm based pharmaceutical product wherein the active agent particles include one or more BCS Class II or IV poorly water-soluble drug particles.

The present disclosure also provides for a method for fabricating a stripfilm based pharmaceutical product wherein the mixture of the film forming precursor composition and the active agent particles is a suspension of the film forming precursor composition and the active agent particles. The present disclosure also provides for a method for fabricating a stripfilm based pharmaceutical product wherein the active agent particles include one or more particles that are soluble in the mixture of the film forming precursor composition and the active agent particles.

The present disclosure also provides for a method for fabricating a stripfilm based pharmaceutical product wherein the active agent particles include one or more particles having a particle size of from about 5 nm to about 20,000 nm. The present disclosure also provides for a method for fabricating a stripfilm based pharmaceutical product wherein the active agent particles include one or more particles having a particle size of from about 30 nm to about 5,000 nm. The present disclosure also provides for a method for fabricating a stripfilm based pharmaceutical product wherein the active agent particles include one or more particles having a particle size of from about 50 nm to about 300 nm.

The present disclosure also provides for a method for fabricating a stripfilm based pharmaceutical product wherein the drying step includes a drying technique selected from the group consisting conduction, convection, radiation heating and combinations thereof. The present disclosure also provides for a method for fabricating a stripfilm based pharmaceutical product wherein the drying step occurs at least in part under laminar flow drying conditions to form the film. The present disclosure also provides for a method for fabricating a stripfilm based pharmaceutical product wherein the drying step includes convective drying in laminar flow conditions to form the film.

The present disclosure also provides for a method for fabricating a stripfilm based pharmaceutical product further including the step of incorporating the film into a form selected from the group consisting of tablets, capsules and patches. The present disclosure also provides for a method for fabricating a stripfilm based pharmaceutical product further including the step of utilizing the film to encase or encapsulate one or more objects.

The present disclosure also provides for a method for fabricating a stripfilm based pharmaceutical product wherein the drying step includes drying the mixture of the film forming precursor composition and the active agent particles at about 18° C. to about 60° C. for about 10 minutes to about 90 minutes to form the film. The present disclosure also provides for a method for fabricating a stripfilm based pharmaceutical product wherein the drying step includes drying the mixture of the film forming precursor composition and the active agent particles at about 18° C. to about 40° C. for about 10 minutes to about 90 minutes to form the film.

The present disclosure also provides for a method for fabricating a stripfilm based pharmaceutical product wherein the drying step includes drying the mixture of the film forming precursor composition and the active agent particles at about 20% relative humidity to about 90% relative humidity. The present disclosure also provides for a method for fabricating a stripfilm based pharmaceutical product wherein the drying step includes drying the mixture of the film forming precursor composition and the active agent particles at about 30% relative humidity to about 70% relative humidity.

The present disclosure also provides for a method for fabricating a stripfilm based pharmaceutical product wherein the step of providing the active agent particles includes preparing a suspension of active agent nano-particles or active agent micro-particles by utilizing a top down approach. The present disclosure also provides for a method for fabricating a stripfilm based pharmaceutical product wherein the step of providing the active agent particles includes preparing a suspension of active agent nano-particles or active agent micro-particles by utilizing a bottom up approach.

The present disclosure also provides for a method for fabricating a stripfilm based pharmaceutical product wherein the step of providing the active agent particles includes preparing a suspension of active agent nano-particles or active agent micro-particles by an emulsion step. The present disclosure also provides for a method for fabricating a stripfilm based pharmaceutical product wherein the step of providing the active agent particles includes providing active agent nano-particles or active agent micro-particles in dry powder form.

The present disclosure also provides for a method for fabricating a stripfilm based pharmaceutical product wherein the film has an active agent particle loading of from about 0.01 weight % to about 50 weight %. The present disclosure also provides for a method for fabricating a stripfilm based pharmaceutical product wherein the film has an active agent particle loading of from about 0.50 weight % to about 30 weight %.

The present disclosure also provides for a method for fabricating a stripfilm based pharmaceutical product wherein the film forming precursor composition is an aqueous polymeric system. The present disclosure also provides for a method for fabricating a stripfilm based pharmaceutical product wherein the film forming precursor composition includes water and an organic solvent. The present disclosure also provides for a method for fabricating a stripfilm based pharmaceutical product wherein the film is formed by casting the mixture of the film forming precursor composition and the active agent particles onto a substrate. The present disclosure also provides for a method for fabricating a stripfilm based pharmaceutical product wherein the film forming precursor composition includes one or more viscosity enhancers or disintegrants. The present disclosure also provides for a method for fabricating a stripfilm based pharmaceutical product wherein the active agent particles are in crystalline or amorphous form or combinations thereof.

The present disclosure also provides for a method for fabricating a stripfilm based pharmaceutical product wherein the film has an active agent particle loading uniformity, the active agent particle loading uniformity varying in uniformity of active agent loading by less than 6% relative standard deviation over 1 mg/cm$^2$ loading of the film. The present disclosure also provides for a method for fabricating a stripfilm based pharmaceutical product wherein the film has an active agent particle loading uniformity, the active agent particle loading uniformity varying in uniformity of active agent loading by less than 3% relative standard deviation over 1 mg/cm$^2$ loading of the film.

The present disclosure also provides for a method for fabricating a stripfilm based pharmaceutical product wherein the mixing step includes mixing the film forming precursor composition and the active agent particles with a stirrer operating at a rotating speed of from about 100 RPM to about 600 RPM. The present disclosure also provides for a method for fabricating a stripfilm based pharmaceutical product wherein the mixing step includes mixing the film forming precursor composition and the active agent particles for about 1 minute to about 6 hours.

The present disclosure also provides for a method for fabricating a stripfilm based pharmaceutical product wherein the drying step includes drying the mixture of the film forming precursor composition and the active agent particles at about 0° C. to about 80° C. for about 15 minutes to about 45 minutes to form the film. The present disclosure also provides for a method for fabricating a stripfilm based pharmaceutical product wherein the fabricated film has a water content of from about 5 weight % to about 8 weight %.

The present disclosure also provides for a method for fabricating a stripfilm based pharmaceutical product further including the step of re-dispersing the fabricated film in a medium. The present disclosure also provides for a method for fabricating a stripfilm based pharmaceutical product wherein the active agent nano-particles or active agent micro-particles are surface modified with one or more hydrophilic substances. The present disclosure also provides for a method for fabricating a stripfilm based pharmaceutical product wherein the film forming precursor composition includes one or more superdisintegrants; wherein the mixture of the film forming precursor composition and the active agent particles has a viscosity of from about 4,000 cP to about 25,000 cP; and wherein due to the high swelling capacity of the one or more superdisintegrants, their addition to the film forming precursor composition raises the viscosity of the mixture.

The present disclosure also provides for a method for fabricating a stripfilm based pharmaceutical wherein the film has an active agent particle loading of from about 0.50 weight % to about 30 weight %; and wherein the content uniformity of the active agent particles in the film indicated by the relative standard deviation of the active agent particle content in the film is less than about 6%. The present disclosure also provides for a method for fabricating a stripfilm based pharmaceutical product wherein the mixing step includes mixing the film forming precursor composition and the active agent particles with a vibratory or planetary mixer. The present disclosure also provides for a method for fabricating a stripfilm based pharmaceutical product further including forming multi-layer structures with the formed film.

The present disclosure also provides for a method for fabricating a stripfilm based pharmaceutical product including providing a film forming precursor composition and active agent particles; mixing the film forming precursor composition with the active agent particles to form a mixture, the mixture having a viscosity of at least 2,500 cP; drying and fabricating the mixture to form a film; wherein the mixture is dried at about 18° C. to about 60° C. and at about 20% relative humidity to about 90% relative humidity for about 10 minutes to about 90 minutes to form the film; wherein the film forming precursor composition includes one or more water-soluble polymers, or one or more water-insoluble polymers; wherein the active agent particles include one or more active agent micro-particles, or one or more active agent nano-particles; wherein the active agent particles include one or more pharmaceutical active agent particles; wherein the active agent particles include one or more particles having a particle size of from about 5 nm to about 20,000 nm; wherein the drying step includes a drying technique selected from the group consisting conduction, convection, radiation heating and combinations thereof; and wherein the film has an active agent particle loading of from about 0.01 weight % to about 50 weight %.

The present disclosure also provides for a method for fabricating a stripfilm based pharmaceutical product including providing a film forming precursor composition and active agent particles; mixing the film forming precursor composition with the active agent particles to form a mixture, the mixture having a viscosity of at least 6,000 cP; drying and casting the mixture to form a film; wherein the mixture is dried at about 18° C. to about 40° C. and at about 30% relative humidity to about 70% relative humidity for about 15 minutes to about 45 minutes to form the film; wherein the film forming precursor composition includes one or more water-soluble polymers, or one or more water-insoluble polymers; wherein the active agent particles include one or more active agent micro-particles, or one or more active agent nano-particles; wherein the active agent particles include one or more BCS Class II or IV poorly water-soluble drug particles; wherein the mixture is a suspension of the film forming precursor composition and the active agent particles; wherein the active agent particles include one or more particles having a particle size of from about 30 nm to about 5,000 nm; wherein the drying step includes convective drying in laminar flow conditions to form the film; wherein the film has an active agent particle loading of from about 0.50 weight % to about 30 weight %; wherein the film is formed by casting the mixture onto a substrate; wherein the film has an active agent particle loading uniformity, the active agent particle loading uniformity varying in uniformity of active agent loading by less than 6% relative standard deviation over 1 mg/cm$^2$ loading of the film; and wherein the fabricated film has a water content of from about 5 weight % to about 8 weight %.

Any combination or permutation of embodiments is envisioned. Additional advantageous features, functions and applications of the disclosed systems, assemblies and methods of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Exemplary embodiments of the present disclosure are further described with reference to the appended figures. It is to be noted that the various steps, features and combinations of steps/features described below and illustrated in the figures can be arranged and organized differently to result in embodiments which are still within the scope of the present disclosure. To assist those of ordinary skill in the art in making and using the disclosed systems, assemblies and methods, reference is made to the appended figures, wherein:

—FIG. 2 is not drawn to scale;

FIG. 11A—(HPMC), FIG. 11B—(HPMC/Glycerin), FIG. 11C—(HPMC/NaAlg/Glycerin), and FIG. 11D—(NaAlg/Glycerin);

FIGS. 25A-D show dissolution profiles of: (A) fenofibrate (FNB), (B) ibuprofen (IBU), (C) naproxen (NPX), and (D) azodicarbonamide (AZD) films with and without surfactant;

FIG. 26A is from films formed using high viscosity precursors and convection dried (RF2); whereas FIG. 26B is for films produced from lower viscosity precursors and dried over-night in an oven without convection (RF1);

DETAILED DESCRIPTION OF DISCLOSURE

Figure 1:
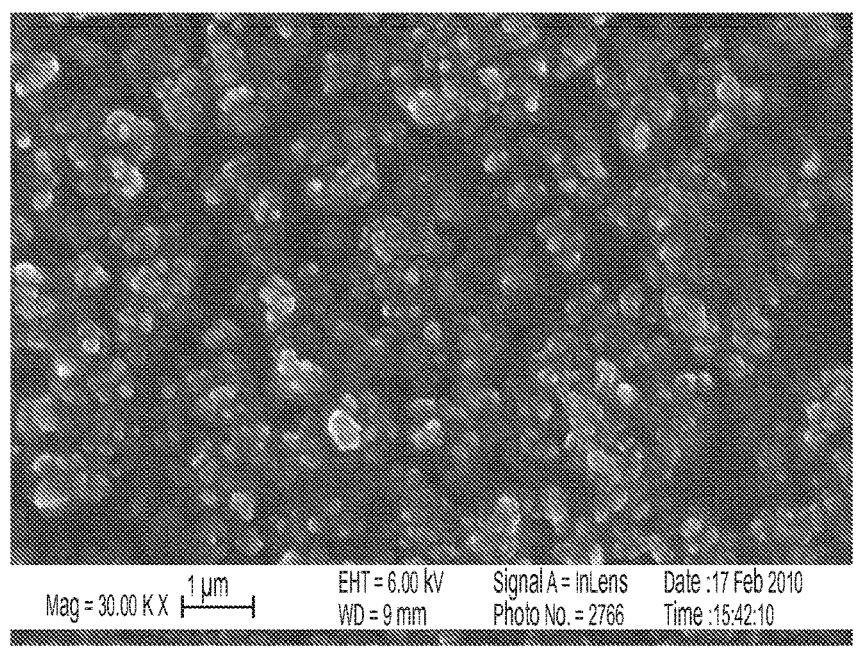
FIG. 1 is a SEM image of a GF nano-suspension produced via WSMM.

The following is a detailed description of the disclosure provided to aid those skilled in the art in practicing the present disclosure. Those of ordinary skill in the art may make modifications and variations in the embodiments described herein without departing from the scope of the present disclosure. Unless otherwise defined, the technical and scientific terms used herein have the same meaning as commonly understood by one of ordinary skill in the art. The terminology used in the description of the disclosure herein is for describing particular embodiments only, and is not intended to be limiting of the disclosure. All publications, patent applications, patents, figures and other references mentioned herein are expressly incorporated by reference in their entireties.

The exemplary embodiments disclosed herein are illustrative of advantageous stripfilm based pharmaceutical products, and systems of the present disclosure and methods/techniques thereof. It should be understood, however, that the disclosed embodiments are merely exemplary of the present disclosure, which may be embodied in various forms. Therefore, details disclosed herein with reference to exemplary stripfilm based pharmaceutical products/fabrication methods and associated processes/techniques of assembly and use are not to be interpreted as limiting, but merely as the basis for teaching one skilled in the art how to make and use the advantageous stripfilm based pharmaceutical products/systems and/or alternative products/assemblies of the present disclosure.

The present disclosure provides improved stripfilm based pharmaceutical products (e.g., for enhancing dissolution and bioavailability). More particularly, the present disclosure provides improved systems/methods for fabricating stripfilm based pharmaceutical products by utilizing higher viscosity film forming precursors and drying methods that accomplish improved/faster drying and provide improved/excellent content uniformity of active pharmaceutical agents in the fabricated stripfilm based pharmaceutical products. In exemplary embodiments, the present disclosure provides for the fast drying (e.g., via low temperature forced convection) of biocompatible polymer films loaded with poorly water-soluble drug nano-particles.

It is noted that a solvent casting technique (SCT) based process for achieving high drug loadings by incorporating nano-sized particles of poorly water-soluble drugs into hydroxypropyl methylcellulose (HPMC) films has been developed. The nano-suspensions were produced by wet stirred media milling (WSMM). These nanoparticles were incorporated into low molecular weight HPMC (E15LV) films for quick dissolution and release of API. A film was fabricated by drying in a lab oven for about 12 hours, thus taking a long time. The API particles were shown to maintain the nano-scale size and the crystalline form. However, they did not provide the details of the dosage-to-dosage drug content uniformity or RSD (relative standard distribution), which is expected to be very high since the precursors generally did not have sufficiently high viscosity, and the drying time was high. In summary, although there are many reports related to forming of nano-composites or of preparing pharmaceutical films, these reports do not discuss the aspects of manufacturability in the form of films loaded with poorly water soluble drugs or active ingredients and achieve excellent drug content uniformity. More specifically, they do not consider the impact of processing and drying conditions on film quality or the content uniformity of the final film, while achieving very fast drug release from the poorly water soluble drugs.

In exemplary embodiments, the present disclosure provides improved systems/methods for fabricating stripfilm based pharmaceutical products by utilizing higher viscosity film forming precursors and drying methods that accomplish improved/faster drying and provide improved/excellent content uniformity of active pharmaceutical agents in the stripfilm based pharmaceutical products, thereby providing a significant manufacturing, commercial and/or operational advantage as a result.

Exemplary systems/methods of the present disclosure advantageously use high viscosity, bio-compatible polymeric precursors and convective drying for fabrication of thin films loaded with nano and/or micro sized particles of poorly water-soluble active pharmaceutical ingredients (APIs) to achieve improved active content uniformity and very fast dissolution from poorly water soluble actives, while accomplishing fast drying during the fabrication process. By adjusting the film forming polymer composition as well as film thickness, the films can also serve for the purpose of extended release of active substances of poorly water soluble drugs.

In exemplary embodiments, the methodology disclosed herein has inherent advantages of obtaining improved/good drug dispersion and high loadings (e.g., since one can use drugs in particulate form). Moreover, the stable nano/micro suspensions along with mixing at high-shear (yet low shear-rate during mixing) required due to the high viscosity of the polymeric mixture leads to this important feature; and works well for both suspensions and dry powders. The present disclosure shows how to enhance viscosity without using expensive gums or similar additives. The present disclosure allows for faster dissolution hence potentially higher bioavailability. The present disclosure provides examples of dissolution curves. Another important feature of the present disclosure is that one can tailor release profiles even for poorly water soluble drugs via just manipulating the matrix and/or film thickness.

In exemplary embodiments, the present disclosure provides for a quick-dissolving thin film composition including: i) one or more water-soluble polymers; ii) one or more surface modifying agents (e.g., surfactants), iii) one or more optional plasticizers (if desired), and iv) one or more drug nanoparticles or microparticles. Further embodiments also include one or more of the following: a) viscosity enhancers, b) water insoluble additives, c) pH sensitive polymeric additives, d) water soluble active ingredients, e) flavor or taste enhancers, f) taste-masking agents, g) matrix formers (e.g., sugars or polyols), h) disintegrants intended for faster film disintegration, or i) muco-adhesive polymers.

In certain embodiments, APIs of poorly water-soluble drugs are used in the form of a stable aqueous suspension of nano and/or micro sized particles, the particles ranging from about 10 nm to about 10 microns, more preferably, from about 50 nm to about 5 micron in size. In further embodiments, dry micronized drug powders are used in the size range of about 200 nm to about 10 microns, or more preferably from about 500 nm to about 5 microns. It is noted that even larger particles can be used (although this can lead to slower dissolution and may not be suitable for very thin films). In certain embodiments, drug particle suspensions or drug powders contain surface modifiers to enhance dissolution or mixing uniformity. Drug particle suspensions or dry powders can be mixed with suitable biocompatible polymeric solutions. In further embodiments, the solutions are aqueous-based. Mixing can be accomplished using stirred, planetary, or vibratory mixers.

For certain embodiments, the drug-polymer mixture is the film-precursor and has high viscosity ranging from about 100 cp to about 25000 cp, more preferably from about 1000 cp to about 20000 cp. The film-precursor can be cast onto a stationary or a moving substrate using a dispensing/casting system (e.g., a system that allows for depositing and which maintains uniform wet film thickness). The substrate can be selected based on its surface interactions with the film precursor such that it allows film deposition without subsequent spreading or shrinking of the film, while allowing for easy peeling upon drying.

Thickness of the cast film before drying commences preferably in the ranges from about 100 micron to about 2 mm, but can be more or less depending on the intended application as well as the physical properties of the film precursor. In one embodiment, a cast film is dried in a system that employs heating via conductive and convective means and also employs radiating heating.

In exemplary embodiments, heating is applied in different stages as the substrate moves along the heating chamber. For example, the heating applied can be gentle; hence the substrate is maintained at temperatures that range from about room temperature (RT—e.g., about 18-24° C.) to about 80° C., more preferably from RT to about 60° C., and even more preferably from about RT to about 40° C. In some embodiments, initially, the film is maintained at cooler conditions in a temperature ranging from about 10° C. less than RT to about RT. In exemplary embodiments, convective drying in laminar flow conditions is also employed, with the air temperature ranging from about 20° C. below RT to about 80° C., more preferably from RT to about 60° C., and even more preferably from RT to about 40° C.

The convection is typically counter-flow, e.g., in the direction opposite to the moving substrate, or it is applied in the same direction as the motion of the substrate. In certain embodiments, the convective air velocities are selected so that the flow is in laminar regime. The dry films can be cut into suitable sizes, or used in other ways/manners, including but not limited to incorporation into tablets, capsules, patches, or encasing/encapsulating of other objects, devices including implants and stents, or dosage forms such as tablets.

The system/methods of the present disclosure advantageously improve drug content uniformity and provide a flexible platform for continuous manufacturing of films uniformly embedded with drugs for use in a variety of applications. In certain embodiments, the films are used to contain very poorly water-soluble drugs to achieve very fast dissolution. Alternatively, the embodiments are for highly potent dosage in mg or sub-mg range while obtaining very good drug content uniformity (CU) and low dosage-to-dosage relative standard deviation (RSD) values.

Certain embodiments of the present disclosure result in extremely uniform films with very low variations in API content even for small dosage units (e.g., less than about 3% RSD over 1 mg/cm$^2$ loading).

In exemplary embodiments, the present disclosure provides for a quick-dissolving thin film composition including: i) one or more water-soluble polymers; ii) one or more surface modifying agents (e.g., surfactants), iii) one or more plasticizers, and iv) one or more drug nanoparticles and/or microparticles. The film is cast using film precursors formed by mixing an aqueous polymeric system and the actives.

In exemplary embodiments, the polymeric system is water based and additionally includes one or more of the following: i) water soluble polymers, ii) water insoluble polymers and additives, iii) surface modifying agents, iv) defoaming agents, v) colors, vi) flavors, vii) taste-masking agents, viii) sugars, polyols, and other matrix formers, ix) viscosity enhancers, x) disintegrants, and xi) organic solvents. In further embodiments, the actives are drug particles in aqueous suspensions or in dry powder form. In yet further embodiments, the drug materials are in crystalline or amorphous form, or can be a combination thereof. In certain embodiments, the drugs are from BCS Class II or IV (and thus are poorly water soluble), and are incorporated as nano and/or micro particles in biocompatible polymers, where improved drug content uniformity and fast dissolution are achieved. In certain embodiments, the film thickness is manipulated to obtain desired dissolution rates, and/or the type of water soluble polymer used for the film precursor is chosen specifically to do same.

Exemplary embodiments utilize high viscosity precursors which are amenable for subsequent processing via gentle, yet fast drying.

In certain embodiments, the film forming precursors have a viscosity in the range of from about 2500 cP to about 25,000 cP, preferably in the range between about 4000 cP to about 18,000 cP and more preferably from about 6000 to about 12,000 cP. For example, the film precursor composition can be aqueous, or it can contain an organic solvent in addition to water, and include one or more of: i) one or more water-soluble polymers; ii) one or more surface modifying agents such as surfactants, iii) one or more plasticizers, and iv) one or more drug nanoparticles or micro-particles.

In some embodiments, the one or more drugs used are poorly water soluble, of BCS Class II or IV. In further embodiments, the one or more drugs also have appreciable solubility in water or a combination of water and organic solvents, such that the drug is substantially dissolved in the film precursor at about room temperature. In certain embodiments, the size of the poorly water soluble API nano/micro particles have a size in the range of from about 5 nm to about 20,000 nm, preferably in the range of from about 30 to about 5000 nm, and more preferably in the range from about 50 to about 300 nm.

In exemplary embodiments, drying is based on conduction, convection, or radiation heating modes, and/or a combination thereof. In further embodiments, drying is accomplished in multiple stages, each stage including conduction, convection, or radiation heating modes (and/or combinations thereof), thereby providing different heating and/or cooling. In further embodiments, during drying, the environmental air is conditioned to maintain the temperature and humidity. For certain embodiments, the drying air temperature ranges from about 20° C. below RT to about 80° C., more preferably from about RT to about 40° C. and at humidity ranges from about 20 to about 90% relative humidity (RH), and more preferably from about 30 to about 70% RH. In further embodiments, the drying air temperature and humidity varies with time.

In certain embodiments, the API nano/microparticles are prepared in suspension form using a top down approach, such as wet stirred media milling. In further embodiments, the API nano/microparticles are prepared in suspension form using a bottom up approach such as precipitation. In still further embodiments, the API nano/microparticles are prepared in dry powder form using a top down approach, such as jet milling or fluid energy milling. In certain embodiments, APIs having low melting point (e.g., below about 100° C.) are formed into particle suspensions using an emulsion approach, such as oil (molten drug) in water melt emulsion. In some embodiments, the produced films have drug loadings in the range of from about 0.01 wt % to about 50 wt %, more preferably API loading range is in the range of from about 0.5 wt % to about 30 wt %, more preferably the API loading range is from about 10 to about 30 wt %.

In certain embodiments, the mixing of the polymer solution and API suspensions or powders is achieved using a lab scale overhead stirrer having a rotating speed in the range of about 100 RPM to about 600 RPM, preferably in the range of from about 200 RPM to about 300 RPM. For example, the mixing time can be kept in the range of from about 30 min to about 6 hours, preferably in the range of about 1 hour to about 3 hours. In further embodiments, the mixing of polymer solution and API suspensions or powders is achieved using a vibratory mixer (e.g., LabRAM) operating at an acceleration of about 10 to about 100 times gravity, preferably in the range of about 50 to about 100 times gravity. For example, mixing time can be kept in the range of about 1 min to about 30 min, preferably in the range of about 5 to about 15 minutes. In further embodiments, the mixing of polymer solution and API suspensions or powders is achieved using a planetary centrifugal mixer (e g, Thinky) operating at an acceleration of about 50 to about 400 times gravity, preferably in the range of about 100 to about 350 times gravity. The mixing can be dominated by two centrifugal forces, e.g., rotation around the central axis (mixing mode) and revolution around the sample axis (de-foaming mode), to achieve even dispersion and de-aeration while mixing materials of high viscosity. The mixing speed can be in the range of 1500 rpm to 2200 rpm, more preferably 1700 to 200 rpm, with a mixing time ranging from 2 to 30 mins, more preferably 5 to 20 mins. The de-foaming speed can be in the range of 1500 to 2200 rpm, more preferably 2000 to 2200 rpm, with a time range of 20 to 30 minutes.

In exemplary embodiments, the films are manufactured in a batch or continuous drying apparatus within about 10 to about 90 minutes, preferably in the range of from about 15 to about 45 minutes. In certain embodiments, a continuous drying line is composed of conduction or convection mode or a combination of conduction and convection mode of heating the substrate. The substrate in such embodiments can be any suitable material (e.g., silicone coated Mylar or steel substrate). The continuous drying line can be composed of counter current laminar airflow conditions with Reynolds number less than 2300, preferably in the range of about 100 to about 1000.

In certain embodiments, the film drying temperatures are in the range of about RT to about 80° C., and more preferably between about 30° C. to about 60° C. In certain embodiments, the dried films contain a final water content in the range about 5 wt % to about 8 wt %. It is noted that the low water content in the final film helps slow down the degradation process, thus aiding in long term film stability.

In certain embodiments, the uniform mono layer films are fabricated with minimum number of components (e.g., a film forming polymer, plasticizer and API nano/micro particles and/or other ingredients), while still retaining the desired/required texture and/or strength (the mechanical strength of the films has been found to be comparable or better than that of commercially available strip films, such as Listerine strip films). In further embodiments, the films are manufactured with other ingredients (e.g., film modifiers, flavoring agents, anti-foaming agents, taste masking components etc., and mixtures thereof).

In certain embodiments, the composition of the film is varied such that the release profiles of the API are modified to immediate, sustained or controlled release. In certain embodiments, the film disintegration time is achieved within about 10 seconds to about 3 min depending on the thickness of films. In further embodiments, the prepared API laden films are rolled or layered by the stacking up of individual mono layer films having various thicknesses. In further embodiments, multi-layer films are prepared by directly dispensing additional layers where each previous layer is fully or partially dried before dispensing the subsequent layer(s). Each layer of the film in either case could have the same composition or may have differing compositions, including the drug content or types to form a variety of dosage forms.

In certain embodiments, the content uniformity of the API in the films indicated by the relative standard deviation (RSD) of the API content in the films is less than about 5% for API loading in the range of about 0.5 wt % to about 30 wt %. In further embodiments, about 100% recovery of the API from the films is achieved in non-aggregated form upon re-dispersing the film in a given medium. In yet further embodiments, the proposed method is extended for incorporation of soluble API, amorphous API, proteins, enzymes etc.

In certain embodiments, the fabricated films are used for the oral, buccal or sublingual delivery of API. In further embodiments, the films are used for dermal patches and skin delivery. In yet further embodiments, the films contain one or more active ingredients selected from the antibiotic, antibacterial, antimicrobial and anti-pain substances, and can be used as a wrap of biocompatible devices, stents and prosthetics. In further embodiments, the films are used to form multi-layer structures, wherein each film includes none or one or more APIs; or disintegrants, or enteric polymers, and the multi-layer structures are used to form tablets, one or more film layers are coated on to tablets, either placebo or containing active ingredients. In further embodiments, films containing compaction sensitive or pressure-label actives are adhered to tablets, either placebo or containing active ingredients.

EXEMPLARY EMBODIMENT EXAMPLES

In certain embodiments, poorly water-soluble drugs are utilized. Thus, drugs that are classified as Class II or Class IV of the Bio-pharmaceutical Classification System (BCS) are advantageously incorporated into such advantageous films. Suitable class II drugs include, but are not limited to, amprenavir, aripiprazole, atorvastatin, atorvastatin calcium, atovaquone, azithromycin, budesonide, calcitriol, candesartan cilexetil, carbamazepine, carisoprodol, celecoxib, clopidogrel bisulfate, clotrimazole/betamethasone, cyclosporine, dapsone, diclofenac sodium, dicyclomine hcl, dronabinol, duloxetine, dutasteride, etodolac, ezetimibe, felbamate, felodipine, fenofibrate, flecainide, fosamprenavir, furosemide, gemfibrozil, glimepiride, glipizide, glyburide, griseofulvin, hydroxychloroquine, hydroxyzine, ibuprofen, indinavir sulfate, indomethacin, irbesartan, isradipine, ketoconazole, lactulose, lamotrigine, lansoprazole, latanoprost, lopinavir/ritonavir, loracarbef, loratadine, lovastatin, mebendazole, meclizine, medroxyprogesterone acetate, meloxicam, metaxalone, methylphenidate HCl, methylphenidate HCl, methylphenidate HCl, methylprednisolone, mycophenolate mofetil, mycophenolic acid, nabumetone, naproxen, nelfinavir mesylate, nevirapine, nifedipine, olanzapine, omeprazole, oxaprozin, phenazopyridine, phenytoin sodium, pioglitazone HCl, piroxicam, primidone, prochlorperazine, pyrimethamine, quetiapine fumarate, raloxifene HCl, rifabutin, rifampin, risperidone, ritonavir, simvastatin, spironolactone, spironolactone, sulfamethoxazole, sulfasalazine, tacrolimus, tacrolimus, telmisartan, temazepam, tipranavir, travoprost, triamcinolone, ursodiol, aka ursodeoxycholic acid, valproic acid, valsartan, vardenafil, verapamil HCl, vitamin d, ergocalciferol, warfarin sodium, ziprasidone HCl and combinations thereof.

Suitable class IV drugs include, but are not limited to, acetaminophen, acetazolamide, acyclovir, azathioprine, azithromycin, bisoprolol, calcitriol, carisoprodol, cefdinir, cefixime, cefuroxime axetil, cephalexin, chlorothiazide, clarithromycin, cyclosporine, dapsone, dicyclomine hcl, dronabinol, dutasteride, etoposide, furosemide, glipizide, griseofulvin, hydrochlorothiazide, hydrochlorothiazide, hydrochlorothiazide, indinavir sulfate, isradipine, linezolid, loperamide, mebendazole, mercaptopurine, mesalamine, methylprednisolone, modafinil, nabumetone, nelfinavir mesylate, norelgestromin, nystatin, oxcarbazepine, oxycodone HCl, progesterone, pyrimethamine, ritonavir, spironolactone, sulfamethoxazole, sulfasalazine, tadalafil, triamcinolone acetonide, trimethoprim and combinations thereof.

Additionally, in terms of their applicability, the examples include but are not limited to class II or IV drugs, including: antiepileptic agents such as carbamazepin, phenytoin, and valproic acid; antifungal agents such as griseofulvin, ketoconazole, and nystatin; antibiotics, including anti-bacterials agents such as cephalexin, cefuroxime, cefixime, clarithromycin, loracarbef, nitrofurantoin, rifampin, sulfamethoxazole, trimethoprim; antiemetic agents such as hydroxyzine and meclizine; anti-inflammatory agents such as, indomethacin, etodolac, dichlofenac, ibuprofen, naproxen, oxaprozin, meloxicam, betamethasone, triamcinolone, sulfasalazine, nabumetone, methylprednisolone, triamcinolone acetonide and combinations thereof.

In exemplary embodiments, the drugs are incorporated in films either as suspensions or in dry micronized powder form. It is noted that the latter can make this process less expensive and has many advantages over traditional oral dosage forms, like tablets containing micronized particles of poorly water soluble drugs, as will be shown through the below examples. Suspensions provide a very suitable method to incorporate very fine, nano-sized particles and are preferably surface modified using additives as will be illustrated below. In certain embodiments, some exemplary methods for preparing the drug particle suspensions include: (i) via media milling, and (ii) through the precipitation route; which can be by using anti-solvent crystallization or can be through other means such as cooling of solutions to form fine particles.

Drug Particle Suspensions from Milling, in Certain Embodiments:

In exemplary embodiments, drug nano to micro-suspensions were produced using a wet-stirred media mill (WSSM) method using the Microcer model (Netzsch Fine Particle size Technology, LLC, Exton, Pa., USA). The use of this device and the parameters used are illustrative and may be adjusted by those skilled in the art, who may also select other milling devices.

In the Microcer, the milling chamber had a volume of about 80 ml, lined with zirconium oxide. In an exemplary embodiment, griseofulvin (GF) was used as a model BCS Class II drug. Before milling, aqueous suspensions containing as received griseofulvin (Sigma-Aldrich, Saint Louis, Mo.) were prepared as follows, and containing at least one polymer (e.g., hydroxypropyl methylcellulose (HPMC; Methocel E15LV) (Dow Chemical)), and at least one surface modifier (e.g., surfactant=sodium dodecyl sulfate, SDS, Sigma Aldrich, Bellefonte, Pa., USA).

The HPMC and SDS concentrations were set at about 2.5% w/w (with respect to [wrt] water) and about 0.5% w/w (with respect to water), respectively. The HPMC was dissolved in 200 g deionized water using a shear mixer (Fisher Scientific Laboratory stirrer, Catalog no. 14-503, Pittsburgh, Pa., USA) running at a fixed speed of 300 rpm for 30 min, to make a 2.5% w/w HPMC solution. The SDS was then dissolved in the HPMC solution and stirred for 15 additional minutes.

The API (GF 10% w/w, wrt water) was then dispersed into the stabilizer solution with the shear mixer running for 30 minutes. A sample of the drug suspension was taken at the end of mixing and was reported as the initial particle size of the drug (11.8 µm). The GF suspension prepared via mixing was subsequently milled in a Netzsch wet media mill (Microcer, Fine particle technology LLC, Exton, Pa., USA), which operated in the recirculated mode. Zirconia beads with a nominal size of about 400 µm were used as the milling media, and a 200 µm screen was used to retain the beads in the milling chamber. Zirconia beads with a 50 ml bulk volume were loaded to the milling chamber (80 ml capacity).

The GF suspension was loaded in the holding tank and pumped through the milling chamber at a fixed speed of about 126 ml/min, using a peristaltic pump. Milling continued for about 60 minutes, at a rotor tip speed of 10.5 m/s. The final median particle size obtained was about 163 nm.

The temperature inside the mill was maintained at less than about 32° C., with the help of a chiller (Advantage Engineering, Inc., Greenwood, Ind., USA). After about 60 minutes of milling, the median particle size of GF particles was decreased from about 11.8 µm to about 163 nm. FIG. 1 shows a scanning electron micrograph of the nanoparticles produced using the WSMM process as described, resulting in substantially rounded nanoparticles that are partially covered by the adsorbed polymer (HPMC), which was part of the milling formulation.

Drug Particle Suspensions from Precipitation, in Certain Embodiments:

In exemplary embodiments, the formation of drug suspensions is done through the precipitation route, and the liquid anti-solvent approach is illustrated. Fenofibrate (FNB, from Jai Radhe Sales, Ahmedabad, India) was used as an exemplary compound, which has a very low aqueous solubility (less than 0.5 mg/L), and is a neutral lipophilic compound (log P=5.24, MW=360.831 g/mol), and is used as a lipid-lowering drug.

The solvent acetone (ACS reagent, greater than or equal to 99.5%) was from Sigma Aldrich (St. Louis, Mo., USA). The polymeric stabilizer used was hydroxy propyl methylcellulose (HPMC, E3 grade, with viscosity 2.4 to about 3.6 cps; Dow Chemicals, Midland, Mich., USA). The surface stabilizing surfactant used was pluronic F-68 (PF-68) (MW=8400 g/mol), from Sigma Aldrich (St. Louis, Mo., USA).

The liquid anti-solvent precipitation was performed using a T-mixing device that was also sonicated. The T-mixer was designed from a 2 inch ID (inner diameter) by 2 inch length cylindrical delrin purchased from McMaster Can (Santa Fe Springs, Calif., USA). Two side holes of 0.0787 inch OD (outer diameter) were drilled to make inlets for the anti-solvent and organic solutions.

The T-mixer outlet of 0.1875 inch OD was also drilled for the exit stream of anti-solvent and solution. The ultrasound pocket was drilled for the introduction of the ultrasonic probe (Omni-ruptor 250 by Omni International Inc., USA), which had an 0.5 inch ID.

No specific sealing of the ultrasound was employed to contain the fluid. The T-mixer opening was designed to fit the ultrasound probe, in order to ensure optimum fluid-nozzle contact. The solvent and anti-solvent solutions were pumped through a stainless steel nozzle (0.01 inch. ID) at a flow rate of 16.5 to about 17, and 55.1 to about 2 ml/min into the T-mixer, respectively, using HPLC pumps (Model CP, Laballiance, Pa., USA).

Figure 2:
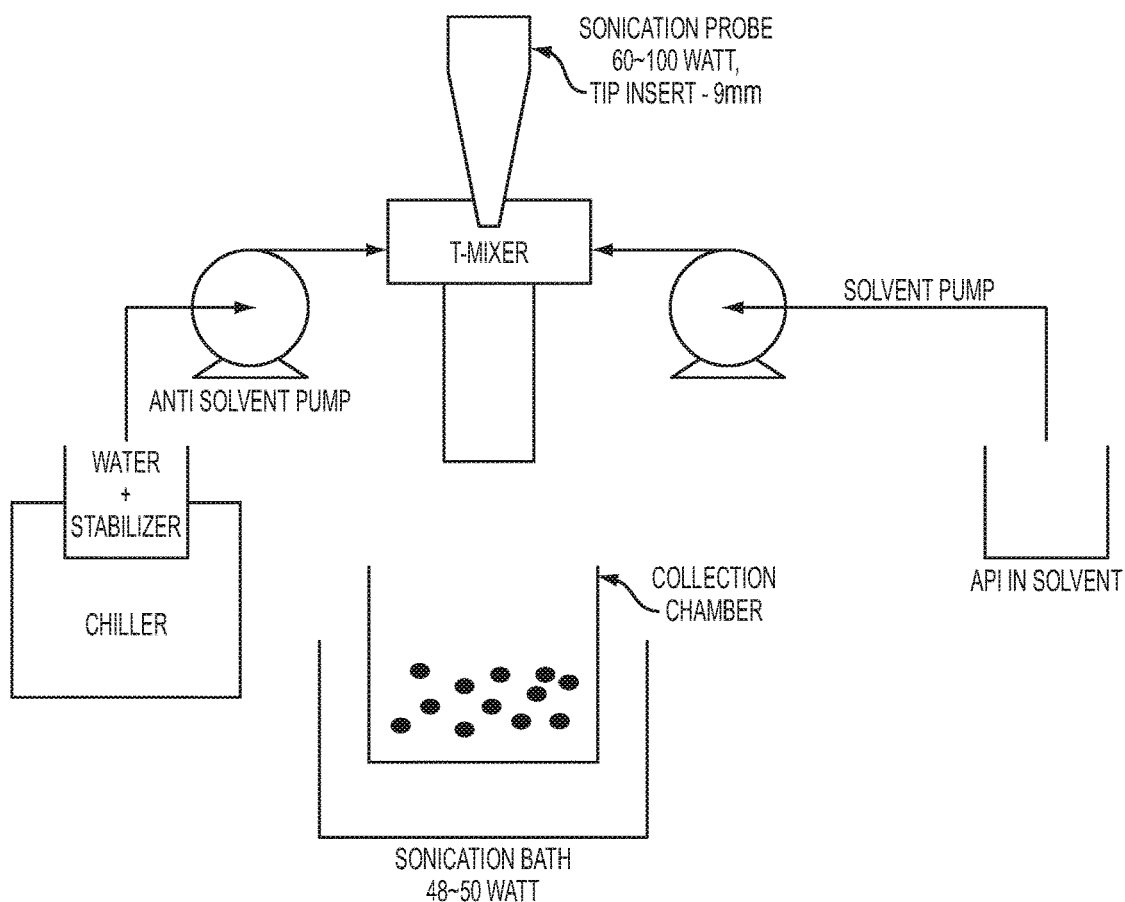
FIG. 2 is a schematic of an exemplary apparatus used for the liquid-anti-solvent precipitation based on a T-mixer
Figure 3:
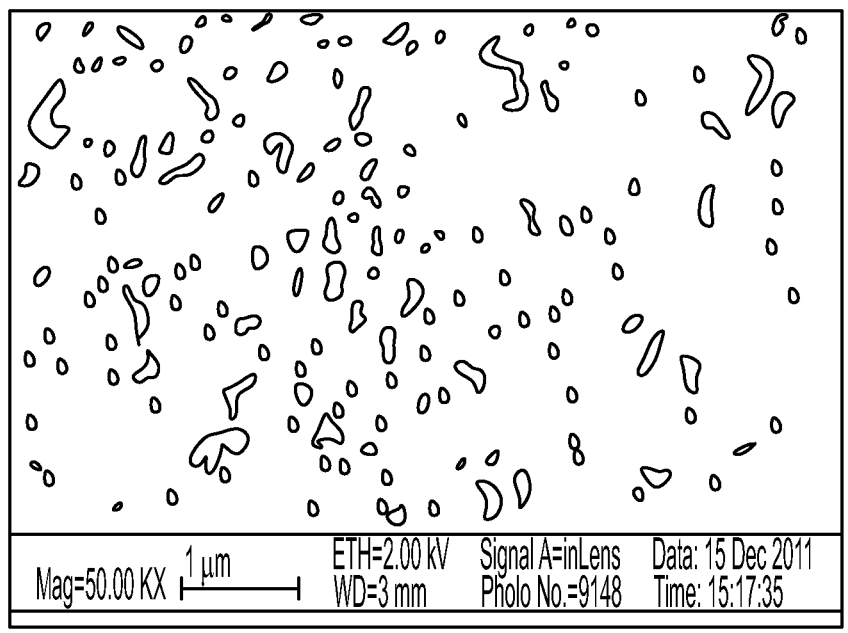
FIG. 3 depicts a SEM micrograph of exemplary precipitated fenofibrate particles from suspensions produced via the liquid-antisolvent method of the present disclosure.

An exemplary schematic of the apparatus setup is shown in FIG. 2. In a typical experiment, 10 ml of acetone containing fenofibrate (2% w/v) was added drop-wise (in three minutes) to 70 ml of de-ionized water (temperature 1° C.) containing 0.5% HPMC and 1% PF-68. During addition, probe sonication was employed at a power of 75 to about 85 watt. All percentages (%) in the suspension preparation refer to w/v with respect to total suspension. The final collected suspension was filtered with a 25 µm sieve to discard possible chunks (greater than 25 µm). After 10 min of the precipitation process, the particle size was measured using Beckmann Coulter LS 13-320 (Miami, Fla., USA), which indicated a size range of about 1 micron, although its SEM micrograph in FIG. 3 shows the presence of 100-200 nm particles in abundance.

Drug Particles from Dry Milling, in Certain Embodiments:

In exemplary embodiments, fenofibrate (FNB, Jai Radhe Sales, Ahmedabad, India) was milled and coated with various amounts of pharmaceutical grade amorphous hydrophilic silica ($SiO_2$, M5P, Cabot Corporation, MA) in a Fluid Energy Mill (FEM, qualification model, Sturtevant Inc., Hanover, Mass.) for 0, 35, 65, and 100% surface coverage of milled drug powders. For surface coverage, the guest weight was estimated based on the guidelines provided in U.S. Patent Pub. No. 2007/0053846 to calculate the amount of silica to use. Accordingly, for 0, 35, 65, 100% coverage, the FNB was coated with 0, 1.5, 3, and 4.8% by weight of silica, respectively. The particles were simultaneously fed into the FEM at a rate of about 3 grams per minute, and the grinding pressure was set to 40 psi. It is noted that such operating conditions may be set by those skilled in art, see for example, U.S. Pat. No. 8,252,370.

The as-received FNB had a particle size of $d_{50}$=10 microns, whereas after milling, the particle size was reduced to $d_{50}$=2 microns. In one exemplary embodiment, 2.5 grams of dry-silica coated FNB particles was then mixed thoroughly with 0.3 grams of sodium dodecyl sulfate (SDS, Sigma Aldrich, Bellefonte, Pa., USA), which was then added to 50 grams of aqueous Hydroxypropyl methyl cellulose (HPMC-E15LV, Dow Chemicals, Midland, Mich., USA) solution and glycerin to prepare the film-precursor containing fine milled FNB particles.

Preparation of Polymer Solutions and Mixing with Drug Suspensions:

In an exemplary embodiment, a polymer solution was prepared by adding a weighed amount of film forming polymer (e.g., HPMC) and a plasticizer (e.g., glycerin) to water (on w/w basis) at about 90° C. The solution was then allowed to cool down to room temperature while being stirred continuously.

The resulting solution was then allowed to rest overnight until substantially no air bubbles were seen. The compositions of the film-precursor slurries used are given in Table 1 below. These compositions were chosen based on preliminary viscosity measurements.

It is noted that the viscosity plays a major role for uniformity of film thickness, as well as API distribution, as will be illustrated further in this disclosure.

Bearing this in mind, two compositions, A and B, were formed by mixing about 12% HPMC and 15% HPMC solutions with drug nano-suspensions (e.g., GF suspensions). Other than the minor wt % difference in the amount of HPMC, the compositions A and B were similar, and both contained glycerin (about 5% w/w) as a plasticizer.

The viscosity of aqueous the HPMC-GF mixed suspensions was measured using an R/S plus Rheometer (Brookfield Engineering, Middleboro, Mass., USA). The Rheometer was equipped with a shear rate controlled coaxial cylinder (CC40), and a water jacket assembly Lauda Eco (Lauda-Brinkmann LP, Delran, N.J., USA). The temperature of the jacket was kept constant at about 25±0.5° C.

The HPMC-GF suspensions were subjected to a low shear rate program, and the viscosity at a fixed low shear value of 2.2 $s^{-1}$ was reported. Measurements were performed in duplicate to check for reproducibility. The resulting viscosities for the two suspensions used in this study were found to be 2400 cPs and 6200 cPs, respectively.

TABLE 1

Wet film compositions for two different viscosity levels of film precursors, forming sample types A and B.

| Wet film composition | Samples A (Viscosity 2400 cPs) | Samples B (Viscosity 6200 cPs) |
| --- | --- | --- |
| GF | 2.95% (w/w) | 2.95% (w/w) |
| HPMC | 8.74% (w/w) | 10.73% (w/w) |
| SDS | 0.15% (w/w) | 0.15% (w/w) |
| Glycerin | 6.66% (w/w) | 6.66% (w/w) |
| Water | 81.5% (w/w) | 79.51% (w/w) |

Mixing of Polymer Solutions with Drug Suspensions:

In exemplary embodiments, it is noted that mixing can be an important and a critical step. In certain embodiments, drug content uniformity in the mixture is maintained and the mixing process is not allowed to substantially result in formation of drug agglomerates or drug-rich areas. Also, in such embodiments, air-bubbles are minimized, unless necessary for a specific application.

In an exemplary embodiment, a polymer solution (50 g) prepared as described above and after it was at room temperature, was added to the nanosuspension produced from WSMM (25 g) in a 2:1 ratio and mixed for 4 hours using a dual-propeller mixer (McMaster, Catalog No. 3471K5, Los Angeles, Calif., USA) attached to a motor (VWR overhear stir VOS 16V120).

The resulting suspension had small amount of air-bubbles, which gradually disappeared when the mixture was left to rest at room temperature for a period of 30 minutes. In such mixing, the API suspensions have low viscosity, whereas the polymeric solutions have much higher viscosity, therefore their intimate mixing is desired/necessary and requires careful considerations, often requiring prolonged mixing. In one preferred embodiment, mixing time may be reduced through step-wise mixing when addition of the polymeric solution is done stepwise, thus mixture viscosity is gradually increased. Those skilled in art can use other mixing systems, which could include either dynamic or static mixing systems, including batch or continuous mixers.

Examples of batch mixers are, those that have propeller, turbine or rake type agitators in vessels, and single stirred mixers (e.g., anchor mixer or helical ribbon mixer), and others such as, single planetary mixer, double planetary mixer, double arm kneader mixers, kneader mixers, or roll mills. For higher viscosity mixing, multi-shaft mixers may be employed, or even specialized equipment such as sonic mixer by MacroSonix (Richmond, Va.), or uni-cyclone mixer from Japan Unix (Fancort Industries, West Cadwell, N.J.), or Thinky® mixer, Microstar Technology Corporation, Bethlehem, Pa. Examples of continuous mixers include single or twin-screw extruders.

Casting and Drying of Films:

In certain embodiments, the film casting is done using a casting knife, Elcometer 3580, or a doctor blade with reservoir, Elcometer 3508 (Rochester Hills, Mich.), or pressurized dies such as those used in extrusion systems, for example, a single-slot die from Extrusion Dies Industries, LLC (Chippewa Falls, Wis.). One main function of the casting system is to produce uniformly thick films without causing thickness variation in lateral or longitudinal directions. The systems for such embodiments ensure that the impacts of shear and casting method on drug particle distribution are minimal.

Figure 4:
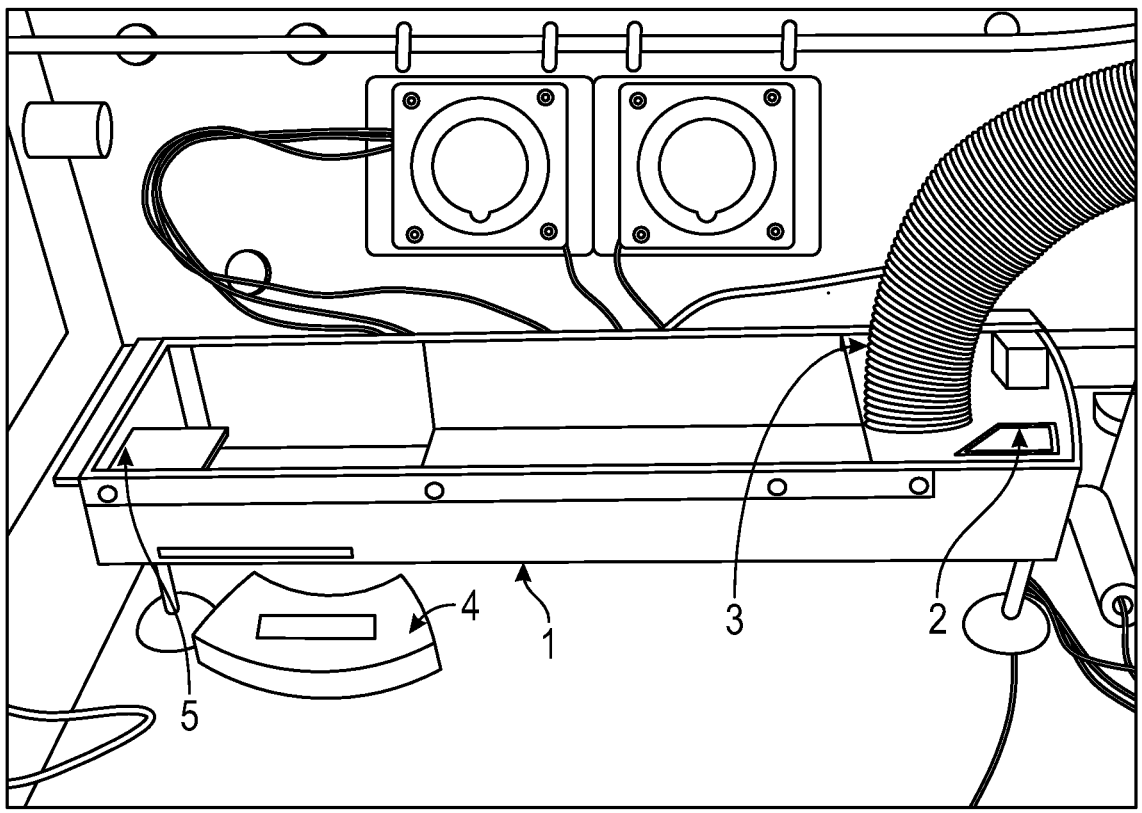
FIG. 4 shows an exemplary convective drying unit/assembly that allows for control of air flow, drying temperature, humidity as well as monitoring of weight loss during drying.

For casting of films, some of the most important features are control of heating in several zones and provision of convective as well as radiative heat-transfer systems. One exemplary device is the HED International Lab-Cast Model, TC-71LC, which was used with success to dry films along with the use of Elcometer 3508 film casting unit. Those skilled in art may be able to develop or design suitable units that allow for drying without adverse impact of convection and radiation used in drying. Another exemplary embodiment is shown in FIG. 4. As such, FIG. 4 shows an exemplary convective drying unit that allows for control of air flow, drying temperature, humidity as well as monitoring of weight loss during drying. It includes a rectangular open-ended chamber made of steel with a transparent glass top for direct observation of the drying process.

Shown in FIG. 4 are: a heating coil 1, an air blower 2 with adjustable flow rate and temperature, a humidifier 3 to vary vapor pressures of water (if necessary), an automated balance 4 to monitor the sample weight, and sensors 5 to monitor temperature and airflow rate.

More particularly, the unit in FIG. 4 is equipped with a heating element 1 (Part No. 35765K279, Mcmaster-Carr, N.J., USA) mounted on the chamber floor, an air blower 2 (Part No. 4184NX, Ebm-papst Inc., CT, USA) with a heating coil mounted on the right end of the chamber (inlet) to control the air velocity and temperature, a humidifier 3 to vary the humidity of air fed into the chamber (if necessary), a rotating vane anemometer (Anemomaster model 6815, Kanomax, N.J., USA) located at the left end of the chamber (outlet) and an automated balance 4 (Scout Pro 202, Ohaus, N.J., USA) connected to the sample stage that is controlled by a computer-based acquisition system to record the sample weight every 15 seconds in the course of drying. By setting the air blower 2 at a desired velocity, air at room temperature of about 25° C. and humidity of about 40-60% is introduced into the chamber. The flow rate and temperature of air exiting the chamber are recorded using the anemometer. In exemplary embodiments, the heating element, the sample stage, and the air flow velocity in the chamber are maintained at the same temperature in the course of drying.

To achieve uniform drying of a polymer-based suspension desired to maintain the film uniformity, the heating element arrangement and the geometry of the chamber and the sample stage were designed such that the air flow pattern is laminar and the air temperature over the sample stage does not substantially vary across the chamber cross-section. The drying unit was placed in operation without a suspension sample until the temperatures of the air exiting the chamber and the heating element reached the temperature setting of the air blower.

A suspension sample that was cast on a 0.4-mm stainless steel plate was then introduced into the chamber through the outlet. As the steel plate and the suspension sample acquired the air temperature within a few seconds, the temperature variation across the sample caused by water evaporation in the course of drying was estimated to be about 1.2° C., which was found to be sufficient to suppress the formation of defects and the buildup of stress as the polymer-based film forms. The sample was held in the chamber until its weight stopped changing.

Film Formulation:

In certain embodiments, the film formulation includes one or more water soluble polymers; surface modifiers (surfactants); muco-adhesive polymers; plasticizers; viscosity enhancing agents, and/or disintegrants. For immediate release of API, low molecular weight water soluble polymers such as Hydroxy propylmethly cellulose (E3, E5, E15LV), hydroxypropyl cellulose, polyvinyl pyrrolidone, carboxymethyl cellulose, pullulan, sodium alginate, polyvinyl alcohol, polyethylene glycol, polyacrylic acid, methylmethacrylate copolymer, carboxyvinyl polymer, amylase, high amylase starch, hydroxypropylated high amylase starch, dextrin, levan, elsinan, collagen, gelatin, zein, gluten, soy protein isolate, whey protein isolate, and/or casein may be utilized.

For extended release applications, high molecular weight water soluble polymers such as Hydroxy propylmethly cellulose (E4M,J series, K series (Dow chemicals)), pectin, carrageenan, chitosan, chitin, xanthan gum, guar gum, gum Arabic are used. For colon specific delivery or targeted delivery of pH sensitive compounds, polymers such as a Eudragit-style copolymer; a pluronic polymer; a chitosan, a chitosan derivative or a combination thereof are used. The term "Eudragit-style copolymer" refers to a polymethacrylate polymer such as, but not limited to Eudragit. L100, Eudragit, S100, Eudragit RL 100, Eudragit RS100, Eudragit E100, Eudragit L100-55, Eudragit E PO, Eudragit RL PO, Eudragit. Additionally, they can also be a mixture of Eudragit L polymer, including, but not limited to Eudragit L100-55, and Eudragit S polymer, including, but not limited to, Eudragit S100. A mixture of Eudragit-style copolymers, Pluronic F-68 and chitosan, or a chitosan derivative is also used in one embodiment. Muco-adhesive polymers are used to increase the adhesion of the unit dosage at targeted areas in certain embodiments. These include but are not limited to, poly(ethyleneimine), poly(acrylic acid), poly(methacrylic acid), poly(ethylene oxide), poly(2-hydroxyethyl methacrylate), poly(L-lysine), and derivatives or copolymers thereof; as well as SA, chitosan, gelatin, collagen, carbopol and derivatives thereof. For controlled release applications biodegradable polymers, co-polymers, block polymers and combinations thereof are used. A few examples include but are not limited to: poly (glyconic acid), polyacetates, polycarbonares poly (lactic acid), polycaprolactone (PCL), polyanhydrides, polylactide (PLA), polylactic co-glycolic acid (PLGA) and mixtures and co-polymers thereof.

Additional compounds in the film formulation in certain embodiments include water soluble surface modifiers such as sodium dodecyl sulfate (SDS), dioctylsulfosuccinate (DOSS), Pluronic F-68 (PF-68, poloxamer 188), cetyltrimethylammonium bromide (CTAB), Pluronic F-127 (PF-127, poloxamer 407), Tween 80 (T-80, a polyethylene sorbitol ester), sodium alginate (SA) and mixtures thereof. Further water-insoluble ingredients such as: (i) a variety of starches that do not dissolve but swell (cornstarch, potato starch, wheat starch, etc.), (ii) superdisintegrants, selected from the group of croscarmellose sodium particles, sodium starch glycolate particles, crospovidone particles, and any ionic/neutral superdisintegrant particles, and (iii) particulate additives such as, Aerosil R972P (or pharmaceutical grade R972P), and other examples include, CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik) are also used.

In certain embodiments, viscosity enhancing agents include high molecular weight polymers, polysaccharides and gums. These include, but are not limited to: guar gum, xanthan gum, dextran, gum Arabic, locust bean gum, tamarind gum, karaya gum, carrageenan, alginate, gellan gum and combinations of thereof. In the present disclosure it is demonstrated that superdisintegrants such as croscarmellose sodium, sodium starch glycolate, and kollidon can also be used as viscosity enhancing agents for improved film performance in example embodiments.

In addition, plasticizers, such as polyethylene glycols, polypropylene glycols, glycerol, glycerol monoacetate, diacetate of triacetate, polyethylene glycol (PEG) 400, propylene glycol (PG), Di-2Etylhexyl Adipate (DOA), polymeric adipates (polyesters of adipic acid) with different viscosities, tributly citrate, cetyl alcohol, triacetin are used in certain embodiments.

Natural and synthetic flavoring agents such as oils, aromatics, extracts derived from leaves, plants and flowers or a combination of these are used in certain embodiments. Examples include but are not limited to: mint oils, citrus oils, cinnamon oil, spearmint oil, thyme oil, cocoa, fruit essences such as apple, pear, peach, cherry, raspberry, orange, grape fruit or other flavorin agents. Sweeteners such as sorbitol, mannitol, xylitol, sucralase, fructose, glucose, etc., may be used. Saliva stimulating agents and coloring agents such as citric, lactic, adipic, succinic, malic, fumaric and tartaric acids can be used. FDA approved coloring agents such as Blue No. 2, Green No. 3, etc., are also utilized in certain embodiments. In example embodiments, the materials selected should adhere to GRAS (generally regarded as safe) requirements.

Drug Content Uniformity and Distribution:

Advantageous aspects of the present disclosure may be illustrated through the results of content uniformity as impacted by film precursor viscosity and drying conditions; as well as dissolution behavior as a function of film formulation, structure and thickness. Considering two film formulations as illustrated in Table 1, and dried using the apparatus of FIG. 4, eight different types of film samples as illustrated in Table 2 were prepared.

The drug content distribution and uniformity were examined using both near-IR (IR) chemical imaging as well as Raman imaging, each affording evaluation at a different scale of scrutiny. Near infrared Hyperspectral images were acquired using the Malvern SyNIRgi NIR-CI System (Malvern, UK). The images were obtained in transflectance mode by placing the polymeric film over a white ceramic disk of a 28 mm diameter. The films were analyzed with a 131 µm/pixel objective which had a field of view of 34×42 mm, and permitted the analysis of the entire film which can be equivalent to one unit dose.

The spectra were obtained with 1 scan in the spectral range of 1300-2300 nm. The data collected was analyzed using the ISys Version 5.0.0.14 software. Before data analysis, all raw reflectance data was converted to absorbance, log (1/R). Pixel correction was applied in order to remove areas of non-uniform illumination and to remove the effect of unresponsive pixels on the detector. The spectra were normalized using Standard Normal Variate (SNV) and a Savitzky-Golay second derivative (filter order 3, filter width 7) in order to eliminate variations in slope. Pure component imaging data was collected from powder samples of the GF and excipients where spectral pretreatment was performed in the same manner.

A reference library with the pure components (GF, HMPC, SDS, Glycerin) spectra was built. The pure component reference spectra were used to build a partial least squares-discriminant analysis (PLS-DA) classification model for GF. Method development included the evaluation of the full spectral range as well and different spectral ranges, however the best calibration model was obtained with the 2000-2300 nm spectral range. Areas of pure GF would have a score value of 1.0 or 100%, and areas without GF a score of value of 0. The score values were used to estimate the drug abundance. The term abundance is used to describe the presence of GF at a specific localized area.

The abundance values obtained were used to create the score images. Since drug rich areas are somewhat difficult to observe in score images, binary images were used to facilitate the visualization of drug rich areas. The binary images were obtained by applying a threshold value, where only pixels with abundance values greater than the mean+2 standard deviations are marked with the black color. The spatial distribution was evaluated by first identifying the drug rich areas where the drug agglomerated, indicating poorer drug distribution. The drug rich areas involve a scale of scrutiny smaller than a typical dose, and also smaller than typical film samples (0.712 $cm^2$) used in some of the subsequent tests reported in this disclosure. The use of binary images facilitated the identification of drug rich areas. Thresholding was employed to obtain the binary images as shown in FIG. 5.

Figure 5:
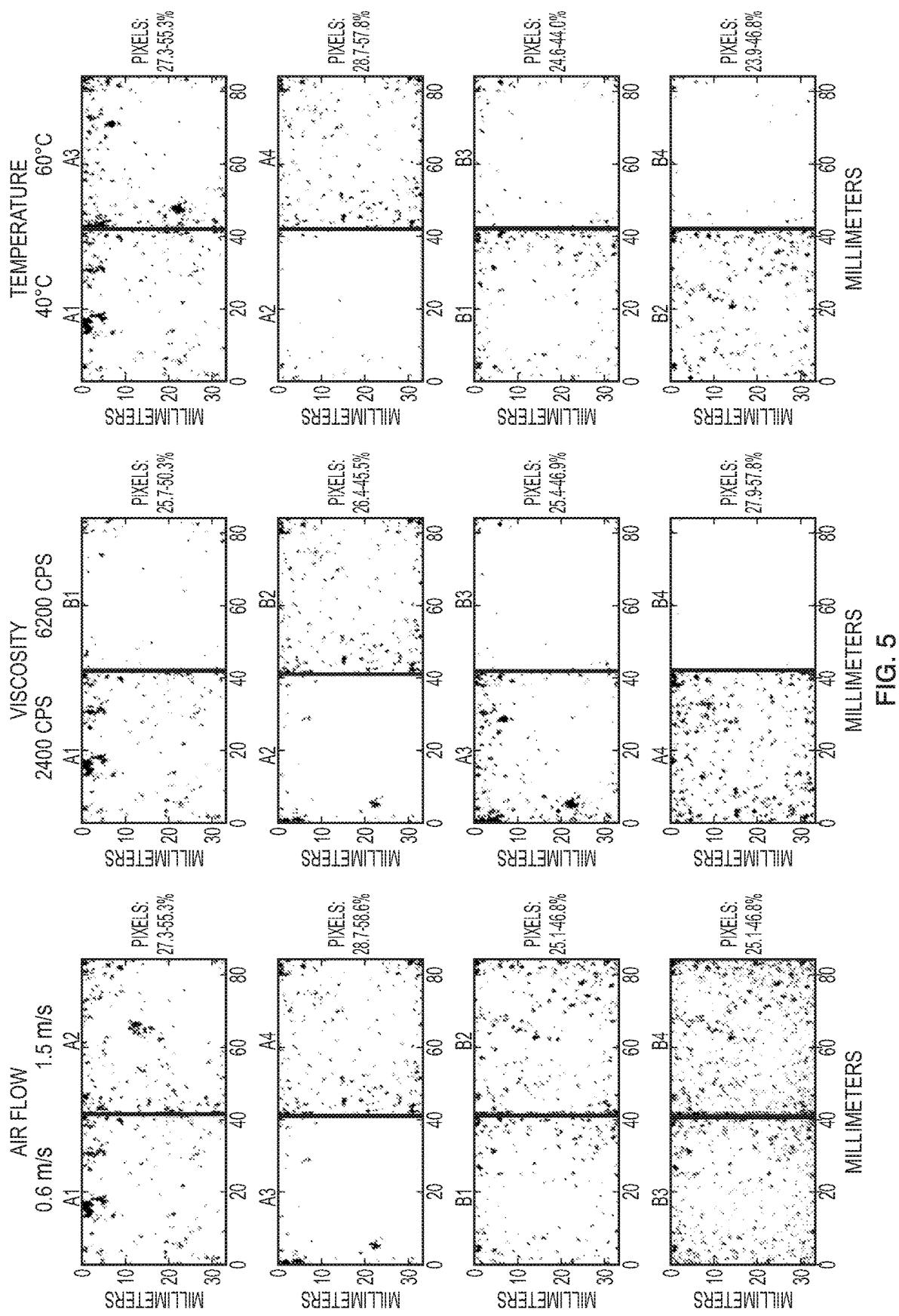
FIG. 5 shows binary images generated from the scores images using the 131 μm/pixel objective; pairwise comparison is made for viscosity differences after threshold is applied; a threshold was established such that only those pixels with values beyond 2 standard deviations of the mean are shown.

In FIG. 5, the dark areas are those with drug abundance higher than the mean plus two standard deviations, and are defined as drug rich areas in this disclosure. The white areas in the binary images correspond to the GF abundances that did not exceed two standard deviations from the mean. Hence, FIG. 5 provides qualitative visual information regarding drug distribution within the film sample, as well as variation within the sample; images with mostly white areas qualitatively indicate absence of drug rich areas and better overall drug distribution. The images in FIG. 5 are presented in three columns; each representing one major formulation or drying condition. Of these three conditions, namely from left to right, air velocity, film precursor viscosity, and drying temperature, the most prominent influence is from the difference in viscosity, because as seen, all higher viscosity cases exhibited more uniformly distributed white areas.

Drug content uniformity of these samples was further examined through evaluation of drug content in small film samples. An Agilent 1100 series HPLC system consisting of a pump and a UV detector were employed for determining the drug content in films, each having an area of about 70 $cm^2$. A 1-cm wide region of a film close to the edges was cut off and ten circular shape samples, each with an area of 0.712 $cm^2$, were punched out from the remaining portion. The samples were then dissolved in 250 ml of 0.025 M SDS solution, following which the concentration was calculated using UV detection at 291 nm (used with a Waters Spherisorb 10 μm CN analytical column (4.6 mm×250 mm)). The temperature was maintained at 25° C.

The mobile phase was a mixture of water and acetonitrile (50:50, v/v) with a flow rate of 1.0 ml/min. The samples were put into HPLC vials and 20 μL was automatically injected into the HPLC system. The concentration was determined from a calibration curve. The average weight in mg of GF and relative standard deviation over ten samples was calculated. Table 3 shows the average content of drug per area for all the film samples. The relative standard deviations (RSD) for all the GF loaded HPMC films were low, with the highest measured value being about 6.2%.

Overall the RSDs for films formed from high viscosity suspensions (composition B) were lower than those for films formed from low viscosity suspensions (composition A). Further, the RSD values for GF films formed from composition B and dried at lower temperature (B1 and B2) were under 3%. These observations are also supported by the NIR chemical imaging results shown in FIG. 5. In these experiments, no specific attempt was made to control film thickness, therefore, the reported drug content RSD values for higher viscosity film precursors and dried at lower temperature are excellent and illustrate a major advantage of the present disclosure.

TABLE 2

Experimental design varying viscosity, drying air temperature, and velocity for forming various film samples of types A and B. Note that film casting thickness was held constant at 1 mm for all cases.

| Sample ID | Viscosity (cPs) | Air temperature (° C.) | Air velocity (m/s) |
|---|---|---|---|
| A1 | 2400 | 40 ± 0.1 | 0.5 ± 0.02 |
| A2 | 2400 | 40 ± 0.1 | 1.5 ± 0.02 |
| A3 | 2400 | 60 ± 0.1 | 0.5 ± 0.02 |
| A4 | 2400 | 60 ± 0.1 | 1.5 ± 0.02 |
| B1 | 6200 | 40 ± 0.1 | 0.5 ± 0.02 |
| B2 | 6200 | 40 ± 0.1 | 1.5 ± 0.02 |
| B3 | 6200 | 60 ± 0.1 | 0.5 ± 0.02 |
| B4 | 6200 | 60 ± 0.1 | 1.5 ± 0.02 |

TABLE 3

Content uniformity result for HPMC films containing GF nanoparticles. Each sample is 0.712 cm$^2$, corresponding to about 1.4 mg dose.

| Sample ID | RSD (%) | Average amount of drug (mg) | Average amount of drug per area (mg/cm2) |
|---|---|---|---|
| B1 | 2.67 | 1.38 | 1.95 |
| A1 | 5.77 | 1.64 | 2.31 |
| B2 | 2.03 | 1.57 | 2.20 |
| A2 | 4.97 | 1.44 | 2.03 |
| B3 | 4.93 | 1.33 | 1.87 |
| A3 | 6.30 | 1.32 | 1.85 |
| B4 | 5.63 | 1.32 | 1.85 |
| A4 | 5.11 | 1.34 | 1.89 |

Recovery and Dissolution of Drug Nanoparticles from Films and the Role of Suspension Stabilization:

The effect of variation in the formulation of milled suspensions on film formation, recovery and dissolution of films of three different BCS Class II drugs, namely Griseofulvin (GF), Fenofibrate (FNB) and Naproxen (NPX) was examined. Nano-suspensions were prepared by wet stirred media milling (WSMM) with different formulations listed in Table 4. All percentages in Table 4 refer to % w/w with respect to de-ionized water in the suspension. The drug was milled with three different formulations: drug alone, with HPMC alone, and with a combination of HPMC and SDS. A solution containing the stabilizers HPMC or HPMC/SDS was prepared by dissolving 2.5% HPMC in 200 g water using a shear mixer (Fisher Scientific Laboratory stirrer, Catalog no. 14-503, Pittsburgh, Pa., USA) at a fixed speed of 300 rpm.

After dissolving the HPMC, 0.5% SDS was added to the HPMC solution for the HPMC/SDS formulations. 10% drug was then dispersed in the stabilizer solution and stirred for 30 min. For milling the drug alone, the drug was simply dispersed in water and used for milling. Following the initial suspension preparation, the suspension was poured into the holding tank of a Netzsch mill (Microcer, Fine particle technology LLC, Exton, Pa., USA) and pumped through the milling chamber at a flow rate of 126 ml/min. Yttrium stabilized zirconia beads with a median size of 400 um and a bulk volume of 50 ml were used as the milling media. GF and NPX were milled for 60 min and FNB was milled for 120 min to reach similar final particle sizes of all drugs.

An aliquot of the suspensions was dispersed in a 10 ml stabilizer solution and the particle size of the suspensions was measured using a Beckman Coulter LS13320 after milling. The particle size statistics of all the suspensions are reported in Table 4. The resulting drug suspensions were mixed with a 10% w/w solution of HPMC E15LV and glycerin in a ratio of 1:1, drug suspension to polymer solution. This suspension was stirred for 3 hours with a dual-propeller mixer (McMaster, Catalog no. 3471K5, Los Angeles, Calif., USA). The particle size of the suspensions was measured after mixing with the polymer solution to check for particle growth.

The foam formed during stirring was allowed to settle and the resulting film-precursors were used for film casting. The suspensions were cast into films with a wet film thickness of 1000 microns and dried at 40° C. The films were then characterized for recovery and dissolution of the drug nanoparticles from films. The median sizes of GF, NPX and FNB suspensions after milling of drug alone were 4, 12 and 10 um, respectively (see Table 4). The primary nanoparticles of these drugs were formed and confirmed via SEM imaging, but they aggregate in the absence of stabilizers. The nanosuspensions of these drugs can be stabilized with the addition of a steric stabilizer, HPMC.

As seen in Table 4, stable nanoparticles of NPX and FNB in the presence of HPMC alone were formed with a median size of 147 and 214 nm, respectively. The median size of GF milled with HPMC was slightly smaller than milling GF alone, but could not be stabilized as well as the other drugs. GF, NPX and FNB have different physicochemical properties. The partition co-efficient, e.g., log P of GF, NPX and FNB were 1.1, 3.0 and 5.4, respectively.

In general, it was observed that drugs with higher log P values could be stabilized by milling with HPMC alone. An interaction between the lyophobic surfaces of the drug candidates and the functionalities in the stabilizer assist the adsorption of the stabilizer on to the particle surface and subsequent stabilization of nanoparticles. Therefore greater the hydrophobicity of the stabilizer, the greater will be the affinity to the particles and more surface coverage is achieved. Stable nanosuspensions of all drugs were formed after milling with a combination of HPMC and SDS (Table 4). SDS improved the wettability of all drugs which further improved the interaction between the drug and polymer, thus, leading to formation of stable nanosuspension. However, the addition of excess SDS can be detrimental to the suspension stability due to Ostwald ripening during the storage of suspensions.

Surprisingly, the median size of the suspensions containing the drug alone was reduced after mixing with the HPMC/glycerin solution, indicating another advantage of the present disclosure. During the mixing step, the drug aggregates were broken down and HPMC was adsorbed on the newly created drug surfaces leading to stabilization of the milled drug suspensions. Similarly, for the GF/HPMC formulation the median size was reduced from 2.6 microns to 389 nm after mixing with the polymer solution.

Figure 6:
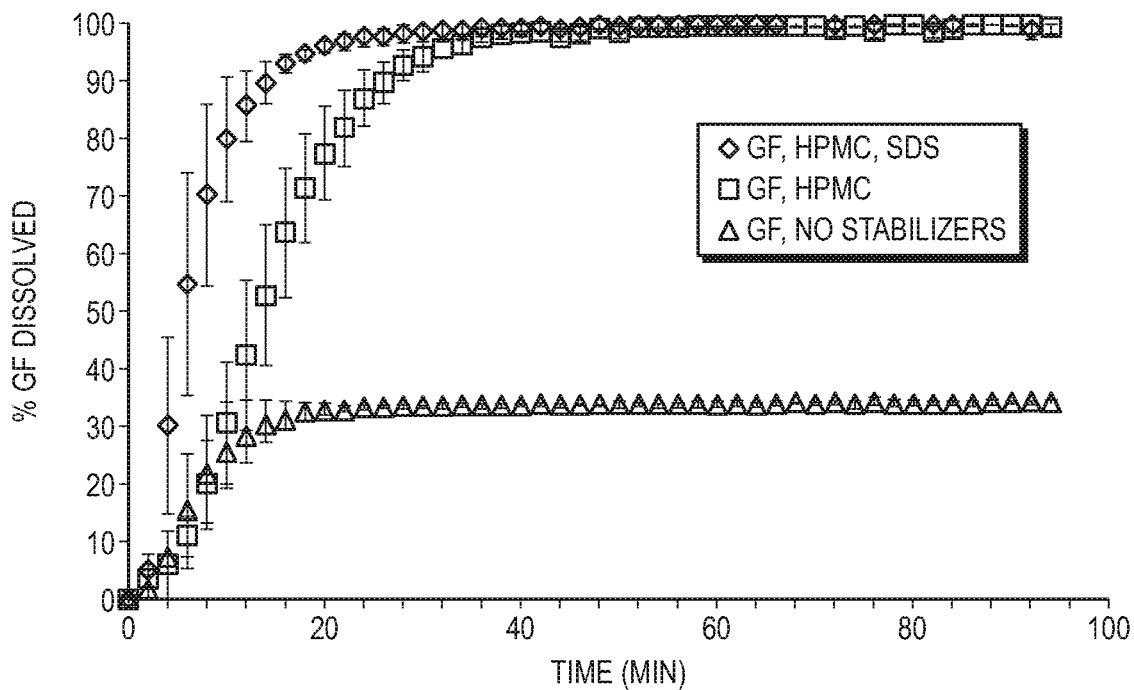
FIG. 6 shows dissolution profiles of different milled formulations of GF from strip films (see also Table 4)

Overall, the mixing step during the film formation process helped to improve the stability of the suspensions that were found to be unstable after milling. Subsequently, the drug nanoparticles were recovered from the films after dispersion of the films in de-ionized water via gentle stirring in 5 min. Slight growth after re-dispersion was observed for FNB films without stabilizers. However, for the rest of formulations the size of drug particles after re-dispersion was similar to the suspension size obtained after mixing with the polymer solution. The re-dispersion results of GF from films (Table 4) correlated well with dissolution of GF from films as seen in FIG. 6. The fastest dissolution of GF was observed from films made from GF/HPMC/SDS precursor suspension followed by GF/HPMC and GF/no stabilizers. Films containing GF/HPMC/SDS and GF/HPMC recovered nanoparticles (Table 4) and were able to reach 100% dissolution in about 20 and 32 min, respectively (FIG. 6).

However, GF nanoparticle aggregates could not be broken completely as observed in the re-dispersion test when formulated without stabilizers and hence, led to poor dissolution from films. These results show that: 1) An unstable milled suspension can be slightly stabilized after mixing with HPMC/Glycerin solution, although better stabilization came when a surfactant was used, and 2) stable film precursor suspensions led to fast recovery and dissolution of drug nanoparticles from films. Such fast dissolution from BCS Class II drugs, in particular when the drug suspensions are well-stabilized, shows an advantage of the present disclosure.

Dry milled fenofibrate powders, produced using a fluid energy mills described before were used for making films. As an example, 2.5 grams of silica coated dry FNB particles were mixed thoroughly with 0.3 grams of sodium dodecyl sulfate (SDS, Sigma Aldrich, Bellefonte, Pa., USA), and added to 50 grams of aqueous Hydroxypropyl methyl cellulose (HPMC-E15LV, Dow Chemicals, Midland, Mich., USA) solution and glycerin. The final weight percent of individual components were 8% HPMC, 5.2% glycerin, 24% of silica coated FNB and 0.6% SDS. The silica coating helped to improve the distribution of the hydrophobic API in the polymer matrix. Mixing was performed by a standard impeller (VWR VOS 16 Overhead Stirrer, VWR catalog number 33998-454, VWR International) at 125 rpm's for 3 hours.

After proper mixing and resting overnight to ensure there were no air bubbles, the suspension was cast at an initial wet film thickness of 1000 microns. The film was dried at a temperature of 40° C. The API loading of these dry films were made at amounts of 8, 15, and 24% by weight by altering the initial amount of dry powder added to the polymer suspension. The primary methods of studying the effectiveness of these films as an oral solid dosage form involve measuring the dissolution rate of the API in a dissolution media.

The dissolution experiments were performed by cutting out a ⅜ inch diameter sample of film and placing it into a flow-though cell dissolution apparatus (USP IV, Sotax, Switzerland) while 118 mL (5.4 mg/mL) aqueous SDS passed through cells (internal diameter of 22.6 mm) at a rate of 16 mL per minute. The amount of API dissolved from the film was measured over time until 100% of drug was released. Content uniformity was performed by cutting out an identical sample of the film, placing it in 100 mL of aqueous SDS, and stirring in a magnetic stirrer for an hour.

Figure 7:
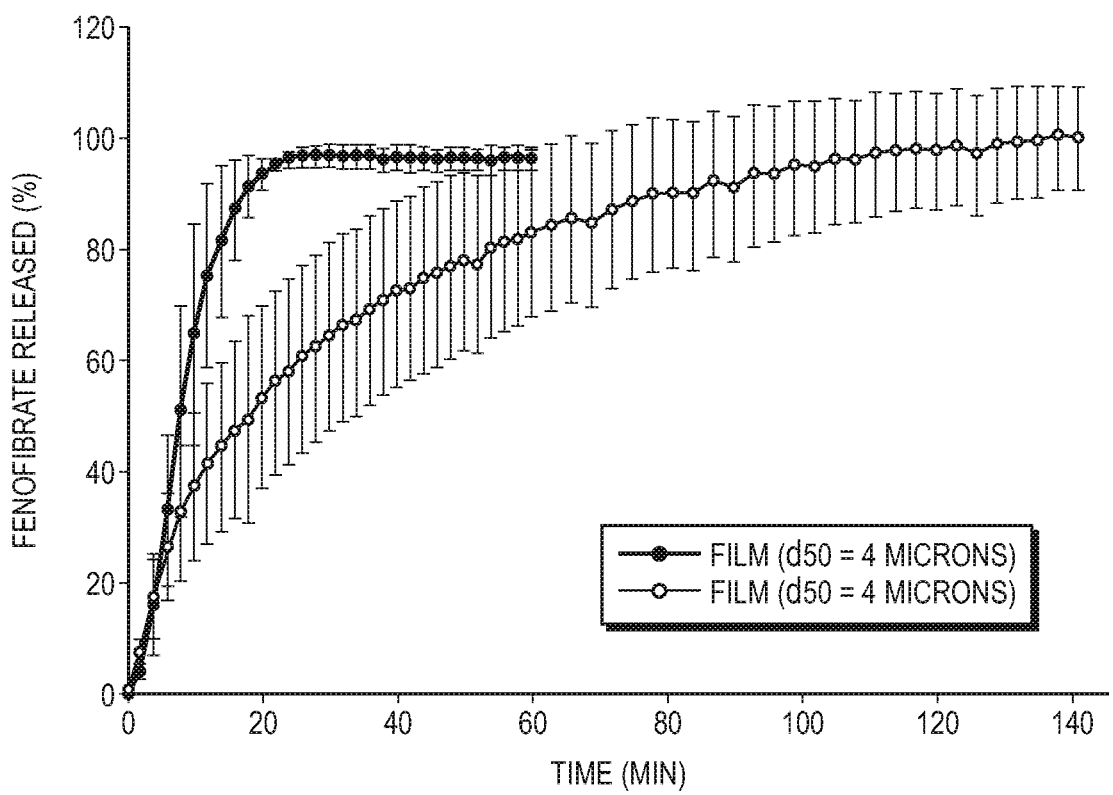
FIG. 7 shows dissolution profiles of silica-coated FNB microparticles from strip-films and an equivalent tablet.

The maximum amount of FNB contained in the film sample was quantified using UV spectrophotometer by measuring the absorbance at 290 nm. FIG. 7 shows the comparison of dissolution profiles of FNB loaded in HPMC films with a commercial FNB tablet. The dissolution rate of FNB from strip-film is seen to be faster than that of a tablet.

TABLE 4

Particle size statistics of the drug suspensions after milling, after mixing with polymer solution and after re-dispersion from films.

| Formulation | After milling | | | After mixing | | | Redispersion from films | | |
|---|---|---|---|---|---|---|---|---|---|
| | D10 | D50 | D90 | D10 | D50 | D90 | D10 | D50 | D90 |
| 10% GF, No stabilizers | 0.18 | 4.0 | 8.6 | 0.24 | 1.8 | 4.5 | 0.18 | 1.8 | 4.0 |
| 10% GF, 2.5% HPMC | 0.22 | 2.6 | 6.6 | 0.23 | 0.39 | 1.2 | 0.17 | 0.42 | 5.2 |
| 10% GF, 2.5% HPMC, 0.5% SDS | 0.11 | 0.16 | 0.24 | 0.08 | 0.18 | 0.35 | 0.11 | 0.17 | 0.29 |
| 10% NPX, No stabilizers | 6.0 | 12.3 | 34.7 | 0.19 | 0.43 | 1.8 | 0.23 | 0.62 | 2.0 |
| 10% NPX, 2.5% HPMC | 0.07 | 0.14 | 0.37 | 0.07 | 0.14 | 0.31 | 0.07 | 0.13 | 0.35 |
| 10% NPX, 2.5% HPMC, 0.5% SDS | 0.07 | 0.14 | 0.27 | 0.07 | 0.15 | 0.35 | 0.07 | 0.14 | 0.37 |
| 10% FNB, No stabilizers | 4.7 | 10.8 | 20.7 | 2.2 | 3.7 | 7.4 | 2.8 | 6.2 | 15.6 |
| 10% FNB, 2.5% HPMC | 0.11 | 0.21 | 0.34 | 0.09 | 0.18 | 0.37 | 0.15 | 0.28 | 0.69 |
| 10% FNB, 2.5% HPMC, 0.075% SDS | 0.12 | 0.22 | 0.34 | 0.12 | 0.19 | 0.31 | 0.12 | 0.26 | 0.65 |

Incorporation of Dry Milled Drug Powders in Films:

Another advantageous aspect of embodiments of the present disclosure is a format allowing for easy incorporation of micronized drug powders in oral dosage, without the associated disadvantages of tableting where fine powders pose flow and segregation issues, often requiring granulation leading to added multiple steps.

Figure 8:
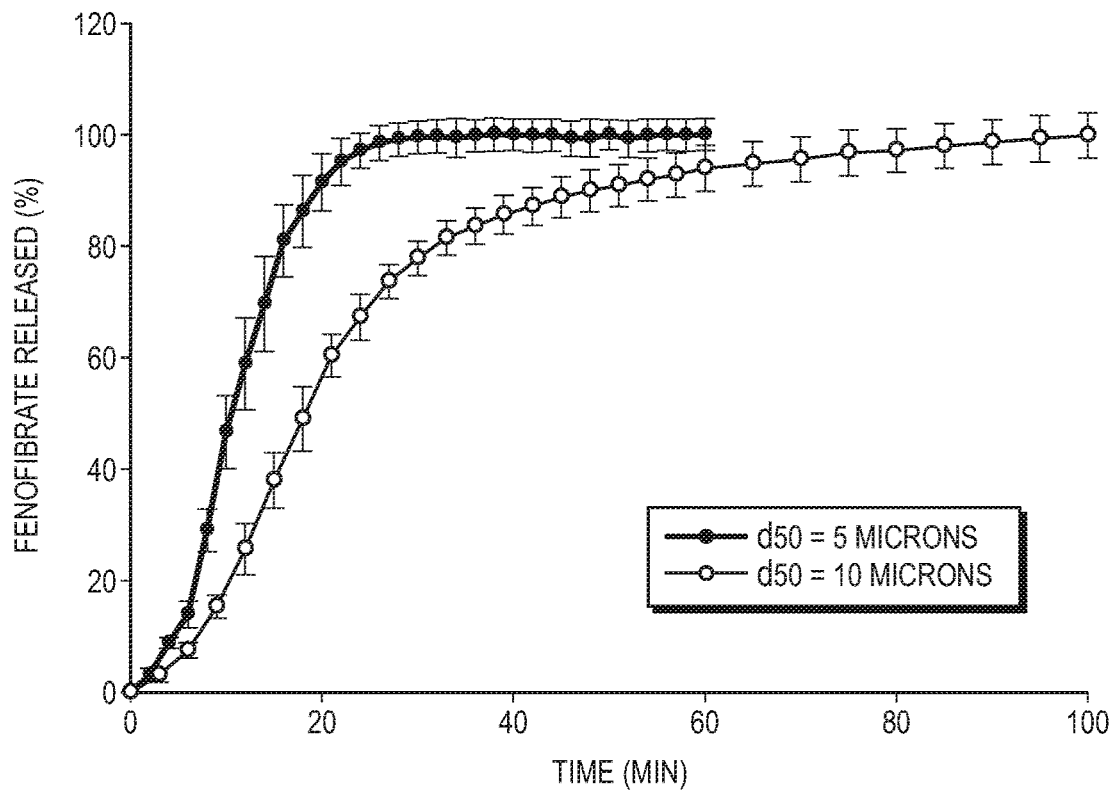
FIG. 8 shows the impact of median particle size of dry-milled API powders on the dissolution rate from films.

FIG. 8 shows the dissolution rate for two silica coated FNB particles that have median particle sizes of 10 and 5 microns. FIG. 8 shows the difference between using as-received FNB particles that are mixed with silica, and particles that are FEM milled down to half the original size (d50=5 microns); showing that for drug size in this range, the dissolution rate is impacted by the particle size, and thus size may be used to control the dissolution behavior.

Figure 9:
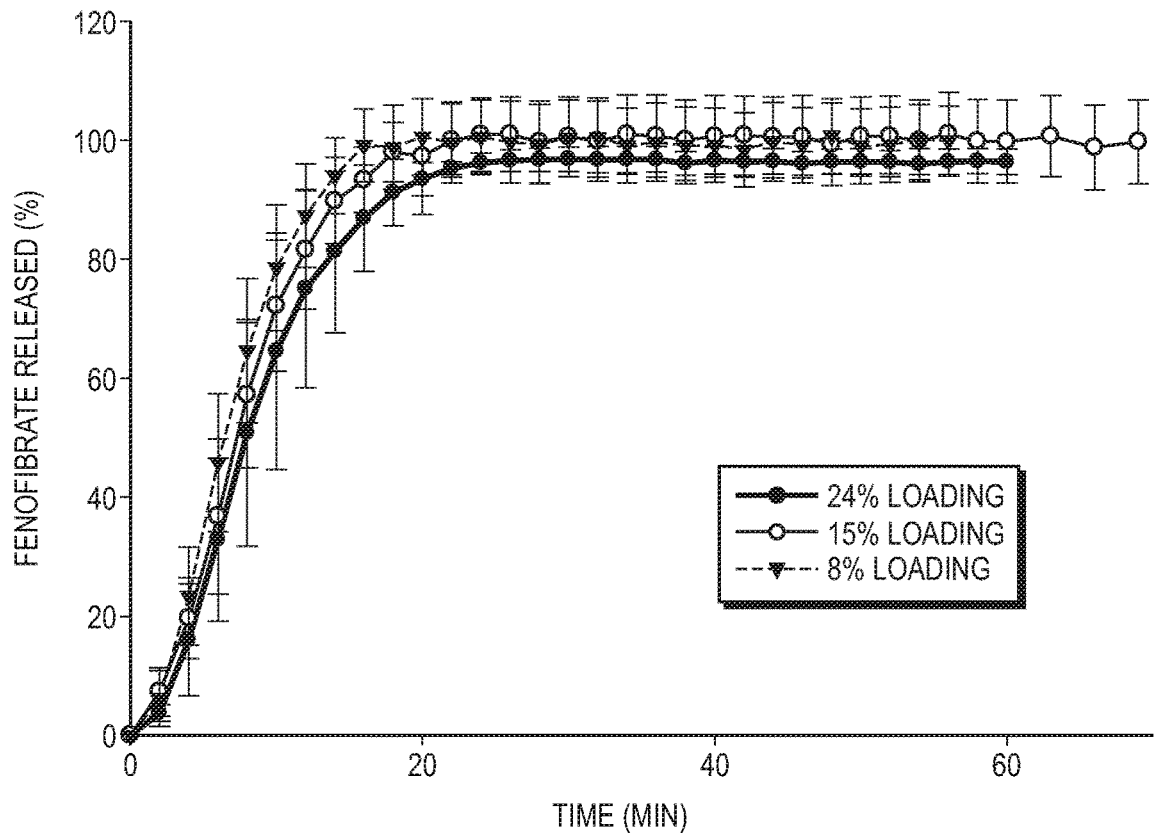
FIG. 9 shows the impact of drug loading of dry-milled API powders on the dissolution rate from films.

FIG. 9 shows the influence of the drug loading on the dissolution rate, where in all cases, particle size is the same, indicating that dissolution is not impacted by the drug loading, making this a robust platform. In all these examples, drug particles have about 100% silica coverage, and each Figure shows an average of 6 film samples.

Incorporation of Liquid Antisolvent (LAS) Precipitated Drug Suspensions in Films:

In a further exemplary embodiment, the incorporation of LAS produced fenofibrate suspensions was utilized as described before. The total drug suspension in the amount of about 320 ml (4 batches of 80 ml) was centrifuged at 20,000 rpm for 0.5 h in a RC28S centrifuge (Sorvall F-28/50 rotor, Dupont Instruments-Sorvall Miami, Fla.). After centrifugation, 280 ml of clear supernatant was discarded, allowing for reduction in significant quantity of organic solvent present after LAS precipitation, and sludge was re-dispersed in the remaining supernatant. This resulted in final drug loading in the concentrated suspension to a high value of 11.2 to about 11.8%, otherwise not possible in a LAS process.

Figure 10:
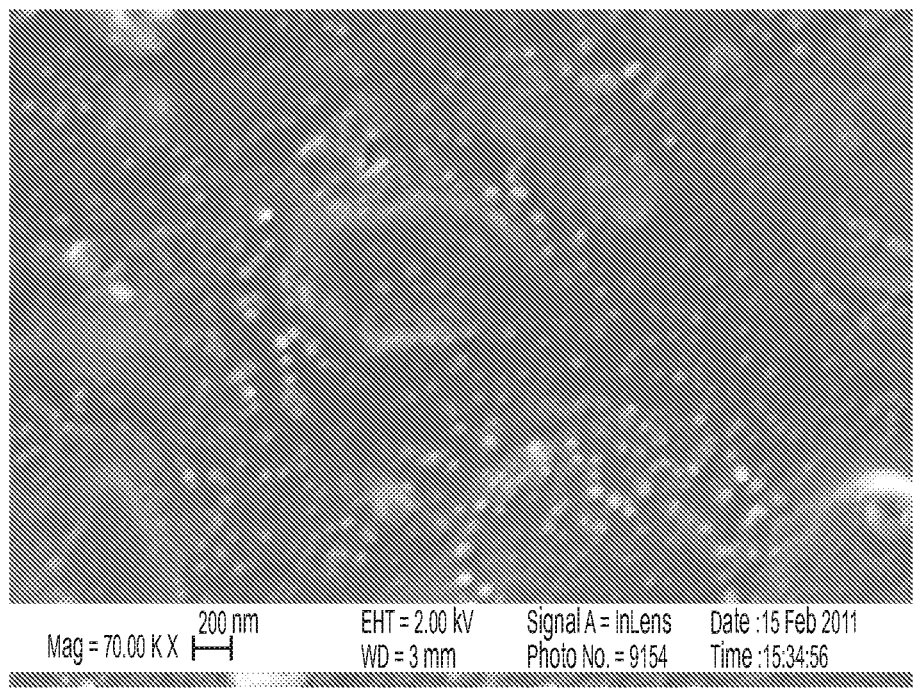
FIG. 10 is a SEM micrograph of fenofibrate particles after centrifugation from the stable suspension produced via the LAS process.
Figure 11A:
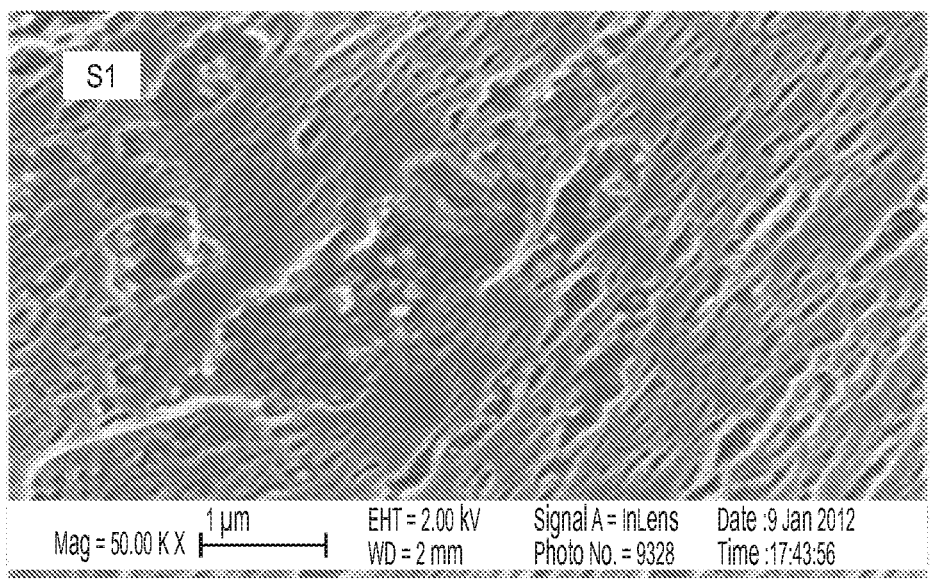
FIGS. 11A-D show SEM micrograph of films produced using four different formulations of fenofibrate particle suspensions produced using LAS process.
Figure 11B:
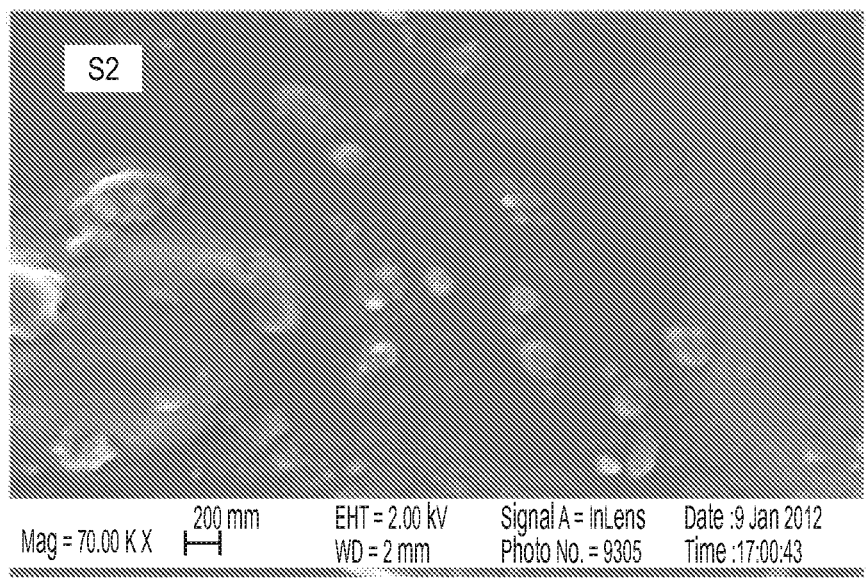
Figure 11C:
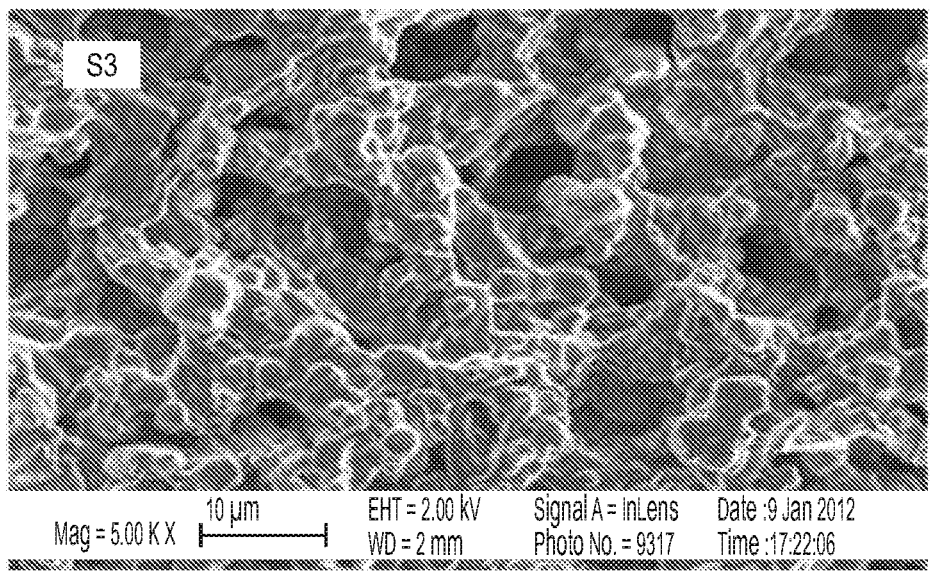
Figure 11D:
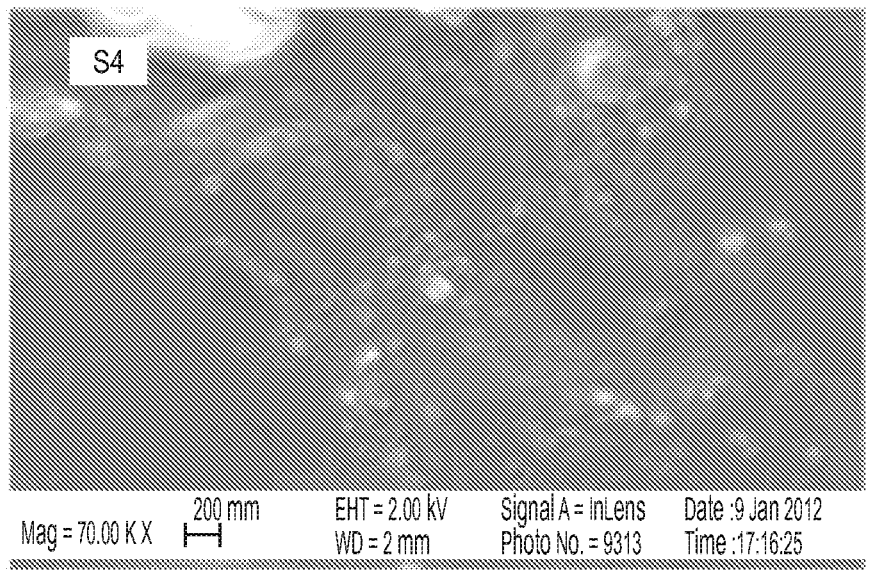

FIG. 10 shows the SEM images of FNB particles after centrifugation, indicating that primary drug nanoparticles are within the size range of 200 nm, although, the PSD ($d_{50}$, $d_{90}$) is within the range of 2-5 μm, as measured by laser diffraction (compare to FIG. 3, which shows particles before centrifugation).

Solutions containing 10% HPMC (grade-E15LV) (S1); 10% HPMC and 10% glycerin (S2); 5% HPMC, 5% sodium alginate and 10% glycerin (S3); 10% sodium alginate and 10% glycerin (S4) were prepared by adding the polymer to water (80 g) and heated to 80° C. All weights are considered w/w wt to solution weight. The prepared polymer solution was then added to the concentrated FNB suspension, mixed for 3 hours using a dual-propeller mixer (McMaster, Catalog no. 3471K5, Los Angeles, Calif., USA) attached to a motor (VWR OVERHEAD STIR VOS 16V120) and left to rest until no bubbles were observed.

The final viscous suspension was then caste onto a stainless steel plate and the film was then dried at 42° C. The theoretical amount of drug in the resulting films accounted for 21 to about 26% (w/w) of the film composition which is significant for a solid dosage form prepared by integration of LASP and polymer film. The average film thickness was between 50 μm to 115 μm.

The morphology of the particles was characterized using a scanning electron microscope (LEO 1530 VP GEMINI, Thornwood, N.Y., USA). FIG. 11 shows SEM micrographs of different film formulations containing FNB particles. Different film morphologies are observed based on the film formulation, and provide different mechanical strengths. Mechanical properties testing were conducted using a TA-XT Plus Texture Analyzer (Stable Microsystems, UK). The sample was attached to the tensile grips and the test was finished once the sample broke. A test speed of 1 mm/s was employed. Tensile strength (TS), elongation at break (E) and Young's modulus (YM) were computed to evaluate the tensile properties of the films.

TS was calculated by dividing the maximum force by the original cross-sectional area of the specimen. YM was calculated as the slope of the linear portion of the stress-strain curve. E was calculated by dividing the extension at the moment of film rupture by the initial length of the specimen and multiplying by 100. The average and standard deviation for three samples were recorded.

Figure 12:
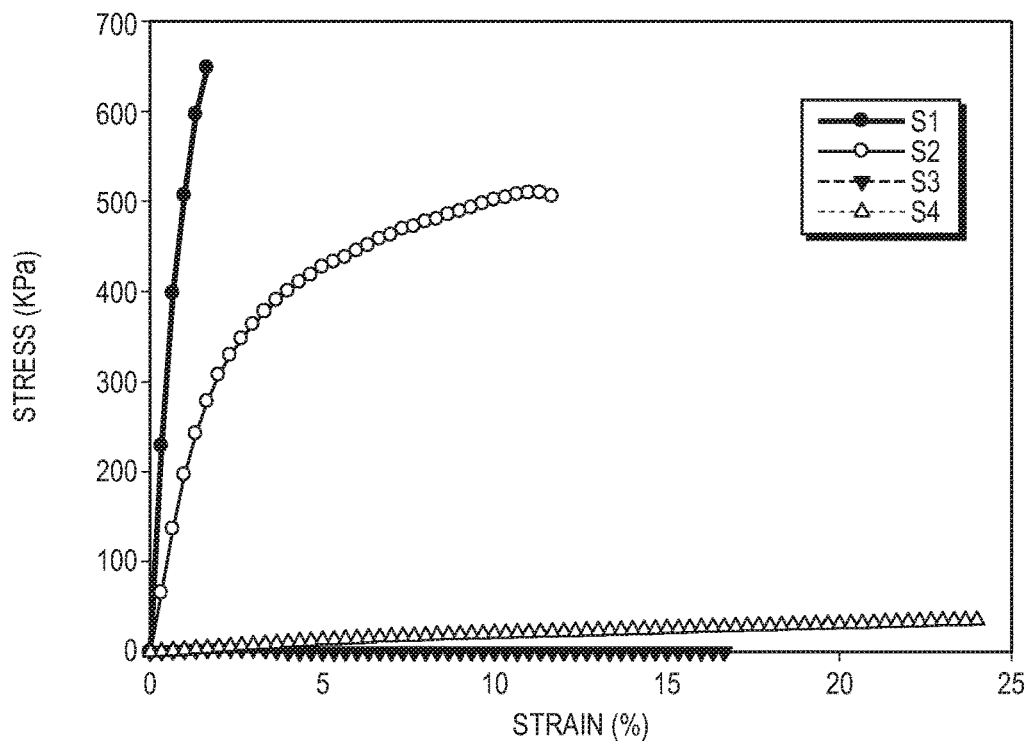
FIG. 12 shows representative stress vs. strain profiles during tension test for the different films containing FNB particles. S1 [FIG. 11A] (HPMC), S2 [FIG. 11B] (HPMC/Glycerin), S3 [FIG. 11C] (HPMC/NaAlg/Glycerin), and S4 [FIG. 11D] (NaAlg/Glycerin)

FIG. 12 shows formulation affects the mechanical strength of the film Films should be strong enough and ductile. A too rigid film may cause an unpleasant sensation in the buccal cavity. The results show that the combination of HPMC and glycerin helped to make strong yet ductile film.

Dissolution experiments were performed using a flow-through cell dissolution apparatus (USP IV, Sotax, Switzerland) with cells of an internal diameter of 22.6 mm. Films were horizontally positioned in the cells with glass beads (1 mm in diameter) filling up the conical part at the bottom of each cell. Glass microfiber filters (GF/D grade, Whatman, Schenectady, N.Y., USA) were used in the filter-head. The temperature was maintained at 37±0.5° C. and a flow rate of 15 mL/min was used. A Thermo Evolution UV spectrophotometer was used to measure the concentration of FNB automatically using a previously made calibration curve.

Figure 13:
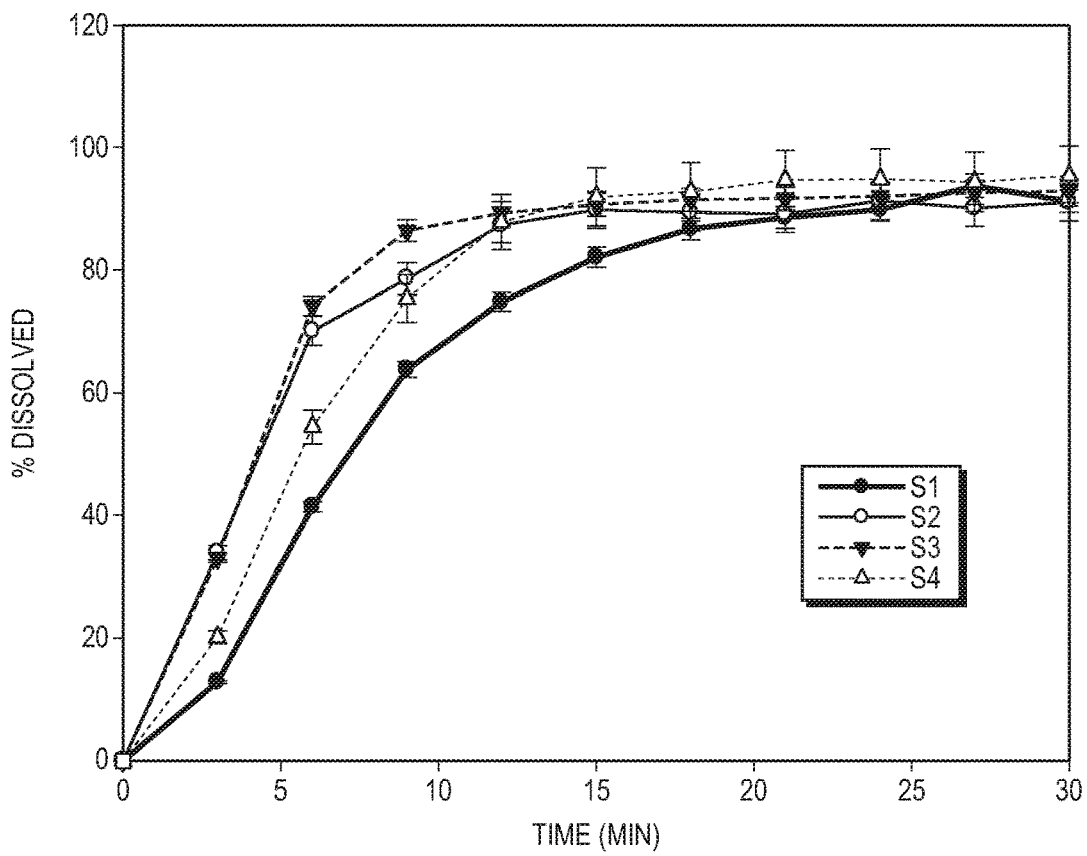
FIG. 13 shows dissolution profiles for the different films containing FNB particles in sds solution. S1 [FIG. 11A] (HPMC), S2 [FIG. 11B] (HPMC/Glycerin), S3 [FIG. 11C] (HPMC/NaAlg/Glycerin), and S4 [FIG. 11D] (NaAlg/Glycerin)

During testing, the dissolution medium (20 mM SDS solution, 100 mL) was circulated by pumping it through each cell. Six samples were used and the average drug release and the standard deviation were plotted as a function of time. FIG. 13 shows the dissolution profiles for different films. The finding shows the combination of HPMC and glycerin leads to faster dissolution of film containing FNB; although all the profiles are comparable to each other, showing again the versatility of this approach of the present disclosure.

Control of Dissolution from Stripfilms:

Advantageous aspects of the present disclosure may be further illustrated through examples of dissolution. In exemplary embodiments, Example 1 below illustrates how dissolution rate changes due to film thickness, when all other parameters, including the film thickness are kept constant. As is known, HPMC may retard the rate of dissolution. This is seen as the dissolution slows down due to the film thickness, although for thinner films, the dissolution is very fast. It is then possible to achieve near instantaneous release if even thinner films are employed consisting of drug nanoparticles; on the other hand, delayed or sustained release may be obtained for thicker films.

In a next example, see Example 2 below, all else, including thickness being equal, the main polymeric ingredient of the film formulation is varied, indicating that dissolution profiles may be tailored using formulation. When combined with Example 1, it is evident that for films that are reasonably thick and made using HPMC and additives, the polymeric film matrix controls the dissolution rate, as long as particle sizes are in the low micron to nano range.

As seen in Example 3 below, irrespective of how the drug was produced, the dissolution profiles are very comparable. In yet another example of the influence of the polymer matrix on the dissolution along with the film-precursor viscosity on drug content uniformity, various viscosity enhancing agents (VEAs) were considered, including use of non-dissolving superdisintegrants, providing a very cost effective alternative. In this Example 4, dissolution is greatly influenced by the type of VEA used. The type of VEA also influences the resulting viscosity values, as well as the achieved RSD values.

In Example 5 below, it is demonstrated that the concepts taught in this disclosure can be applied for continuous manufacturing of strip-films using a commercially available lab-scale (Lab-Cast Model TC-71LC) drying system, albeit such casting systems need to be adapted as required. The example also showed that substrate and film precursor should be compatible so that uniform films can be cast.

In Example 6 below, it is shown that the use of convective drying and high viscosity film-precursors leads to excellent drug content uniformity even for very low dose, down to 1 mg or less. This is a significant advantage of the present disclosure.

Example 7 below demonstrates that using wet stirred media milling that employs finer milling media can produce sub-100 nm griseofulvin drug particles within a reasonable amount of milling time. Using such fine particles, it is shown in Example 8 (below) that use of very fine particles in very thin films made using high viscosity film precursors and convective drying leads to ultra-fast dissolution.

Example 9 below concerns with the mixing of APIs with polymer suspensions and demonstrates that use of high intensity devices like LabRAM providing vibratory mixing leads to very fast mixing time, but may require the use of anti-foaming agents. Films produced in such manner have better properties and dissolve faster than those made using impeller mixing. Example 10 below considers the influence of high-shear mixing on dispersion of nano-particles and demonstrates that it leads to film precursor stabilization, and allows for preparing surfactant-free HPMC strip films containing poorly water soluble drugs, that exhibit dissolution comparable to films containing surfactants.

In Example 11, high-resolution drug distribution imaging was performed using Raman chemical mapping system for films produced with and without using convective drying and high viscosity film precursors. Films formed using high viscosity precursors and convection drying have more uniform distribution of drug within the polymer matrix at a very small scale of scrutiny down to less than 100 microns. This is yet another major advantage of the present disclosure.

The present disclosure will be further described with respect to the following examples; however, the scope of the disclosure is not limited thereby. The following examples illustrate the improved systems/methods of the present disclosure of fabricating advantageous stripfilm based pharmaceutical products. More particularly, the following examples illustrate the advantageous systems/methods of the present disclosure of fabricating stripfilm based pharmaceutical products by utilizing higher viscosity film forming precursors and drying methods that accomplish improved/faster drying and provide improved/excellent content uniformity of active pharmaceutical agents in the fabricated stripfilm based pharmaceutical products.

Example 1: Dissolution Behavior of Griseofulvin Nanoparticles from Polymer Film Matrices: Effect of Film Thickness Aqueous polymer solutions containing low molecular weight hydroxy propyl methyl cellulose (HPMC E15LV (Dow Chemical)), high molecular weight polyvinylpyrrolidione (PVP K90 (Sigma-Aldrich, Saint Louis, Mo.)) and glycerin (Sigma-Aldrich, Saint Louis, Mo.) were prepared as per the protocols described previously.

The resulting polymer solution and griseofulvin (GF) nanosuspensions (10% (w/w)) produced via wet stirred media milling method were added in a 2:1 ratio and mixed for 4 hours using a dual-propeller mixer (McMaster, Catalog no. 3471K5, Los Angeles, Calif., USA) attached to a motor (VWR overhear stir VOS 16V120). The thoroughly mixed high viscous GF-Polymer suspensions (about 8000 CPS) were cast at four different thicknesses (about 200, 400, 600 and 1000 μm) using a doctor blade (Elcometer, USA) and dried in a continuous drier (Lab-Cast Model TC-71LC Tape Caster, HED international, NJ).

The final thickness of films was measured using a digital micrometer (Mitutoyo, Japan) to be 20, 45, 80 and 160 μm, respectively. The final drug (GF) loading in all the films was kept fixed at about 11 wt %; see Table 5 for the film composition, which does not show the final moisture content in a dry film, estimated at about 5%.

The dissolution behavior of the stripfilms made using the blend (HPMC and PVP) strip films containing GF nanoparticles was examined using a flow-through cell dissolution apparatus (USP IV, Sotax, Switzerland) with cells of an internal diameter of 22.6 mm. Six circular film samples (having an area of 0.712 cm$^2$) were punched out of each film and tested. For each film, six samples were horizontally positioned in the six cells with 6.5 g of glass beads (1 mm in diameter) filling up the conical part at the bottom of each cell. Pall HT Tuffryn Membrane Disc Filters (0.2 μm) were used for this study in the filter-head in each experiment. The temperature was maintained at 37±0.5° C., and a flow rate of 16 ml/min was used. During testing, a 100 ml dissolution medium (SDS solution (5.4 mg/ml)) was circulated by pumping it through each cell.

Figure 14:
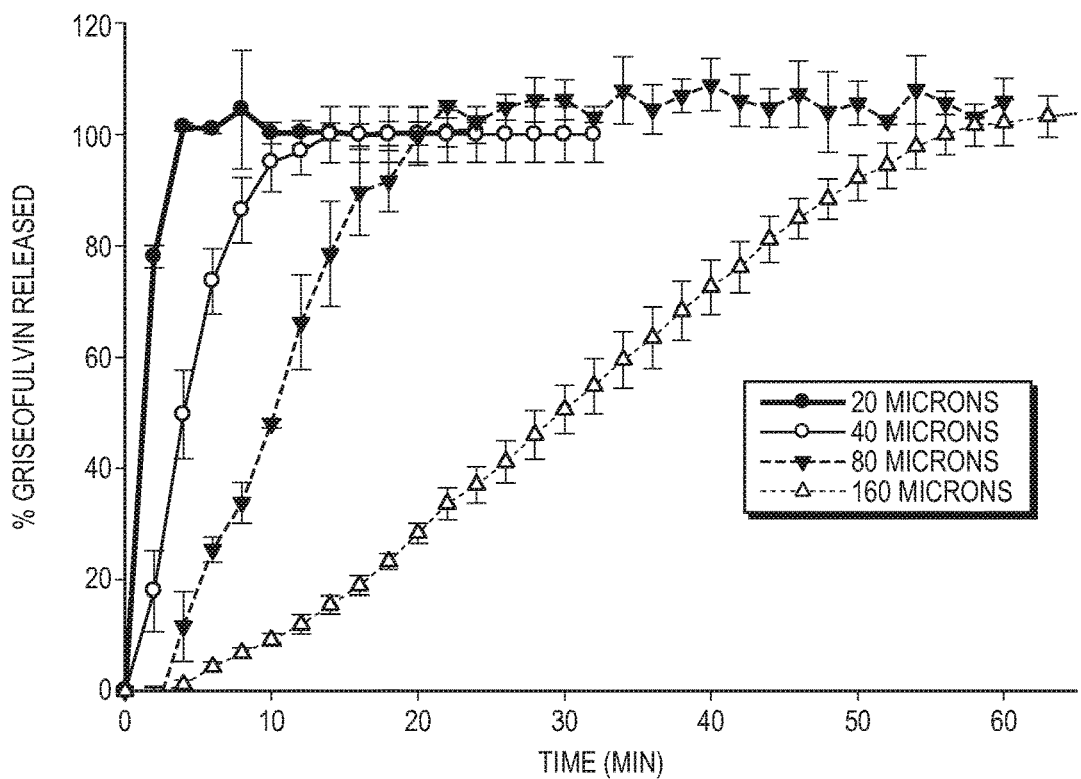
FIG. 14 shows GF release profiles from polymer strip films of varying thickness; all other film formulation and drug particle parameters are the same.

FIG. 14 shows the dissolution profiles for GF release from films of different thickness. Each curve represents an average over six samples. A fast drug release is observed in film with the lowest thickness (20 μm), 80% of the drug is released in two minutes. When the thin film comes in contact with the dissolution media, the film swells and disintegrates instantaneously, thus releasing the API fast.

As the thickness of the film increases, the effect of swelling and subsequent gel-formation imparted by HPMC increases and in conjunction with the high molecular weight PVP, makes it difficult for the polymer network to hydrate and release the GF nanoparticles. This is reflected in the observed delay in drug release (for film with 160 microns thickness). The dissolution behavior is significantly impacted and in fact controlled by film thickness, demonstrating that thickness is a key variable that may allow for developing a wide range of applications based on these films. For example, thin films can be applied for buccal delivery of API; whereas a thick film can be used where extended release is desired.

TABLE 5

| Composition of wet film (wt %) used in Example 1 | | | | |
|---|---|---|---|---|
| HPMC (E15LV) | PVP (K90) | Glycerin | GF | SDS |
| 7.40 | 6.67 | 3.33 | 2.94 | 0.15 |

Example 2: Dissolution Behavior of Griseofulvin Nano Particles from HPMC Strip Films: Effect of Type of Polymer Additive Polymer blend solutions with HPMC (E4M) as the base polymer, and containing different ratios of PVP K-30 (a low MW polymer), sodium alginate (a medium MW polymer) and chitosan (a high MW polymer) were prepared and mixed with GF nano-suspension produced via WSMM in 2:1 ratio using a dual-propeller mixer (see Example 1). Table 6 shows the wet film composition used in this example.

To compare the effect of polymer molecular weight alone, formulation F1 was prepared using low molecular weight HPMC (E15LV). Thoroughly mixed suspensions were cast at a fixed thickness (1000 μm) using a doctor blade (Elcometer, USA) and dried. The final thickness of these films was measured to be 95±5 μm.

Figure 15:
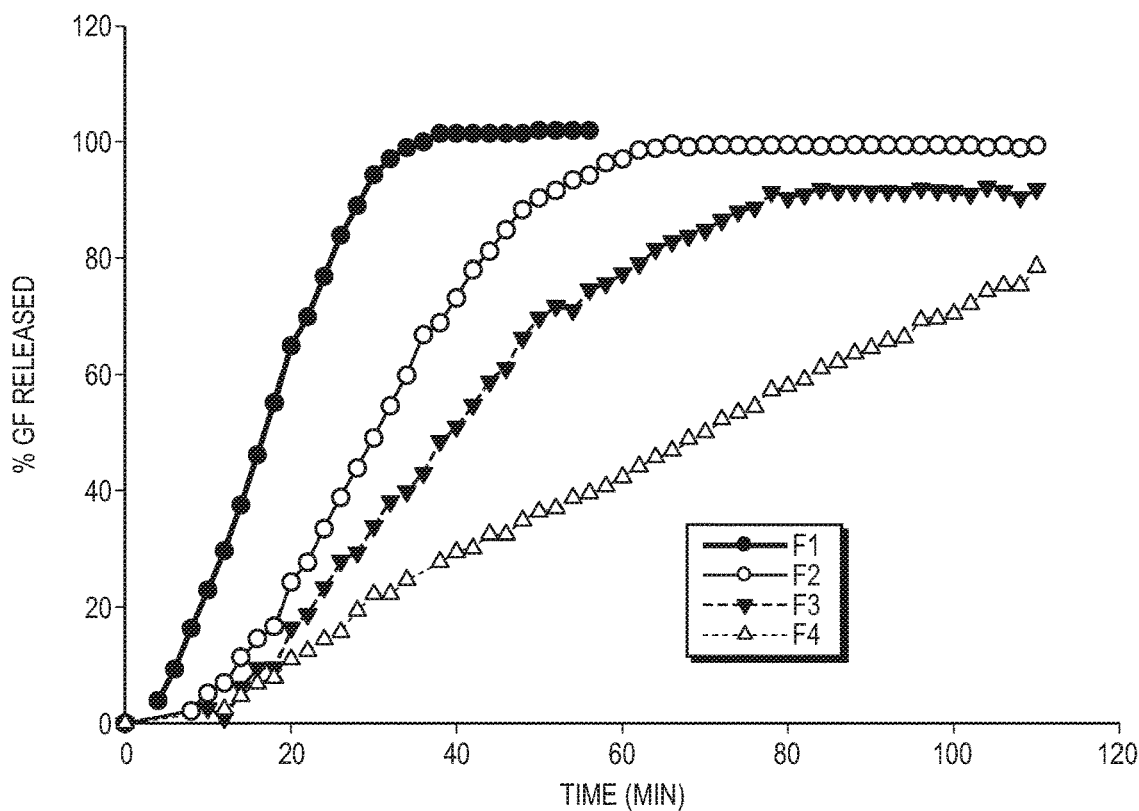
FIG. 15 shows dissolution profiles of GF from HPMC based strip films incorporating various other polymeric additives, see Table 6 for the blend compositions F1-F4.

The drug (GF) loading in all the dry films was kept constant at about 22 wt %. The dissolution analysis of the GF loaded strip films was performed following the protocol described in Example 1. FIG. 15 shows the effect of polymer additive type on API release kinetics. As the polymer molecular weight (MW) increased, so did the dissolution time (as it takes longer for the film to hydrate/saturate followed by relaxation of the polymer network). As expected the addition of SA and PVP lead to faster dissolution time compared to chitosan.

On the other hand, the film made from low MW HPMC (F1) led to very quick release of GF. Thus, by using polymers of varying MW, the dissolution behavior of API can be manipulated to a desired rate. It is noted that for traditional oral dosage forms such as tablets, it is not easy to manipulate dissolution profiles simply by adjusting the excipients as is the case in the stripfilms.

TABLE 6

Wet film composition (wt %) used in this example (in all cases GF was kept fixed at 2.2 wt % and SDS was kept fixed at 0.2 wt %)

| Formulation | HPMC (E15 LV) | HPMC (E4M) | PVP (K30) | SA | Chitosan | Glycerin |
|---|---|---|---|---|---|---|
| F1 | 7.40 | none | none | none | none | 3.33 |
| F2 | none | 2.40 | 2.60 | none | none | 1.87 |
| F3 | none | 2.40 | none | 2.60 | none | 1.87 |
| F4 | none | 2.40 | none | none | 1.12 | 1.87 |

Example 3: Dissolution Behavior of Fenofibrate Nano/Micro Particles from HPMC Strip Films: Effect of Particle Formation Method HPMC based strip films (95±5 nm) containing fenofibrate (FNB) nano (prepared via WSMM) and micro particles (prepared via LASP and FEM) were prepared using a protocol described previously. The formulations from all the three methods were kept as similar as possible for the sake of fair comparison. The final drug (FNB) loading in all the films (dry) was kept fixed at about 28 wt %. The dissolution of the FNB loaded strip films was carried out in accordance with protocols described in Example 1.

Figure 16:
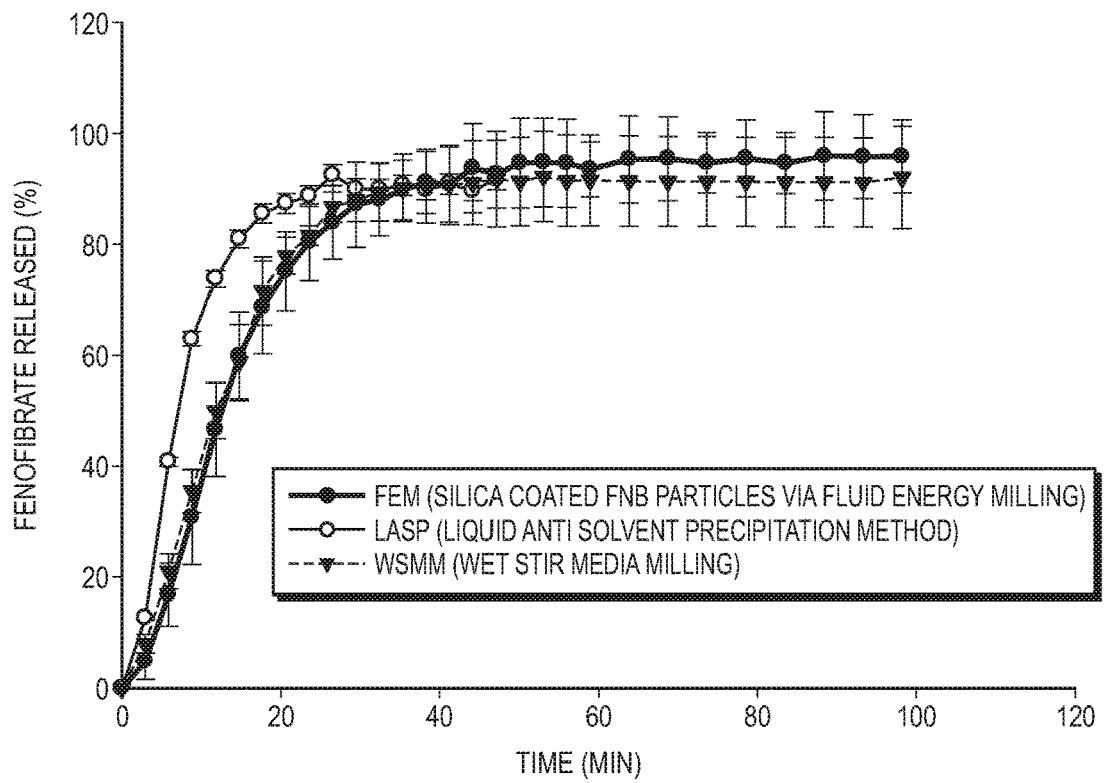
FIG. 16 shows dissolution profiles of FNB from strip films containing nano/micro particles produced via FEM, LASP and WSMM; see Table 7 for the film composition.

Table 7 provides the formulation details of the wet films. FIG. 16 shows the dissolution profiles for FNB nano/microparticles from strip films (each curve represents an average of six samples). As seen from FIG. 16, there is no statistically significant difference between these release profiles. Irrespective of the particle formation technique used or the particle size (from over 150 nm to up to 3 microns), the time taken for 100% drug release is nearly same and shows very fast release for a poorly water soluble drug, here, implying that at such fine particle size, the dissolution is rate limited by the polymer matrix. HPMC based films typically do not disintegrate instantaneously; they swell upon contact with dissolution media and gradually erode away. Consequently, at such thickness values and the range of particle sizes considered, the effect of API size on dissolution is masked.

TABLE 7

Wet film composition used in Example 3 (wt %).

| | HPMC (E15LV) | Glycerin | API (FNB) | Surfactant |
|---|---|---|---|---|
| FEM | 8 | 5.2 | 4.5 | SDS-0.6 |
| LASP | 6.2 | 5.0 | 4.5 | Pluronic-0.8 |
| WSMM | 6.2 | 5.0 | 4.5 | SDS-0.22 |

Example 4: Influence of Viscosity Enhancements: Superdisintegrants as Viscosity Enhancing Agents (VEAs)

Some important parameters which can significantly influence the final content uniformity of API in films is the starting precursor viscosity, hence, viscosity enhancing agents (VEA), also known as gelling agents or film modifiers can be integral part in the film formation design. These additives, when added in small amounts, help increase the viscosity of suspensions, thus decreasing the thickness variations during casting and potentially maintaining API content uniformity across the films.

It is known that the use of high molecular weight polymers or natural gums may be used as VEAs. However, most recommended VEAs are relatively expensive and may not provide the drug content uniformity when the APIs are in form of nano or micro particles. Therefore, in this disclosure, use of superdisintegrants (SDIs), which are commonly used in tablets for fast disintegration and dissolution of API, is considered. The SDIs swell when in contact with water, thus aiding in quick disintegration and dissolution of granular material. The impact of SDI incorporation in films was not previously investigated to examine the impact of incorporating both nanoparticles and SDI in polymer strip films. Without being bound by any theory, it is hypothesized that due to the high swelling capacity of SDIs, their addition to the precursor polymer solution can significantly enhance the viscosity of the solution and may promote dissolution. In this example, it is demonstrated that SDIs act as VEAs and perform better than traditional VEAs like guar gum, xanthan gum and pectin, which are frequently used but do not have the cost benefit.

In this example, small amounts of traditionally used VEAs like guar gum, xanthan gum, pectin and non-traditional VEAs (SDIs) like SSG, CCS and kollidon (1% (w/w)) were added to HPMC suspensions followed by addition of GF nanoparticles in suspension form; see Table 8 for their formulation details. Aqueous polymer solutions containing low molecular weight hydroxy propyl methyl cellulose (HPMC E15LV), VEA and glycerin (Table 8) were prepared by adding weighed amounts of HPMC, VEA and glycerin to water (on w/w basis) at 90° C. The solutions were allowed to cool down to room temperature while being stirred continuously overnight to diffuse out the air bubbles completely.

At least two noted issues arose during the addition of pectin, guar gum and xanthan gum: (1) the addition of these components led to severe bubble formation within the HPMC suspensions, and (2) addition of xanthan gum led to clump formation and xanthan gum exhibited the tendency to separate from HPMC in the solution. Surprisingly, the addition of SDIs did not lead to any bubble formation or clumping, as they were well dispersed in the HPMC solution, indicating their advantageous use in the present disclosure as VEAs. The HPMC-VEA suspensions were then mixed with griseofulvin (GF) nanosuspension produced via a wet stirred media milling method in a 2:1 ratio in a manner previously described. The thoroughly mixed high viscous HPMC-VEA-GF suspensions were then cast at a fixed thickness of 1000 µm and dried.

The final thickness of films was measured to be 100±5 µm respectively. The final drug (GF) loading in all the films was kept fixed at about 14 wt %. In order to inspect the effect of VEA on viscosity of suspensions, the viscosity of HPMC-VEA solutions before and after the addition of GF nanosuspensions were measured using a R/S plus Rheometer (Brookfield Engineering, Middleboro, Mass., USA). The Rheometer was equipped with a shear rate controlled coaxial cylinder (CC40), and a water jacket assembly Lauda Eco (Lauda-Brinkmann LP, Delran, N.J., USA). The temperature of the jacket was kept constant at 25±0.5° C. The suspensions were subjected to a low shear rate and the viscosity at a fixed low shear value of 2.2 s$^{-1}$ were measured in triplicates to check for reproducibility.

As seen from Table 8, the addition of VEAs increases the viscosity of suspensions greatly with SSG and xanthan gum causing a significant increase in viscosity of film precursors; however, kollidon did not result in increased viscosity. Higher viscosities lead to good control over the casting process, thus reducing the variations in film thickness and subsequently the content uniformity of films. The thickness variation in final dried films (in all cases S1-S6) was observed to be within 5% RSD; see Table 9.

In exemplary embodiments, the gums allow for forming uniform thickness films but as will be seen next, that does not necessarily translate into improved drug content uniformity, which was based on an assay analysis that was carried out by dissolving samples (10 samples, each of area about 0.712 cm$^2$) from a single film in 250 ml SDS (5.4 g/l) media. It was observed that the films containing SSG, CCS and kollidon had better CU than pectin or gums. Surprisingly, the % RSD of APIs over ten samples was less than 5% for films containing SDIs, whereas the % RSD for films containing pectin, guar and xanthan gum was greater than 10% RSD as shown in Table 9. SSG produced the best CU results, exhibiting less than 3% RSD values, affording a cost-effective, novel solution to improved CU in strip-films containing drug particles.

The dissolution behavior of strip films containing GF nanoparticles was examined using a flow-through cell dissolution apparatus (USP IV, Sotax, Switzerland) with cells of an internal diameter of 22.6 mm. Six circular film samples (having an area of 0.712 cm$^2$) were punched out of each film and tested. For each film, six samples were horizontally positioned in the six different cells with 6.5 g of glass beads (1 mm in diameter) filling up the conical part at the bottom of each cell. Pall HT Tuffryn Membrane Disc Filters (0.2 µm) were used for this study in the filter-head in each experiment. The temperature was maintained at 37±0.5° C., and a flow rate of 16 ml/min was used. During testing, a 100 ml dissolution medium (SDS solution (5.4 mg/ml)) was circulated by pumping it through each cell.

Figure 17:
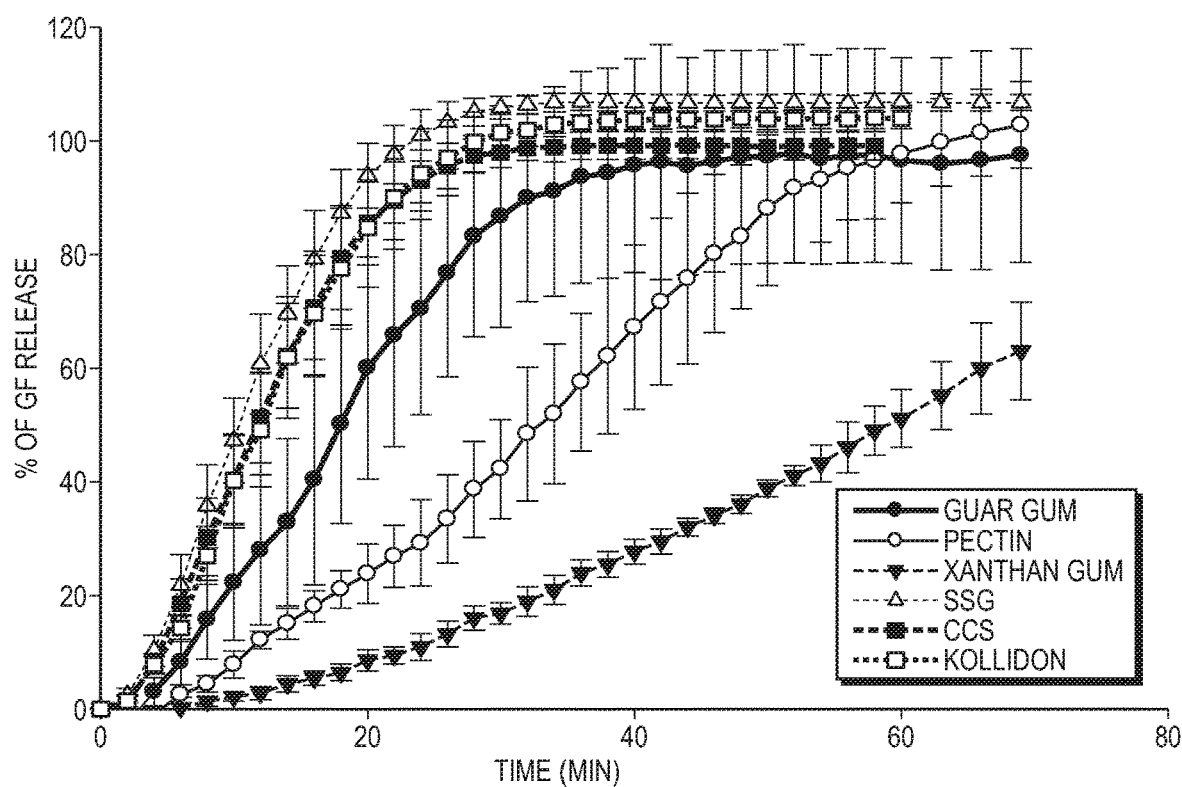
FIG. 17 shows dissolution profiles from various viscosity enhancing agents, including superdisintegrants used in an innovative way (see Table 8 for their formulations)

FIG. 17 shows the dissolution profiles for GF release for formulations S1-S6. Each curve represents an average over six samples. It is interesting to note that the addition of SSG, CCS or kollidon, which helped increase viscosity, did not adversely impact the dissolution kinetics of the HPMC film, whereas the addition of pectin, guar and xanthan gum altered the dissolution behavior of strip films drastically. This is a major disadvantage of traditional VEAs, because in addition to slowing down the dissolution rate, they did not enhance the drug content uniformity.

TABLE 8

Viscosities of HPMC solutions containing SDIs and traditional VEAs (fixed composition of HPMC: 8.5% (w/w), glycerin: 3.33 wt %, VEA: 1.1 wt %, GF: 2.94 wt %, SDS 0.15 wt % was used) recorded at a low shear rate value of 2.2 s$^{-1}$ (average and standard deviation over six runs is presented):

| Formulation | Additive | Viscosity of formulation (cP) before addition of GF nanosuspension | Viscosity of formulation (cP) after addition of GF nanosuspension |
|---|---|---|---|
| S | No additive | 5000 ± 300 | 2500 ± 200 |
| S1 | SSG | 20954 ± 847 | 11764 ± 300 |
| S2 | CCS | 15000 ± 400 | 5371 ± 250 |
| S3 | CP | 8112 ± 216 | 2357 ± 210 |
| S4 | Pectin | 14741 ± 561 | 4274 ± 333 |
| S5 | Guar gum | 9790 ± 589 | 3320 ± 273 |
| S6 | Xanthan gum | 23288 ± 499 | 12381 ± 392 |

TABLE 9

Film thickness, drug content, and their respective RSD values for the films based on the formulation of Table 8:

| Formulation | Additive | Thickness (µm) | % RSD | Mass of Drug in film (mg) | % RSD |
|---|---|---|---|---|---|
| S | No additive | 98.0 ± 6.0 | 6.0% | 1.47 ± 0.16 | 10.5% |
| S1 | SSG | 100.0 ± 3.0 | 3.0% | 1.51 ± 0.04 | 2.70% |
| S2 | CCS | 100.0 ± 5.0 | 5.0% | 1.52 ± 0.07 | 4.60% |
| S3 | CP | 100.0 ± 5.0 | 5.0% | 1.48 ± 0.09 | 6.15% |
| S4 | Pectin | 102.5 ± 1.4 | 1.8% | 1.60 ± 0.12 | 7.5% |
| S5 | Guar gum | 100.5 ± 1.4 | 1.4% | 1.47 ± 0.13 | 8.84% |
| S6 | Xanthan gum | 100.5 ± 1.4 | 1.4% | 1.49 ± 0.12 | 8.10% |

Example 5: Continuous Manufacture of Strip-Films Using a Lab-Scale (Lab-Cast Model TC-71LC) Drying System In the present example, a gentle drying method using a commercially available drying unit (Lab-Cast Model TC-71LC Tape Caster, HED International, NJ) is demonstrated. This unit is capable of drying films in less than one hour, and even in as little as about 10 minutes, while preserving film homogeneity for well-designed formulations. The continuous dryer had an overall length of 2.95 m, a casting length of 2.13 m, and consisted of three distinct drying zones, see, e.g., FIG. 18.

Figure 18A:
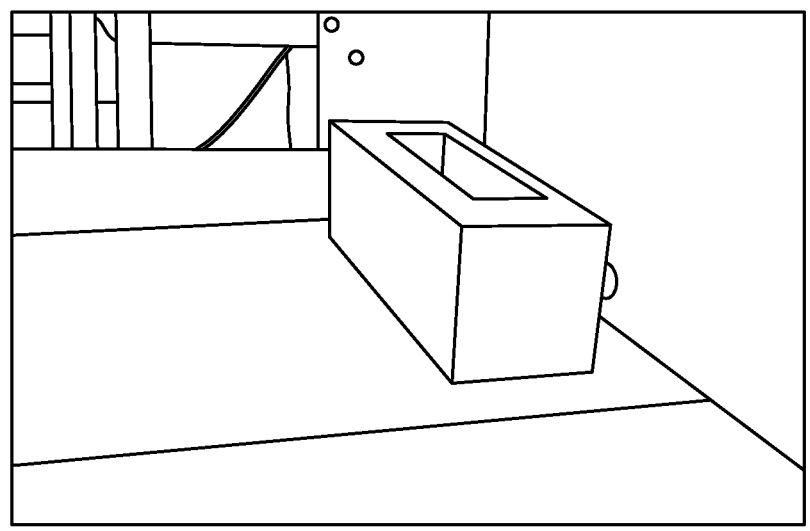
FIG. 18A shows a doctor blade film caster over the film carrier substrate.
Figure 18B:
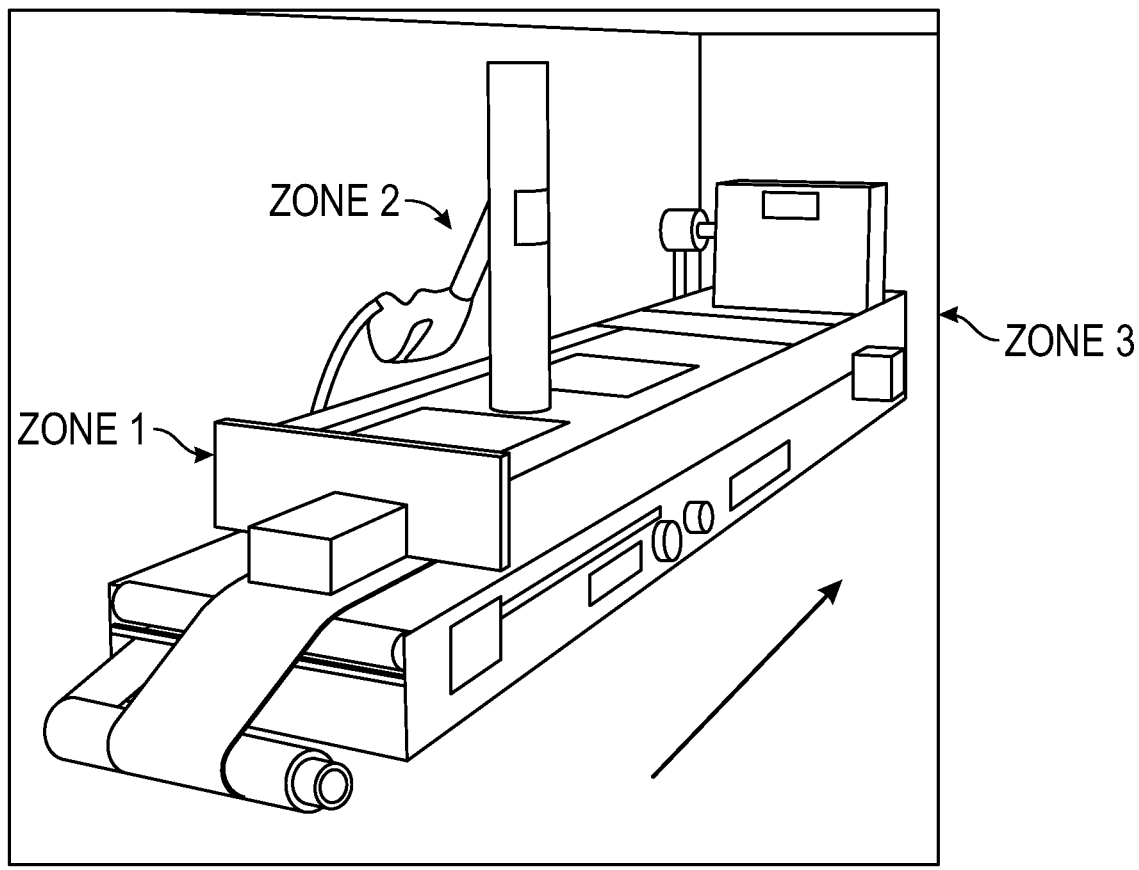
FIG. 18B shows a Lab-Cast Model TC-71LC Tape Caster, HED International; showing various elements, three zone heating, and the arrow depicting the direction in which the substrate moves.

The polymer-API mixture was cast onto a 15 cm wide Mylar belt substrate above a granite surface plate with a controlled thickness by a doctor blade just outside of Zone 1, see FIG. 18. The wet film was pulled through the dryer by the Mylar belt at a designated speed between 5 and 50 cm/min. The film passed over an aluminum plate heated by electric resistance heaters at a specified temperature, heating the film via conduction as it passed through Zone 1.

In Zone 2, the film became exposed to counter-flowing hot air at a specified air speed and temperature, drying it from above via convection, while simultaneously being heated from below at the same temperature. The air was warmed by a 3 kW heater situated at the end of the dryer and pulled through Zones 2 and 3 by a manually adjustable exhaust fan located between Zones 1 and 2.

In Zone 3, the film was heated only by blowing hot air via convection. The temperature of each zone can be adjusted independently between about 20 to about 90° C. The resulting dry film was peeled from the Mylar substrate as it exited the dryer beyond Zone 3. All three zones were covered with removable tempered glass viewports, which allowed for direct observation of the drying process and access to the product, as well as the option for in-line sensing such as NIR and Raman.

Films produced on the continuous dryer, which incorporated both conductive heating from below and convective heating from above, exhibited neither skin formation nor ripple formation, nor any other visible imperfections, such as wrinkles or blisters. The film quality improved also when the cast film-precursor interacted favorably with the substrate to avoid width-wise film shrinkage.

The best results were achieved with a combination of HPMC, PVP and glycerin, while significant shrinkage was observed without PVP, despite its ability to produce high quality films when dried on a stainless steel substrate instead of Mylar substrate (Table 10). On the other hand, thinner films allowed better control even without the use of PVP; for example, reducing the thickness of the 15% HPMC, 5% glycerin formulation from 400 μm to 200 μm (in a wet film) eliminated the shrinkage effect. Based on these results, the use of film-forming solution with a viscosity of 5000 CPS or greater is recommended for this process.

TABLE 10

Film quality as a function of formulation (without API, except for those marked with a * that were also prepared both with and without API) and thickness, cast using Lab-Cast Model TC-71LC Tape Caster on a Mylar substrate:

| Polymer formulation (% w/w) | Thickness (μm) | Viscosity (CPS) | Film quality |
| --- | --- | --- | --- |
| 10% HPMC, 10% PVP [K-90], 5% glycerin | 400, 800, 1600 | 14000 | excellent* |
| 15% HPMC, 5% glycerin | 400 | 18900 | Good |
| 15% HPMC, 5% glycerin | 200 | 18900 | Good |
| 10% HPMC, 3.3% glycerin | 200 | 4000 | bad |
| 15% HPMC, 5% triacetin | 200 | 17600 | Good* |
| 15% HPMC, 5% Polypropylene glycol | 200 | 19700 | Good* |
| 11.7% HPMC, 3.9% glycerin | 200 | 6100 | Good |

Example 6: Evaluation of the Drug Content Uniformity from Films Formed Using Convective Drying and High Viscosity Film-Precursors The HPMC-PVP-GF suspensions were cast at three different thicknesses (400, 600 and 1000 μm) using a doctor blade, and dried in a convective drying system. The final thickness of dried films was measured using a digital micrometer (Mitutoyo, Japan) and found to be about 45, 80 and 160 μm, respectively. The final dimensions of final film were 14 cm×7 cm.

Figure 19:
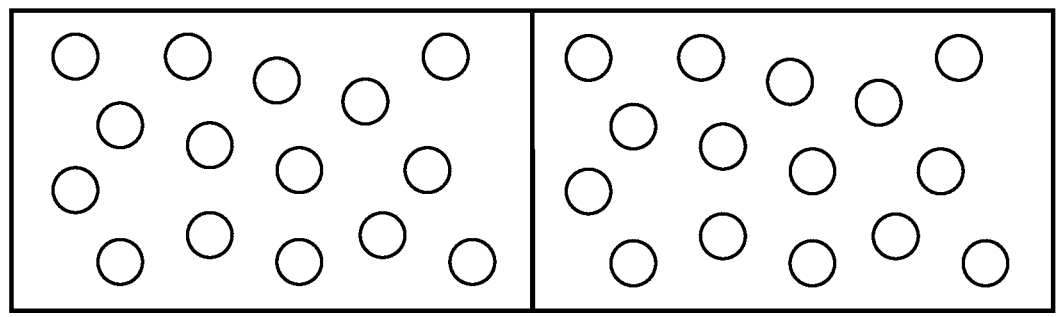
FIG. 19 shows a schematic of film sampling for the purpose of drug content uniformity evaluation. Holes are cut using a circular ⅜" diameter punch.

To test for content uniformity of the film, at least 20 circular samples ⅜" in diameter were punched from each film (see schematic in FIG. 19), and dissolved in 100 mL of 5.4 mg/mL SDS. The concentrations of the resulting samples were measured using UV spectrophotometry. The final drug (GF) loading in all the films was found to be about 11 wt %. Good/improved content uniformity was observed in all three cases, even for thin films with very small drug dose (see Table 11), illustrating an advantageous outcome of the present disclosure.

Figure 20:
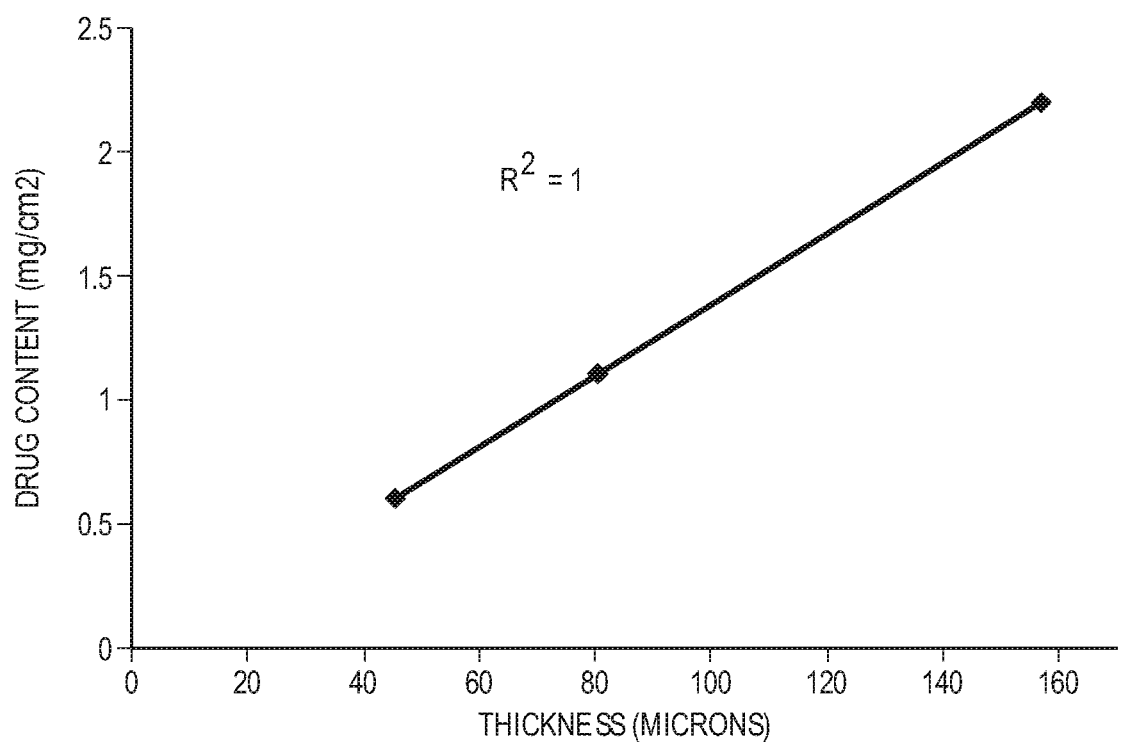
FIG. 20 displays the relation between film thickness and drug content for films formed using convective drying and high viscosity film-precursors.

In FIG. 20, the drug content as a function of film thickness is depicted, showing excellent linear fit, showing that the GF content is linearly proportional to film thickness, therefore, specific dosage may be delivered based on film thickness due to the excellent dispersion of drug nanoparticles that is achieved using the proposed formulation and methodology.

This also shows that the suspensions were well mixed and due to their sufficiently high viscosity, resulted in not only low percent variation in thickness, but also even lower API content uniformity RSD values.

TABLE 11

Content uniformity of films produced using convective drying and high viscosity film-precursors:

| Casting thickness (μm) | Dry film thickness (μm) | RSD % | GF (mg/cm$^2$) | RSD % |
| --- | --- | --- | --- | --- |
| 400 | 45.3 ± 3.1 | 6.8% | 0.67 ± 0.03 | 3.8% |
| 600 | 80.5 ± 2.2 | 2.8% | 1.03 ± 0.03 | 2.7% |
| 1000 | 158.1 ± 8.0 | 5.1% | 2.40 ± 0.12 | 5.0% |

Example 7: Preparation of Sub-100 nm Griseofulvin Drug Particles Using Wet Stirred Media Milling Aqueous suspensions containing as received griseofulvin (EP/BP grade, $d_{10}$=5.0 μm, $d_{50}$=21.85 μm and $d_{90}$=57.77 μm, Letco Medical Decatur, Ala., USA), hydroxypropyl methyl cellulose (HPMC-E3, Dow Chemicals, Midland, Mich., USA) and sodium dodecyl sulfate (SDS, Sigma Aldrich, Bellefonte, Pa., USA) were shear mixed at 300 RPM using a low shear laboratory stirrer (Fisher Scientific, Pittsburgh, Pa., USA) for about 45 minutes.

The final suspension had about 10% (w/v) griseofulvin, 2.5% (w/v) HPMC, and 0.2% (w/v) SDS in water. De-ionized water was used in all the experiments described here. Milling experiments were carried out in a Microcer model, wet stirred media mill (Netzsch Fine Particle size Technology, LLC (Exton, Pa., USA). The milling chamber had a volume of 80 ml, lined with zirconium oxide. Wear resistant yttrium-stabilized zirconia (Saint Gobain ZirPro (Zirmil Y, Mountainside, N.J., USA) with a nominal size of 100 μm was used as milling media. 195.75 gm milling media was loaded in the mill, and the tip speed of the mill was varied from 11.72 to 14.66 m/s (rotating shaft diameter: 7 cm). A stainless screen (Netzsch, Exton, Pa., USA) having opening pore size of 50 μm was used to restrict the flow of milling media out of the chamber.

Milled griseofulvin suspension was collected in the holding tank (500 mL), and a paddle mixer connected to the holding tank was operated at 800 RPM to ensure the suspension homogeneity. Recirculation of the suspension between holding tank and the milling chamber was achieved with use of peristaltic pump, and a flow rate of 126 ml/min was maintained. A chiller (Advantage Engineering, M1-.25A-11HFX, Greenwood, Ind., USA) was used to dissipate the heat generated during milling, such that the temperature of circulating suspension was maintained below 34° C.

Milled griseofulvin suspension at several milling times (4, 8, 16, 32, 64, 120, 180, 240, 300 and 360 min) were collected from the outlet of the milling chamber, and the particle size was measured using laser diffraction (LD) via Coulter LS13320 (Beckman Coulter, Miami, Fla., USA) using the Mie theory, and dynamic light scattering (DLS, Delsa Nano C Particle analyzer, Beckman coulter, Brea, Calif.). The term "median size" here refers to the 50% vol. passing size of the cumulative volume distribution in LD and cumulant or z-average mean size in DLS. The griseofulvin particle size above 160 nm was measured in LD and the sizes below were measured using DLS. The SEM images were taken using scanning electron microscope LEO 1530 SUMP (Carl Zeiss Inc., Peabody, Mass., USA). The particle size of un-milled drug suspension (in the presence of stabilizers), was also measured and referred as the $0^{th}$ minute particle size.

Figure 21:
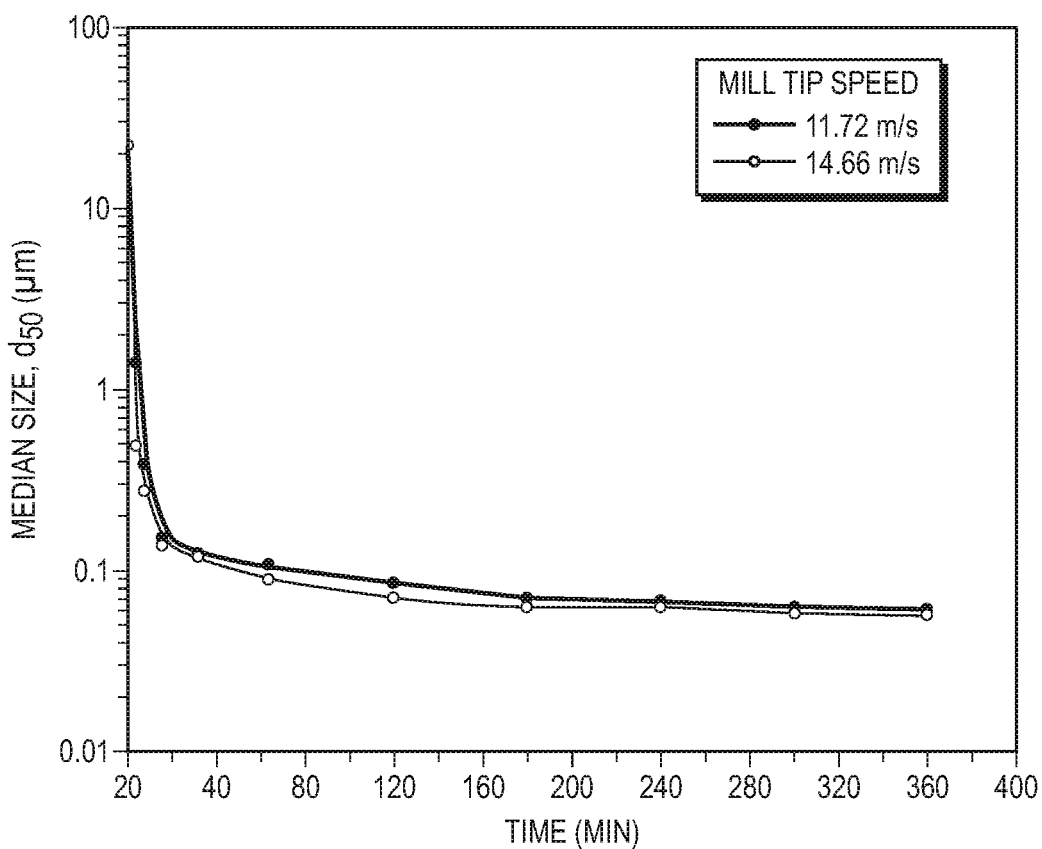
FIG. 21 shows the evolution of the median size of griseofulvin particles milled with 100 micron Yttrium stabilized zirconia milling media at two different mill tip speeds in wet stirred media milling.
Figure 22:
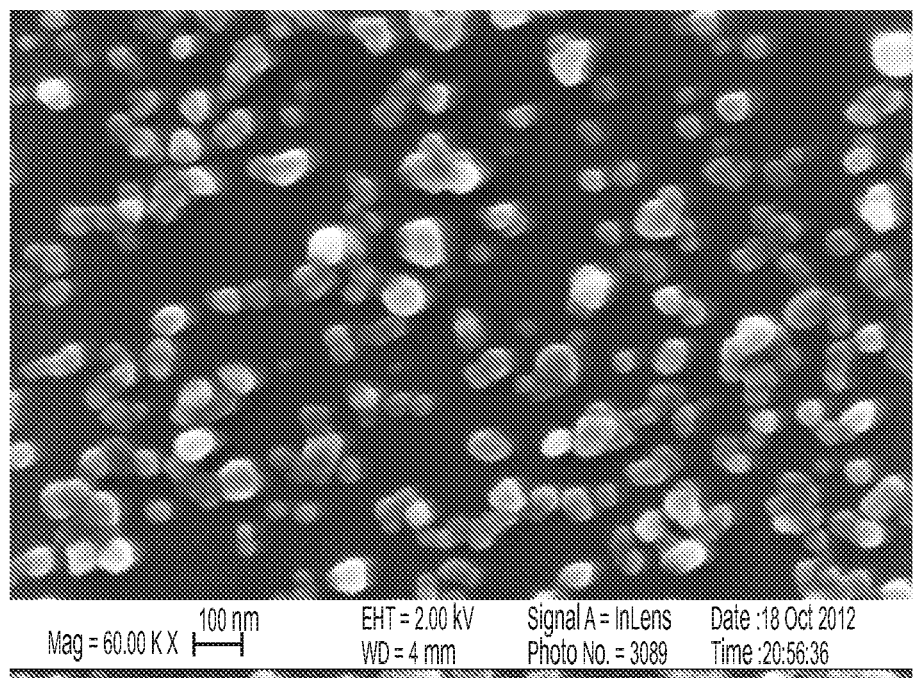
FIG. 22 shows a SEM micrograph of sub-100 nm griseofulvin particles produced via wet stirred media milling.

FIG. 21 shows the evolution of median ($d_{50}$) particle size of griseofulvin milled at two different mill tip speed with the use of 100 micron milling media. FIG. 22 shows the SEM image of 360th minute milled griseofulvin particles, and the particles were found to be spherical having average particle size of about 61 nm. Table 12 shows the particle size data taken at different time points of milling. The final particle size achieved at 360 min of milling at a tip speed of 11.72 m/s and 14.66 m/s were 60 nm and 56 nm, respectively. In both cases of milling, the particle size was less than 100 nm, which was mainly due to the use of smaller size milling media causing high fluctuating frequency and high frequency of bead compression events during milling. In the case of higher tip speed, the frequency of both events was higher and led to further reduction in particle size. Thus, the feasibility of preparing griseofulvin nanoparticles (less than 100 nm) was shown. These nano-particles in suspension form are used for making ultra-fast dissolving stripfilms as illustrated in next example.

TABLE 12

Median ($d_{50}$) particle size data of griseofulvin taken at different time points of wet stirred media milling, at two different mill tip speed:

| Time (min) | Tip Speed: 11.72 m/s $d_{50}$ (microns) | Tip Speed: 14.66 m/s $d_{50}$ (microns) |
|---|---|---|
| 0 | 21.845 | 21.845 |
| 4 | 1.378 | 0.479 |
| 8 | 0.378 | 0.267 |
| 16 | 0.149 | 0.134 |
| 32 | 0.122 | 0.112 |
| 64 | 0.106 | 0.087 |
| 120 | 0.084 | 0.069 |
| 180 | 0.069 | 0.061 |
| 240 | 0.067 | 0.064 |
| 300 | 0.062 | 0.059 |
| 360 | 0.060 | 0.056 |

Example 8: Preparation of Ultra-Fast Dissolution Thin Strip Films Containing Sub-100 nm Griseofulvin Particles In this example, sub-100 nm griseofulvin nano-particles of Example 7 were used. The time stable drug nano-suspension was used to make quick dissolving thin strip-films. The film forming precursor solution was prepared by adding 18.75 gm of hydroxypropyl methyl cellulose (HPMC-E15, Dow Chemicals, Midland, Mich., USA) and 6.3 gm (5.06 ml, density: 1.25 gm/ml) of glycerin in 100 ml of water, stirred at 240 RPM using low shear laboratory stirrer (Fisher Scientific, Pittsburgh, Pa., USA) at 80° C. for about 30 minutes.

The mixture was then allowed to cool to room temperature, followed by addition of 24 gm of milled griseofulvin suspension [8.8% griseofulvin, 2.2% HPMC-E3, 0.17% SDS, 88.73% water—all with respect to (w/w)] and stirred again for 3 h at 240 RPM. Homogenous polymer solution containing griseofulvin nanoparticles was caste in a continuous dryer (Lab-Cast Model TC-71LC Tape Caster, HED International, NJ) having both conductive and convective mode of drying. Silicone coated Mylar material was used as a substrate, rolled at a speed of 50 mm/min.

The drying temperature was kept constant at 60° C. Casting thickness was adjusted to 200 micron thickness using a Doctor blade film applicator. The film was dried for about 30 min, and the dried film thickness was measured to be about 16 micrometer. The disintegration time of dried films was noted by placing a ⅝ inch diameter film in 10 ml of water. The time taken by the film to disintegrate completely was about 10 seconds.

Figure 23:
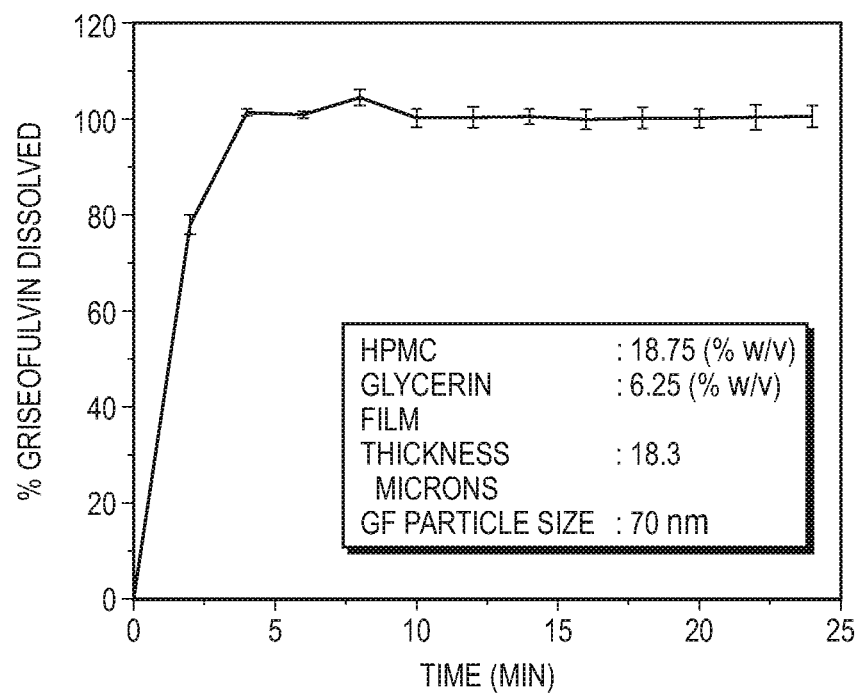
FIG. 23 shows dissolution profiles of about 70 nm griseofulvin nanoparticles loaded in about 18 micron thin film demonstrating ultra-fast drug release.

FIG. 23 shows the percent griseofulvin dissolved with respect to time in 0.025 M SDS solution. The dissolution experiments were carried out in flow through cell dissolution apparatus (USP IV, Sotax, Switzerland) in a manner similar to Example 4. As seen, griseofulvin was completely (about 100%) dissolved within five minutes in the SDS medium which is attributed to very thin HPMC film (about 18 micron) and the use of very small size griseofulvin nanoparticles (70 nm). This ultra-fast dissolution demonstrates another novel advantage of this disclosure.

Example 9: Comparison of Impeller and RAM Mixing for HPMC Films with the Addition of Antifoaming Agents Fenofibrate (FNB, Jai Radhe Sales, Ahmedabad, India) was milled and coated with pharmaceutical grade amorphous hydrophilic silica (Silica, M5P, Cabot Corporation, MA) in a Fluid Energy Mill (FEM, qualification model, Sturtevant Inc., Hanover, Mass.) for 100% surface coverage as described previously. The as-received FNB had a particle size of d50=10 microns, whereas after milling, the particle size was reduced to d50=2 microns. Dry surface coated FNB powder, 2.5 grams, was then mixed thoroughly with 0.3 grams of sodium dodecyl sulfate (SDS, Sigma Aldrich, Bellefonte, Pa., USA), and added to 50 grams of aqueous Hydroxypropyl methyl cellulose (HPMC-E15LV, Dow Chemicals, Midland, Mich., USA) solution and glycerin. The final weight percent of individual components were 8% HPMC, 5.2% glycerin, 24% of silica coated FNB and 0.6% SDS.

Two different mixing methods, as well as the addition of an antifoaming agent, were studied during this process. The first method involved the use of a standard impeller (VWR VOS 16 Overhead Stirrer, VWR catalog number 33998-454, VWR International) based mixing at 125 rpms for 3 hours. The other method involved putting the sample into a jar and then mixing it in a commercial resonant acoustic mixer (LabRam, Resodyn, Mont., USA), which is a high intensity vibratory mixer, at an intensity set at 80% for 2.3 minutes. Impeller mixing is a well-used method for mixing film precursors for creating polymer strip-films, although it takes nearly 3 hours longer than RAM mixing. One negative aspect of using a high-intensity vibratory mixing system is excessive foam generation, although it can be somewhat reduced through vacuum operation under vacuum.

In each method, anti-foaming agent was added to the suspension before mixing, in the amounts 0.1, 0.5 and 1.0% by weight relative to the polymer suspension to avoid foam formation during mixing. Three different antifoaming agents (Dow Corning: Q7-2587—30% Simethicone emulsion USP; 7-9245—30% Simethicone emulsion USP, and Medical Antifoam C) were initially studied for RAM mixing. After proper mixing and approximately 8-12 hours of settling time to ensure there were no air bubbles, the suspension was cast with a Doctor Blade set at an initial wet film thickness of 1000 microns, followed by drying.

The API loading of these dry films were made at 24% by weight by altering the initial amount of dry powder added to the polymer suspension. First, the effectiveness of the different types of antifoaming agents was evaluated. This was done by measuring the height of the polymer suspension (without API) in the jar, both before and after mixing. The difference in height is the amount of foam that is caused due to the high intensity mixing. It was found that a concentration of 0.1% wt of defoamer is too low to make a difference in foaming, but as concentration increases, the foam height decreases. Overall, the best defoamer was found to be Q7 at a concentration of 1.0% wt; although the films employed in dissolution testing used 0.5% of Q7.

The impact of intensity of mixing on the dissolution rate in 5.4 mg/mL aqueous SDS was examined. The dissolution experiments were performed by cutting out a ⅜ inch diameter sample of film and placing it into a flow-though cell dissolution apparatus (USP IV, Sotax, Switzerland) while 118 mL (5.4 mg/mL) aqueous SDS passed through cells (internal diameter of 22.6 mm) at a rate of 16 mL per minute. The amount of API dissolved from the film was measured over time until 100% of drug was released.

Figure 24:
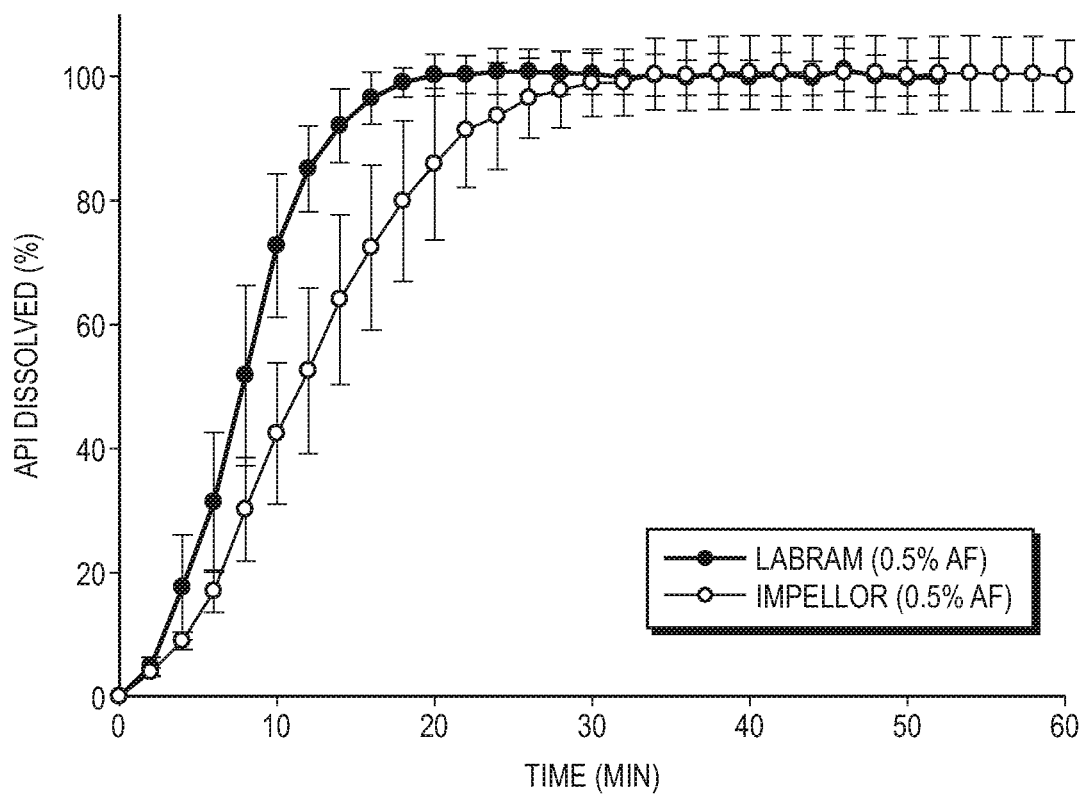
FIG. 24 shows dissolution profiles of silica-coated FNB microparticles that are mixed with 0.5% anti-foaming agent Q7 in the labRAM versus the impeller.

FIG. 24 shows that the dissolution rates are comparable for both methods of mixing, however, the sample that was mixed in the RAM dissolves faster than the impeller mixed sample. This shows that better mixing may be produced in RAM or any equivalent vibratory mixer and will lead to better performing films.

ing uniform films across multiple drugs. FIGS. 25A-D show the dissolution profiles of drug release from films with and without surfactant. The dissolution curves with and without surfactant were found to be statistically similar for all four drug formulations suggesting that the dissolution of drug from the film was controlled by the erosion of the polymer matrix and that surfactant in the film formulation had little impact on the dissolution profile.

TABLE 13

Suspension formulations for inclusion into HPMC films:

| Formulation | API | wt % API | wt % HPMC | wt % SDS |
|---|---|---|---|---|
| F1 | FNB | 8.4 | 2.5 | 0.0 |
| F2 | FNB | 8.4 | 2.5 | 0.5 |
| I1 | IBU | 8.4 | 2.5 | 0.0 |
| I2 | IBU | 8.4 | 2.5 | 0.5 |
| N1 | NPX | 8.4 | 2.5 | 0.0 |
| N2 | NPX | 8.4 | 2.5 | 0.5 |
| A1 | AZD | 8.4 | 2.5 | 0.0 |
| A2 | AZD | 8.4 | 2.5 | 0.5 |

TABLE 14

Content uniformity of drug nanoparticle-laden films with and without surfactant:

| Formulation | F1 | F2 | I1 | I2 | N1 | N2 | A1 | A2 |
|---|---|---|---|---|---|---|---|---|
| Thickness (µm) | 92.8 | 102.0 | 93.7 | 97.1 | 101.5 | 108.3 | 98.8 | 92.6 |
| RSD % | 2.4% | 1.4% | 5.2% | 1.9% | 5.4% | 0.8% | 2.1% | 1.4% |
| Drug mass per unit area (mg/cm$^2$) | 1.71 | 2.08 | 1.88 | 2.11 | 1.53 | 1.84 | 1.97 | 2.00 |
| RSD % | 2.8% | 4.2% | 5.1% | 3.7% | 5.0% | 3.1% | 3.1% | 2.7% |
| wt % drug | 14.9 | 17.0 | 16.0 | 18.2 | 12.7 | 14.2 | 16.6 | 17.7 |
| RSD % | 2.0% | 2.6% | 2.1% | 1.3% | 1.6% | 1.6% | 2.2% | 0.7% |

Example 10: Influence of High-Shear Mixing on Dispersion of Nano-Particles and Film Precursor Stabilization: Preparation of Surfactant-Free HPMC Strip Films Containing Poorly Water Soluble Drugs In this example, it is shown that uniform polymer strip films can be prepared for a variety of poorly water soluble drugs and that fast dissolution from the strip films is achievable even when surfactant is absent from the formulation. Consequently, the feasibility of forming homogeneous fast dissolving films from surfactant-free nano-suspensions of several drugs is demonstrated. Nano-suspensions were prepared via a WSMM method containing fenofibrate (FNB), ibuprofen (IBU), naproxen (NPX), and azodicarbonamide (AZD) as model BCS Class II drugs, as described by the formulations in Table 13.

An aqueous polymer solution containing 17% (w/w) HPMC and 5% (w/w) glycerin were used in this study. The dissolution behavior of the strip-films containing drug nanoparticles was examined following the protocol described in Example 4. Table 14 shows content uniformity results for strip films loaded with drug nanoparticles (with and without surfactant).

All formulations exhibited good content uniformity (less than 6% RSD), demonstrating the capability of manufactur- Example 11: High Resolution Drug Distribution Imaging Using Raman Chemical Mapping of Films Produced with and without Using Convective Drying This example demonstrates the use of Raman image analysis for analyzing the distribution of griseofulvin (GF) nanoparticles in HPMC based polymer films. The impact of composition (viscosity) and drying method on content uniformity were analyzed. Table 15 provides the wet film formulations of the two samples analyzed.

RF1 contains lower concentration of HPMC (E15LV) and higher concentration of API, and the resulting suspensions have a low viscosity of about 1000 cP. Formulation RF2 has a polymer blend of HPMC (E15LV) and PVP (K-90) mixed with GF nano-suspensions at a lower concentration about 3 wt %. This blend has a viscosity of about 8000 cP.

The precursor solution preparation, mixing and casting methods were in accordance with the previously described protocols. The drying method employed in both cases however was different. Composition RF1 was cast on a steel plate using a casting knife and dried in a conventional oven at 40° C. overnight, whereas composition RF2 was cast onto a Mylar substrate of a continuous drier (lab coater, model number TC-71LC, HED international, USA) using a doctor blade.

The drying temperature and air flow in the continuous drying line was 60° C. and 0.5 mps, respectively. The final thickness of films was measured using a digital micrometer (Mitutoyo, Japan) to be 80±5 µm respectively. The drug content in the films was measured as an average of ten samples (having an area of 0.712 cm$^2$) from each of the film and dissolving them in 250 ml SDS (5.4 mg/ml) solution. The drug content is measured using a UV-Vis spectrophotometer (Sotax, USA). The final drug (GF) loading in films made from formulation RF1 was found to be about 25 wt % and RF2 about 11 wt %.

Figure 26A:
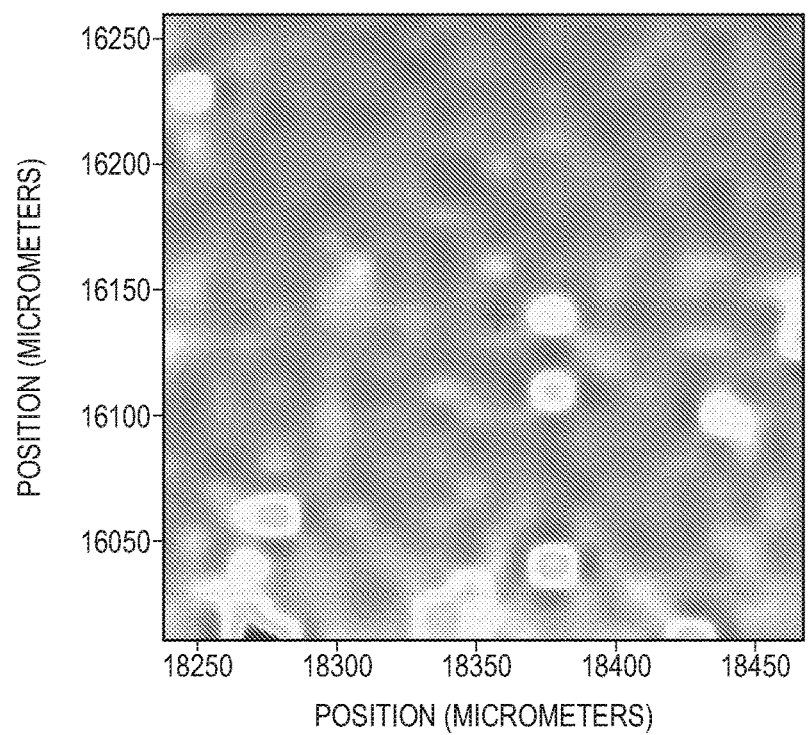
FIGS. 26A-B show Raman chemical imaging applied to griseofulvin films. Each image is of 250×250 micron area.
Figure 26B:
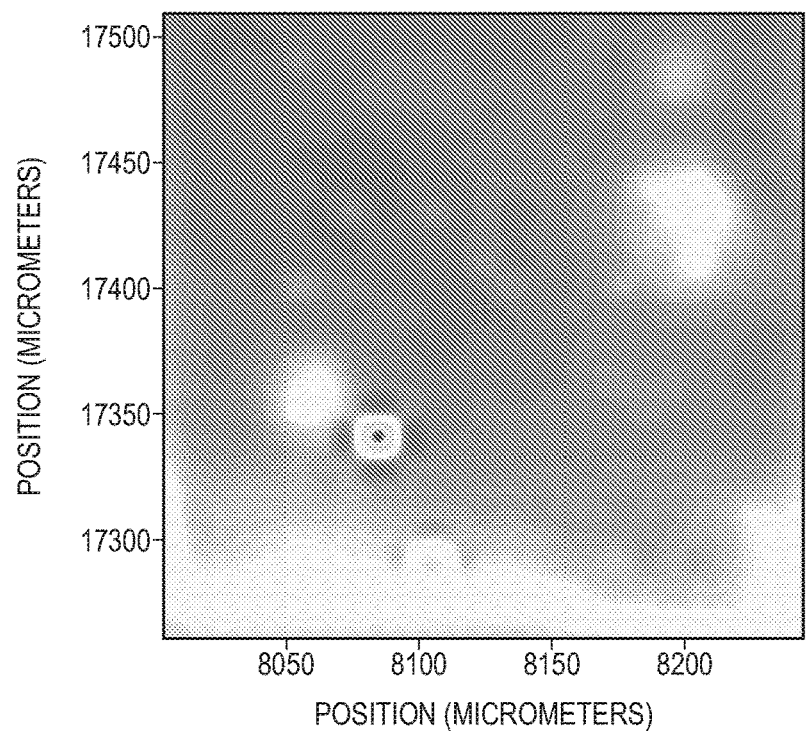

Raman image analysis was performed using ThermoScientific DXR Raman microscope (ThermoScientific, USA). Both images were taken in 10×10 micron steps with a 10× microscope objective and 10 micron spatial resolution. As can be seen from FIGS. 26A-B, films made from formulation RF2 have uniformly distributed API at the 10 micron spatial resolution level. On the other hand, films made from formulation RF1, appear to have agglomerated API at the 10 micron level. In both the cases however, there was no indication of formation of an amorphous phase.

Raman spectra for pure GF powder and GF nanoparticles in films were analyzed to get an estimate of the drug content in these films. The predicted and actual values are shown in Table 16. The predicted values from Raman analysis and actual values from assay analysis are in good agreement for films made from formulation RF2, whereas the predicted and actual values differ significantly for films made from formulations RF1. These results further prove that the starting precursor viscosity and drying method have a significant impact on the final content uniformity of the films.

TABLE 15

Composition of wet film (wt %) used in this study:

| Formulation | HPMC (E15LV) | PVP (K90) | Glycerin | GF | SDS |
|---|---|---|---|---|---|
| RF1 | 6.10 | none | 5.00 | 4.40 | 0.22 |
| RF2 | 7.40 | 6.67 | 3.33 | 2.94 | 0.15 |

TABLE 16

Actual and predicted wt % values for films:

| Formulation | Actual (wt %) | Predicted (wt %) |
|---|---|---|
| RF1 | 25 | 6 |
| RF2 | 11 | 12 |

Example 12: Effect of Swelling Properties of Superdisintegrants on Polymer Based Film Formulations Containing Griseofulvin Nanoparticles The swelling characteristics of superdisintegrants (SDIs) have been exploited for various applications in tablet formulations; however, their role as additives in fast dissolving oral strip-film formulations for film precursor viscosity enhancements has not been investigated. One goal of the current disclosure is to explore the impact of SDIs, namely sodium starch glycolate (SSG), crosscarmellose sodium (CCS) and crosspovidone (CP) on hydroxypropyl methylcellulose (HPMC (E15LV grade))-based film formulations containing poorly water soluble drug nanoparticles. The performance of SDIs was also compared against traditionally used viscosity enhancing agents or swelling agents, such as natural gums and high-molecular-weight cellulose polymers. Strip-films were formed by casting and drying HPMC solutions mixed with additives (SDIs or VEAs) and wet stirred media milled griseofulvin nanoparticle suspensions. Rheometry, particle sizing, scanning electron microscopy, thermogravimetric analysis, and Raman spectroscopy were used to determine the rheological behavior, particle size distributions of GF and the SDIs, GF crystallinity and final moisture content in films. It was observed that the swelling properties of SDIs resulted in enhancing the viscosity of HPMC-GF suspensions, thus aiding in maintaining uniform distribution of GF across the films and also resulting in fast re-dispersion and release of GF. Incorporation of SDIs had no negative impact on GF crystallinity and resulted in minimal water content in films, which could also aid in long shelf life of dosage form. Overall SDIs performed better than VEAs resulting in uniform films.

Superdisintegrants (SDIs) are water insoluble, crosslinked polymers which swell upon contact with dissolution media. Due to their swelling capacity, SDIs are commonly used in tablet formulations for quick disintegration and release of drugs. SDIs have also been utilized for various applications in dry powder formulations. More recently, their application as stabilizers for nano-milling of poorly water soluble drug compounds has also been explored. Researchers have demonstrated the use of crosscarmellose sodium (CCS) as a dispersant for promoting fast dissolution of drug particles from nano-composite systems. Due to its high swelling capacity and ionic charge associated with CCS, co-milling of CCS with poorly water soluble drug compounds in the presence of a soluble adsorbing polymer like HPC and HPMC imparted enhanced physical stability to the drug particles and resulted in faster recovery of drug particles upon re-dispersion. Others demonstrated the use of sodium starch glycolate (SSG), an anionic superdisintegrant, for formation of stable aqueous based colloidal suspension via wet stirred media milling in absence of stabilizers (such as surfactants or polymers). Despite interest and multiple applications of SDIs in variety of dry dosage forms, there have been very few studies which investigated the impact of SDIs on strip-films for oral delivery of drugs.

Oral strip-film technology has emerged as a promising platform for drug delivery due to its patient compliance, potential for continuous processing and cost-effective manufacturing. Strip-films can be used for delivery of drug via multiple routes, thus in some cases aiding bioavailability enhancement of drugs. Unlike tablet formulations which have minimal solvent, film formulations are typically solvent based suspensions or solutions containing multiple components. The present disclosure has demonstrated the use of strip-film technology for the delivery of poorly water soluble drug nano or micro particles (produced via bottom up or top down approaches). In such cases, the formulations contain viscous polymer solutions mixed with drug solutions or drug nano or micro suspensions (along with additives such as surfactants, plasticizers, etc.). One parameter for formation of uniform strip-films is the starting precursor solution viscosity. The viscosity of these precursor solutions can vary between 5,000 cP and 60,000 cP. The present disclosure demonstrates the importance of starting suspension viscosity for developing uniform polymer films containing griseofulvin (GF) nanoparticles.

Few articles discuss the impact of SDIs on film disintegration and dissolution behavior. However, none of these articles discuss the interaction between SDIs and the film forming components. The effect of SDI swelling behavior on stability of film precursor suspensions and resulting drug distribution (within the dry film matrix) has not been thoroughly investigated. Incorporation of SDIs (like SSG and CCS) can also impart electrostatic stabilization to the drug particles in film precursor solutions (depending on the SDI concentration), in addition to aiding in fast disintegration and dissolution of films. Therefore, it is of interest to explore the interactions between SDI particles with viscous polymeric colloidal film precursor suspensions consisting of drug nanoparticles. The effect of swelling capacities of ionic and non ionic SDIs on film formulations containing poorly water soluble drug nanoparticles has not been documented before.

One goal of the present disclosure is to investigate the effect of swelling characteristics of three SDIs: croscarmellose sodium (CCS), sodium starch glycolate (SSG) and crosspovidone (CP) on hydroxypropyl methylcellulose (HPMC) films containing GF nanoparticles. Low molecular weight HPMC (E15LV) solutions were prepared in combination with glycerin and SDIs (1 wt %). These solutions were then mixed with GF nano-suspensions produced via wet stirred media milling (WSMM). To assess the impact of SDI swelling capacity on film properties, their performance was compared against traditionally used viscosity enhancing agents (or swelling agents) in film formulation such as pectin, guar gum (GG) and xanthan gum (XG). HPMC solutions were also prepared by adding 1 wt % of pectin, GG and XG, followed by mixing with GF nano-suspensions. Viscosity and shear thinning behavior of these suspensions were studied using a Brookfield rheometer and empirical equations were used to describe the non-Newtonian behavior of suspensions. Strip-films were fabricated by casting the suspensions and drying via a convective heating mechanism. The particle size distribution of SDIs before and after incorporation into films were analyzed using laser diffraction techniques. The same technique was also used to analyze the particle size of GF after film re-dispersion. Raman spectroscopy was used to study the crystallinity of GF while Fourier transform infrared spectroscopic techniques was used to study the interactions between various additives, GF nanoparticles and HPMC matrix. The dry films were also investigated for content uniformity and dissolution behavior. Scanning electron microscopy (SEM) was applied to study the structure of HPMC films and to visualize the GF distribution within the HPMC matrix. Thermogravimetric analysis (TGA) was performed to record the final moisture content in films, which is an important parameter for long term stability of films. It was observed that the addition of SDIs significantly enhanced the viscosity of HPMC-GF suspensions. The addition of SSG had maximum impact on viscosity due to its high swelling capability; and the viscosity enhancement was comparable with that of XG. Films made from suspensions containing SSG demonstrated excellent content uniformity (with RSD values less than 3%) and fast dissolution behavior. Overall the addition of SDIs resulted in fast re-dispersion and dissolution of GF particles, when compared with films containing GG, XG or pectin.

Materials:

Griseofulvin (GF; Sigma-Aldrich, Saint Louis, Mo.) was utilized as a model drug. Sodium dodecyl sulfate (SDS) (Sigma-Aldrich, Saint Louis, Mo.) and low molecular weight hydroxypropyl methylcellulose (HPMC; Methocel E15LV) (Dow Chemicals,) were used as stabilizers for GF nanosuspensions; the latter was also used as a film former. Glycerin (Sigma-Aldrich, Saint Louis, Mo.) was used as a plasticizer. CCS, CP (kollidon CL) and SSG were purchased from FMC Biopolymer (Philadelphia, Pa.), BASF Chemical Co. (Florham Park, N.J.) and ISP (Wayne, N.J.) respectively. Pectin, guar and xanthan gums were purchased from Sigma-Aldrich (Saint Louis, Mo.).

Preparation of GF Nanosuspensions:

GF nanosuspensions were produced via WSMM utilizing a Microcermill (NETZSCH, Fine particle technology LLC, Exton, Pa.) as per previously described methods and processing conditions. HPMC and SDS were chosen as stabilizers. The end point of milling was determined as the point where the particle size did not change further (d50 was about 160 nm). At the end of milling, a sample was taken from the holding tank of the mill and dispersed into 15 mL HPMC-SDS stabilizers solution (using a pipette) and the particle size distribution of GF in the sample was then measured using laser diffraction in Coulter LS13320 (Beckman Coulter, Miami, Fla.).

Preparation of Film Precursor Suspensions:

HPMC polymer solutions were prepared following DOW protocol. Briefly stated, a weighed amount of HPMC, and glycerin were added to water (on w/w basis) at 90° C. The solutions were allowed to cool down to room temperature while being stirred continuously. SDIs (SSG, CCS and CP) were added to the solution as the solution cooled down, with continued stirring. These HPMC solutions containing SDIs were then mixed with GF nano-suspensions in a 2:1 ratio for a period of 6 h using a motor driven dual-propeller mixer (McMaster, USA). Based on preliminary studies, the polymer concentration was fixed at 12 wt %, glycerin at 5 wt % and SDI at 1 wt %. It was observed that a minimum viscosity of 5000 cP was required for formation of a stable film matrix. The viscosity of 12 wt % HPMC is about 5000 cP. However, this viscosity value reduces after the addition of nano-suspensions (2500 cP). Since these viscosities are still low for film formation, they may be utilized for better assessment of the impact of SDI swelling capacity. The impacts of SDI swelling characteristics on aqueous precursor suspension and dry film properties were also compared against other viscosity enhancing polymers such as guar gum, xanthan gum and pectin. HPMC solutions containing gums, pectin and glycerin were prepared following DOW protocol. These solutions were then mixed with GF nano-suspensions. Two additional formulations were also considered where viscosity enhancement was achieved either by increased amount of polymer (S7), or by adding higher molecular weight grade of HPMC (S8). Table 17 gives the composition of all the formulations used in this study. Formulation S, which does not contain any additive, is used as a standard and samples S1-S3 are compared against S and S4-S8.

TABLE 17

Wet suspension composition for different formulations used in this study (after addition of GF nanosuspensions):

| Formulation | Additive type | HPMC % (w/w) | Glycerin % (w/w) | Disintegrant % (w/w) | GF % (w/w) | SDS % (w/w) |
|---|---|---|---|---|---|---|
| S | No additive | 8.50 | 3.33 | 1.10 | 2.94 | 0.15 |
| S1 | SSG | 8.50 | 3.33 | 1.10 | 2.94 | 0.15 |
| S2 | CCS | 8.50 | 3.33 | 1.10 | 2.94 | 0.15 |
| S3 | CP | 8.50 | 3.33 | 1.10 | 2.94 | 0.15 |
| S4 | Pectin | 8.50 | 3.33 | 1.10 | 2.94 | 0.15 |

TABLE 17-continued

Wet suspension composition for different formulations used in this study (after addition of GF nanosuspensions):

| Formulation | Additive type | HPMC % (w/w) | Glycerin % (w/w) | Disintegrant % (w/w) | GF % (w/w) | SDS % (w/w) |
|---|---|---|---|---|---|---|
| S5 | Guar gum | 8.50 | 3.33 | 1.10 | 2.94 | 0.15 |
| S6 | Xanthan gum | 8.50 | 3.33 | 1.10 | 2.94 | 0.15 |

Characterization of Suspensions: Rheology of Suspensions:

The apparent viscosity of suspensions was measured using an R/S plus rheometer (Brookfield Engineering, Middleboro, Mass.). The rheometer was equipped with a shear rate controlled coaxial cylinder (CC40) and a water jacket assembly Lauda Eco (Lauda-Brinkmann LP, Delran, N.J.). The temperature of the jacket was kept constant at 25±0.5° C. The suspensions were subjected to a low shear rate program to measure the viscosity at low shear value (0-20 s-1) and a high shear rate program (0-1000 s-1) to study the impact of shear rate on viscosity. The low shear program was run at 25° C. However, for the high shear program, the suspensions were heated up to 45° C. to reduce their viscosity, which was required due to the viscosity range limitations of the instrument used. To ensure that the temperature did not have drastic effect on the viscosity-shear rate behavior, the program was also repeated at 55° C. and 60° C. The raw data was analyzed using the Rheo 3000 software (Brook-field Engineering, Middleboro, Mass., USA) of the R/S plus rheometer. Each experiment was performed in triplicate and the average and standard deviation values were recorded. Established empirical correlations were applied to characterize the non-Newtonian behavior of the suspensions.

Particle Size Distribution:

The particle size distribution of GF was measured in suspensions after milling, after mixing with polymer solutions (S-S8) and from re-dispersed films using a laser diffraction technique. The effective use of laser diffraction technique for measurement of swollen SDI particle size was done as has been previously demonstrated. The size of SDIs (SSG, CCS and CP) was recorded for three cases: after incorporation into HPMC solution, before and after addition of GF nano-suspension and after film re-dispersion. Film re-dispersion was performed by dissolving a small piece of film (about 0.712 cm$^2$ in area) into 10 mL DI water followed by vortex mixing for 1 min. The same procedure was also followed for formulations S4-S8. Each experiment was performed in triplicate.

Preparation and Characterization of Polymer Films Containing GF Nanoparticles: Preparation of Polymer Films:

Approximately 8 g of the final viscous suspensions were manually cast onto a stainless steel substrate (at 25° C.) using a casting knife (Elcometer, MI). The casting thickness was set at 1000 μm and the final dimensions of the film were measured to be about 8 cm×9 cm. The cast film along with the substrate was then placed into zone three of a Lab-Cast Model TC-71LC Tape Caster, HED International, and dried at 60° C. for a period of 30 min. The continuous film casting line has three zones of heating. Zone one and two apply conductive heating mechanism, while zone three applies both conduction and convective heating mechanism. For the current study the films were manufactured in batch mode by placing the film in zone 3 of the unit and drying the cast film. The drying conditions in zone 3 were maintained based on previous optimization studies. The dried film was then peeled off the substrate and placed in a desiccator to avoid any further moisture absorption. The same procedure was followed for all the formulations (S-S6).

Scanning Electron Microscopy (SEM):

A field emission scanning electron microscope (FESEM) LEO1530VP GEMINI (Carl Zeiss, Inc., Peabody, Mass.) was used to examine the polymeric (network) structure and to observe the presence of any GF aggregates within the films. A small sample of the film was placed on carbon tape (the stub) followed by carbon coating using a sputter coater followed by imaging. The cross sectional images of all the seven films (S-S8) were recorded.

Raman and Fourier Transform Infrared Spectroscopy:

Raman studies were performed to observe the crystallinity of GF nanoparticles after incorporation into films. A EZRaman LE Raman Analyzer system from Enwave Optronics (Irvine, Calif.), with an HRP 8 high throughput fiber probe coupled to a MicroView adapter with a 10× objective 10 μm spot size was used for this purpose. A 250 mW 785 nm was used for measurements on pure GF powder and for film samples. Raman spectra were collected every 15 s with an average of 5 scans. FTIR studies were performed to investigate the interaction of HPMC or SDIs or pectin, GG and XG with GF nanoparticles.

Thermogravimetric Analysis (TGA):

Thermogravimetric analysis (TGA) of films with and without GF nanoparticles was performed with a TGA/DSC1/SF Stare system (Mettler Toledo, Inc., Columbus, Ohio). A small sample of a film (about 3.0 mg) was placed in a ceramic crucible, heated from 25° C. to 150° C. in a nitrogen atmosphere at a constant heating rate of 5° C./min, kept at 150° C. for 15 min and then heated up to 300° C. at a rate of 5° C./min. Finally, the sample was brought back to room temperature (25° C.) at a cooling rate of 10° C./min. Each measurement was duplicated for all the compositions (S-S8).

Determination of Drug Content in Films:

A Thermo Scientific Evolution 300 UV-Vis spectrophotometer (Thermo Fisher Scientific Inc., MA) was used to determine the drug content in films. Ten samples of about 0.712 cm$^2$ in area were punched out of each film (S-S8) and dissolved in 250 mL of 0.0187 M SDS solution for a period of 12 h. The concentration was calculated via UV absorbance at 291 nm using previously constructed calibration curves. The average GF weight and relative standard deviation over ten samples was calculated.

Mechanical Properties:

The mechanical properties of films were measured using a TA-XT Plus Texture Analyzer (Stable Microsystems, UK). Tensile and yield strength were computed from the stress versus strain data Six rectangular strips having dimensions of 50 mm×15 mm were cut from a single film and tested. The strip was held in place between the two grips and stretched at a test speed of 1 mm/s until the breaking point (e.g., tensile failure). The average and standard deviation were computed over six samples and tabulated.

Dissolution Testing and Drug Release Kinetics:

It has been demonstrated that the use of USP 4 flow-through cell dissolution apparatus is effective for discrimination of nanoparticle dissolution from films. Therefore, for the present disclosure, a flow-through cell dissolution apparatus (USP 4, Sotax, Switzerland) with cells of an internal diameter of 22.6 mm was employed. Circular film samples (having an area of 0.712 cm$^2$) were horizontally positioned in the cells with glass beads (1 mm in diameter) filling the top and bottom of each cell. Pall HT Tuffryn membrane disc filters (0.2 μm) were used (previous studies demonstrated that the use of 0.1 μm versus 0.2 μm filters did not have any significant impact on the release profiles of films containing nanoparticles of mean diameter 160±30 nm). The temperature was maintained at 37±0.5° C. and a flow rate of 16 mL/min was used. Dissolution experiments were carried out using two different media. In the first case, a 100 mL dissolution medium (USP recommended SDS solution (5.4 mg/mL) was circulated by pumping it through each cell. For the second case, deionized (DI) water was used as the media. Six samples were used from each film (S-S8) and the average drug release was plotted as a function of time. To better understand the effect of SDIs on rate of drug release from HPMC films, two new formulations were prepared (formulation S7 and S8). In the first case a high molecular weight HPMC (E4M, Dow chemicals) was used to prepare films loaded with GF nanoparticles. In the second a higher concentration of HPMC (E15LV) was used to prepare films containing GF nanoparticles (following the same procedure stated above). The percent drug loading and film thickness were kept same as formulations S-S8 and same dissolution testing protocols were followed. The release kinetics of GF from HPMC films was determined by finding the best fit for the release profiles. Zero-order release equation, first-order release equation, Higuchi equation and Korsmeyer-Peppas (KP) equation were used to analyze the release kinetics of GF. The linear portions of the release curves (corresponding to 60% of drug release based on drug assay analysis) were fitted using the models mentioned above. Similarity and difference factors were also computed between dissolution profiles of GF from films to determine the differences between various formulations (S-S6).

Results and Discussion:

Rheology of Suspensions:

Table 18 shows the apparent viscosity values for suspensions S-S8, before and after addition of GF nano-suspensions. Formulation S (which is a control) has the lowest value for viscosity, and it can be observed that addition of SDIs enhances the viscosity of HPMC solutions (S versus S1-S3). Addition of SSG resulted in significant increase in viscosity, followed by CCS and CP. SSG, due to its high swelling capacity, absorbed water from the HPMC solutions, thus resulting in an overall increase in polymer concentration which causes an increase in viscosity. CCS and CP also follow a similar mechanism; however, the swelling capacities of CCS and CP are lower than that of SSG. The addition of XG also resulted in a significant increase in suspension viscosity, followed by pectin and GG, all of these components also swell upon contact with water thus causing the increase in viscosity.

Figure 27A:
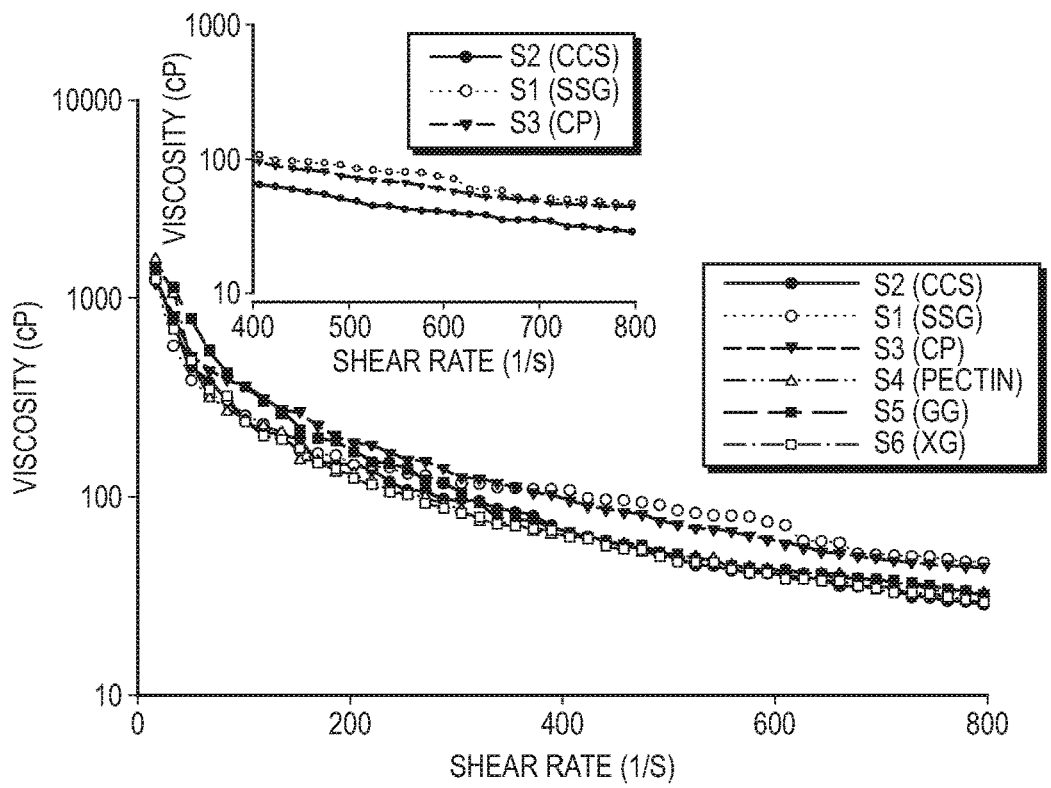
FIGS. 27A-B show viscosity versus shear rate plot for suspensions (FIG. 27A) in the presence of GF nanoparticles, and (FIG. 27B) in the absence of GF nanoparticles.
Figure 27B:
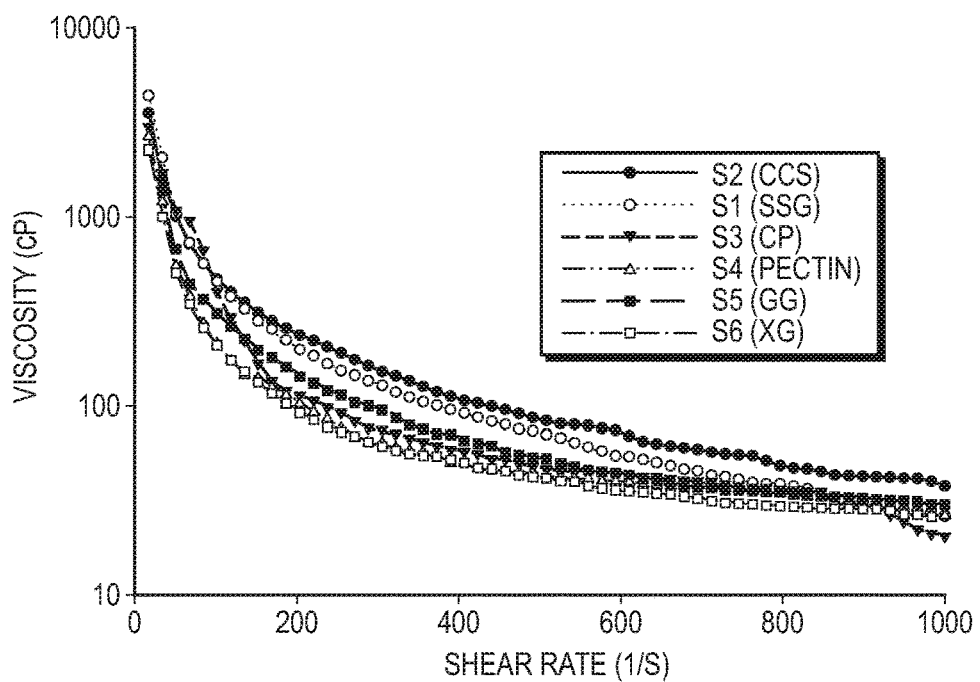

FIGS. 27A-B show the viscosity versus shear rate plots for formulations S1-S8 before and after addition of GF nano-suspensions. As a general trend, with an increase in shear rate, the viscosity of the suspensions decreased significantly. The presence or absence of GF particles did not have any significant impact on the shear thinning behavior of the suspensions. As the overall concentration of GF in the suspensions was low (about 3 wt %), and the particles are well covered in the polymer matrix, their impact on rheology is masked or negligible. Overall, the Ostwald de Waele power law model was found to be a good fit for the all the formulations ($R^2>0.98$, the fitting parameters are not shown for the sake of brevity). It is hypothesized that since HPMC is the predominant component in all of these suspensions, the shear thinning behavior of HPMC is most prevalent. Researchers have applied a simple calculation for characterizing the stability of suspensions containing drug nanoparticles, known as the shear viscosity ratio. They concluded that as the shear thinning behavior reduces, the suspensions become more Newtonian (thereby reducing the shear viscosity ratio) which implies the absence of any drug particle aggregates. For the present study, since the suspensions are very viscous and the overall concentration of GF was small, the suspensions did not reach a steady Newtonian plateau. However, a simple calculation of shear viscosity ratio ($\mu_{L0}/\mu_L$) for various formulations demonstrated that suspensions containing SSG had the smallest value, implying they were stable suspensions. The shear viscosity ratio values varied from 33 (for suspensions containing SSG) to 60 (for suspensions containing XG). The impact of SDS on rheology was also found to be negligible, since the amount of SDS present in the suspensions was well below the critical micellar concentration.

TABLE 18

Viscosity of HPMC solutions containing various additives, before and after addition of GF nanosuspensions (viscosity values were recorded at a low shear rate value of 2.2 s$^{-1}$, average and standard deviation over six runs is presented):

| Formulation | Additive | Viscosity of formulation (cP) before addition of GF nanosuspension | Viscosity of formulation (cP) after addition of GF nanosuspension |
|---|---|---|---|
| S | No additive | 5000 ± 300 | 2500 ± 200 |
| S1 | SSG | 20954 ± 847 | 11764 ± 300 |
| S2 | CCS | 15000 ± 400 | 5371 ± 250 |
| S3 | CP | 8112 ± 216 | 2357 ± 210 |
| S4 | Pectin | 14741 ± 561 | 4274 ± 333 |
| S5 | Guar gum | 9790 ± 589 | 3320 ± 273 |
| S6 | Xanthan gum | 23288 ± 499 | 12381 ± 392 |

Figure 28:
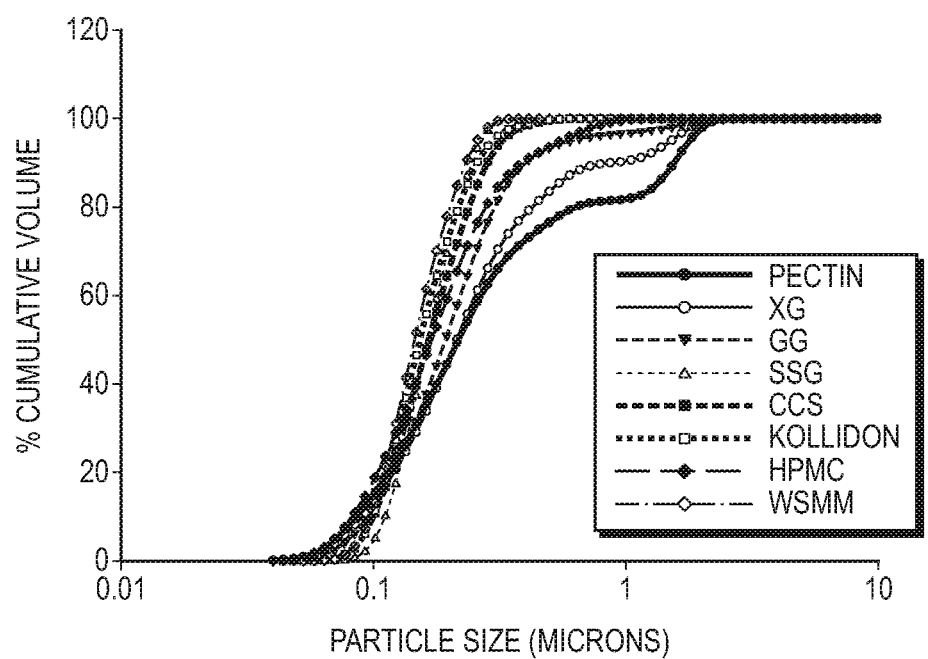
FIG. 28 shows a comparison of cumulative particle size distribution curves for GF nanoparticles re-dispersed from dried HPMC films (all seven formulations) and original GF nanosuspension produced via WSMM.

Particle Size Analysis:

The degree of SDI swelling was characterized via its particle size analysis. Table 19 shows the $d_{50}$ and $d_{90}$ values of SSG, CCS and CP in HPMC solutions (before and after addition of GF nanosuspensions) and from film re-dispersion. SSG shows maximum swelling followed by CCS and CP for all the three cases. One of the requirements for oral strip-films is preservation and recovery of nano GF particles upon re-dispersion, as poor drug nanoparticle recovery can lead to reduced bioavailability of drug. FIG. 28 compares the cumulative particle size distribution of GF in nanosuspensions against GF size distributions from film re-dispersion, from all the formulations. It was observed that the addition of SDIs did not lead to any particle aggregation, and the $d_{50}$ values for GF re-dispersed form formulations S1-S3 were comparable with GF from WSMM, e.g., wet stirred media milling, (Table 20). On the other hand, films containing XG, GG and pectin led to the formation of very strong film matrices, which made re-dispersion of GF particles very difficult. Therefore the particle size distributions (the $d_{90}$ values) for formulations S4-S6 were not reliable. SEM images also showed slight aggregation of particles in films containing pectin, GG and XG. Overall, films containing SSG gave the best size distribution (comparable to GF distribution from WSMM suspensions).

TABLE 19

Particle size distribution of SDIs (SSG, CCS and CP) dispersed in HPMC solutions before and after addition of GF nanosuspensions and from redispersed films (average and standard deviation over three samples is presented):

| SDI type | Size of SDI particles in HPMC solutions (before addition of GF nanosuspensions) | | Size of SDI particles in HPMC solutions (after addition of GF nanosuspensions) | | Size of SDI particles after film redispersion | |
|---|---|---|---|---|---|---|
| | d 50 | d 90 | d 50 | d 90 | d 50 | d 90 |
| SSG | 166.6 ± 4.0 | 256.1 ± 2.0 | 156.9 ± 5.0 | 231.1 ± 4.0 | 162.9 ± 4.0 | 261.1 ± 3.0 |
| CCS | 95.5 ± 5.0 | 180.0 ± 7.0 | 78.3 ± 8.0 | 152.3 ± 7.0 | 88.3 ± 6.0 | 162.3 ± 7.0 |
| CP | 65.0 ± 4.0 | 127.6 ± 2.0 | 55.0 ± 5.0 | 112.0 ± 3.0 | 60.0 ± 2.0 | 120.0 ± 5.0 |

TABLE 20

GF particle size distribution after film redispersion (average and standard deviation over three samples is presented):

| Formulation | Additive | d50 (nm) | d90 (nm) |
|---|---|---|---|
| S | None | 180 ± 5 | 350 ± 5 |
| S1 | SSG | 165 ± 15 | 280 ± 10 |
| S2 | CCS | 169 ± 10 | 285 ± 10 |
| S3 | CP | 185 ± 10 | 290 ± 15 |
| S4 | Pectin | 238 ± 3 | 1700 ± 12 |
| S5 | GG | 180 ± 4 | 285 ± 8 |
| S6 | XG | 234 ± 5 | 960 ± 10 |
| WSMM | — | 160 ± 10 | 240 ± 10 |

Figure 29A:
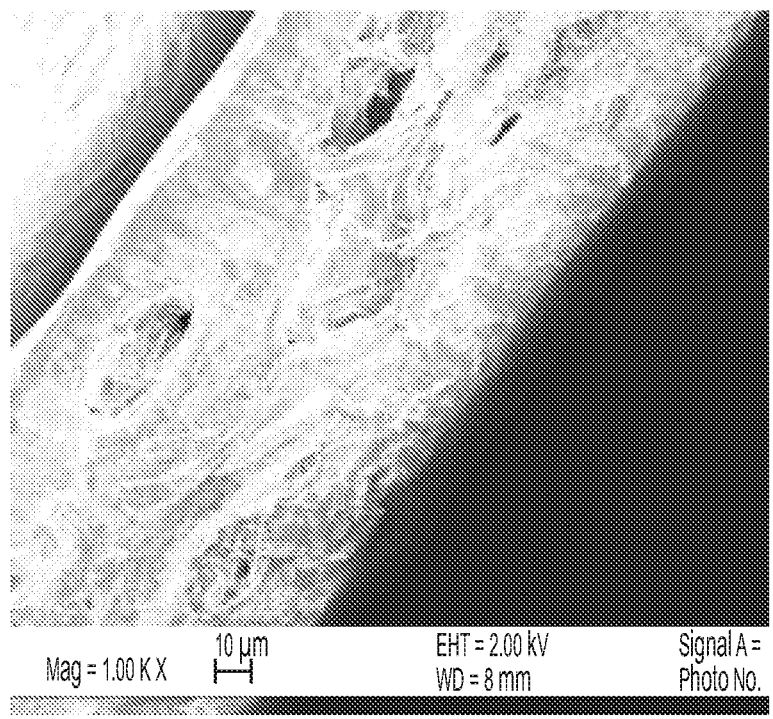
FIG. 29A-D show: (A) cross-sectional SEM images of HPMC film containing swellable SSG and GF nanoparticles, (B) cross sectional image of HPMC film containing swellable CCS particles and GF nanoparticles, (C) cross sectional image of HPMC film containing swellable CP particles and GF nanoparticles, and (D) GF nanoparticles distributed within the HPMC matrix (S1)
Figure 29B:
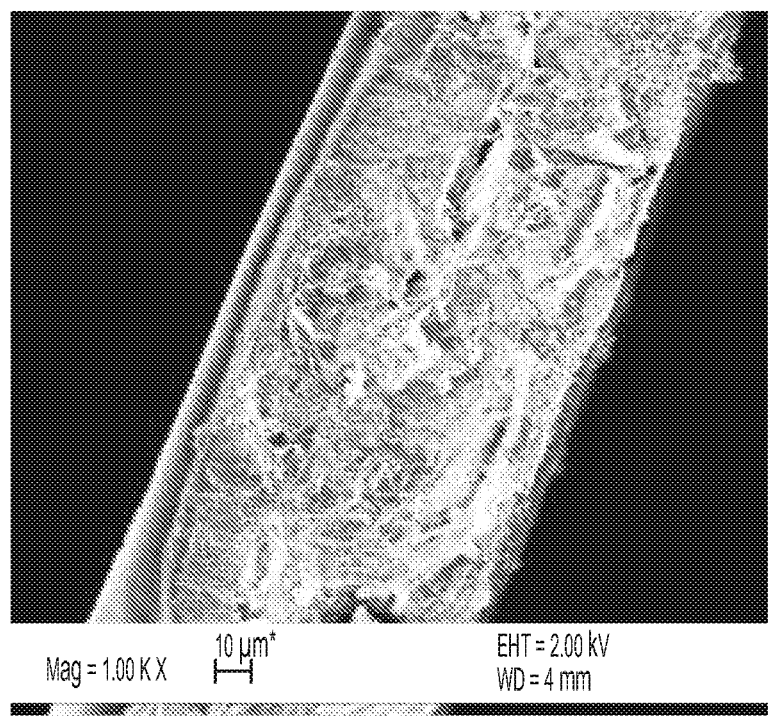
Figure 29C:
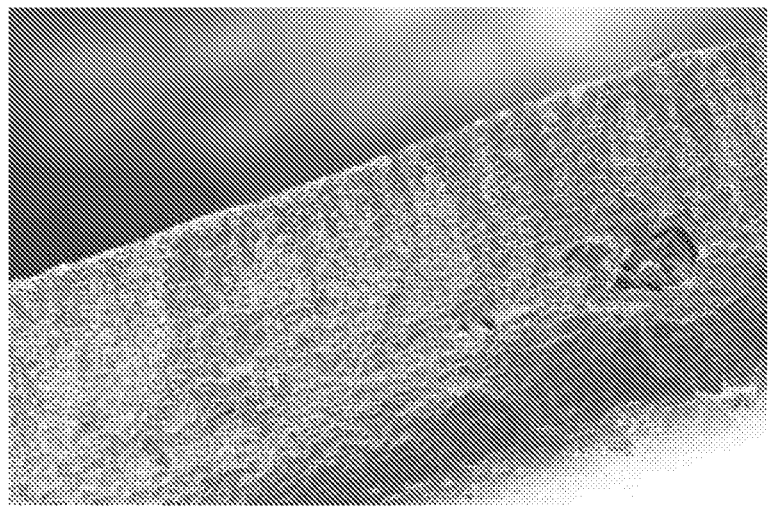
Figure 29D:
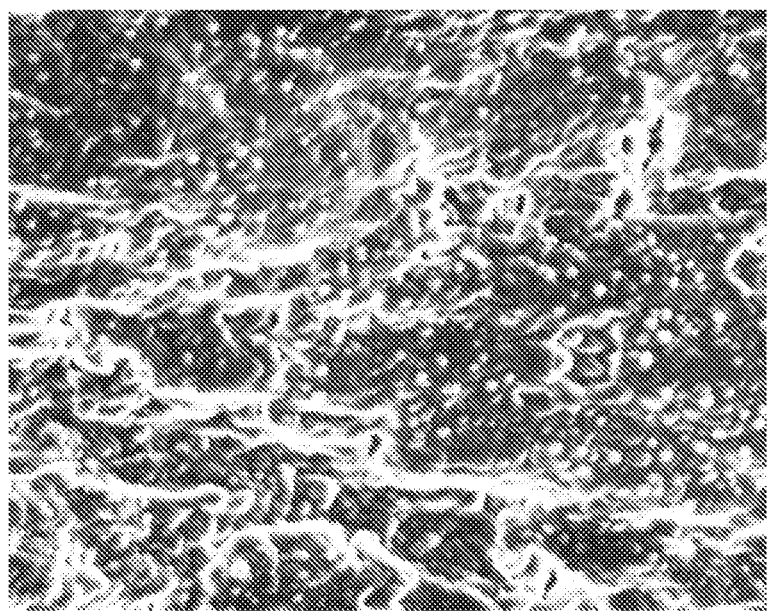

Characterization of Films:

SEM:

FIGS. 29A-D show the SEM images of HPMC films containing GF nanoparticles and micro SDI particles (S1-S3). The presence of swollen SDI particles can be seen in FIGS. 29A-C. The distribution of GF particles in HPMC film containing SSG is shown in FIG. 29D. The GF particles are well distributed without the presence of any aggregates. For other formulations (S4-S6) a slight aggregation of GF was visible.

Figure 30:
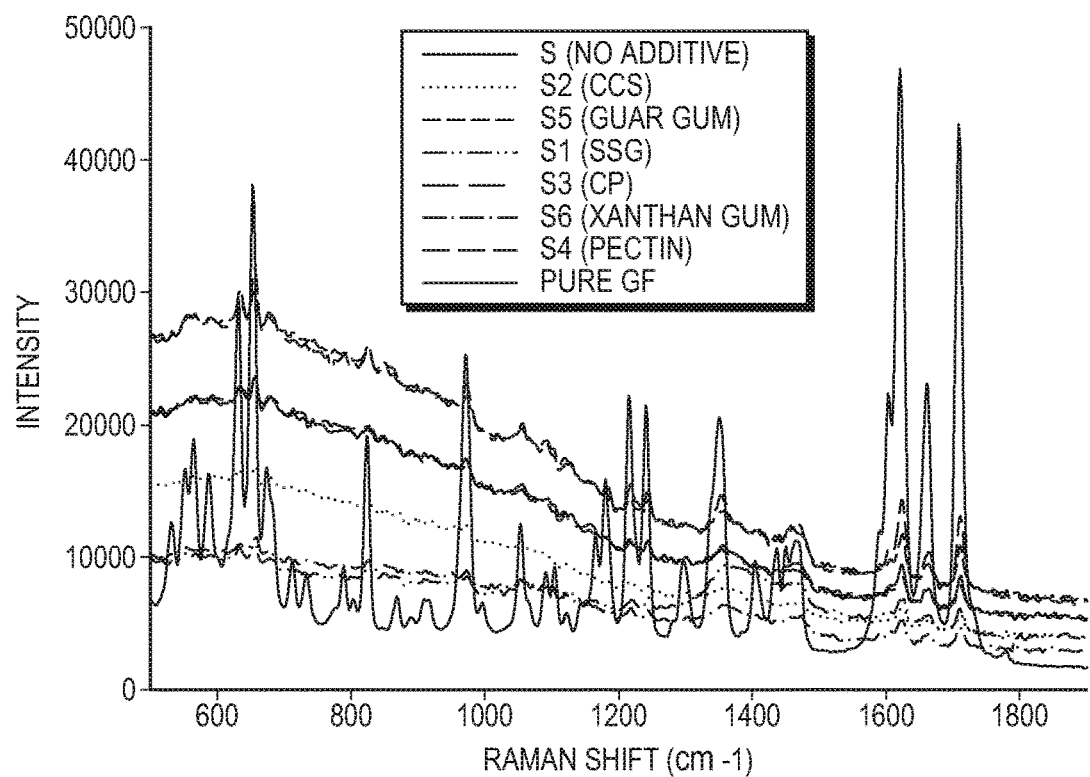
FIG. 30 shows a comparison of Raman spectra for pure GF powder versus GF nanoparticles in films (all seven formulations are shown; no significant difference is observed)
Figure 31:
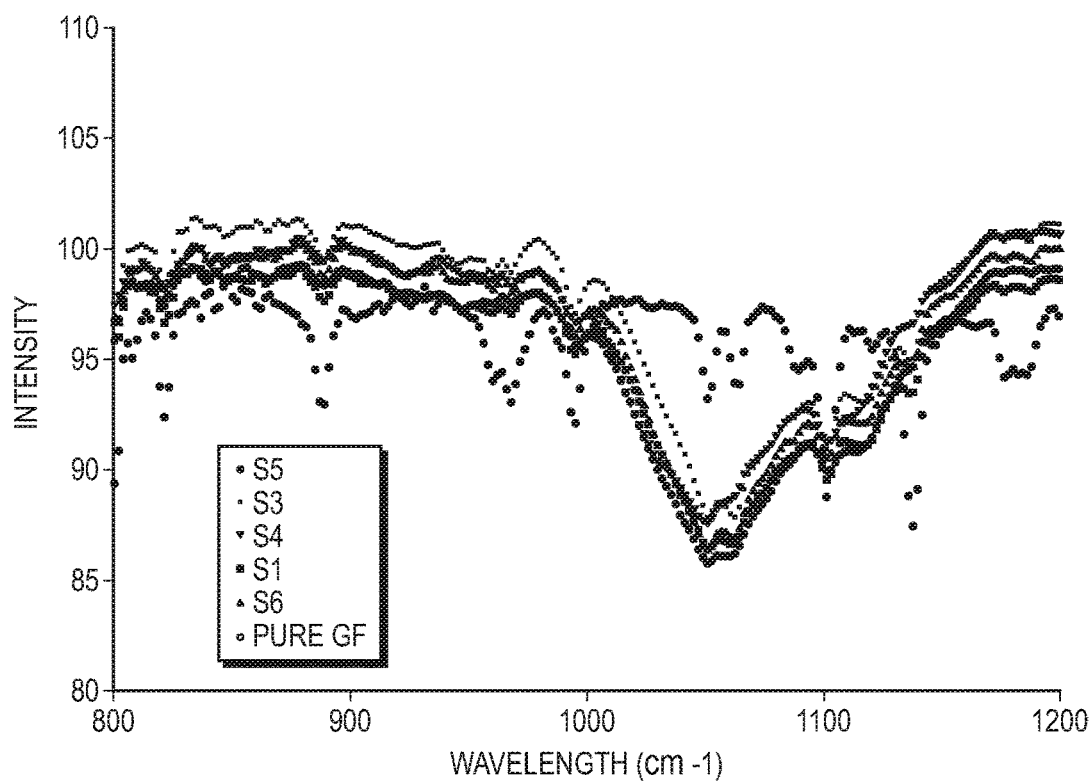
FIG. 31 shows a comparison of FTIR spectra for pure GF powder versus GF nanoparticles in films (all seven formulations are shown; no significant difference is observed)

Raman Spectroscopy and FTIR:

The Raman peak for pure GF (as-received drug) was compared against the GF peak in films for all the seven formulations. The intensity of the peak was reduced due to significant coverage of GF particles with HPMC (FIG. 30). However, there were no significant changes in GF crystallinity. FTIR analysis (FIG. 31) demonstrated that no significant interactions were observed between the HPMC matrix and the GF nanoparticles, which is in agreement with previous observations. Neither SDI particles nor pectin, GG or XG displayed any significant interaction with GF nanoparticles.

Thermo Gravimetric Analysis:

TGA measurements were performed for all the seven compositions (S-S6) with and without GF particles. The presence or absence of GF nanoparticles did not significantly impact the final moisture content in the films, which is in agreement with previous findings. The free water content was found to be between 5-8 wt % and bound water was about 10 wt % for all cases (S-S6). The exposure of samples to 150° C. for 15 min resulted in additional weight loss of about 10-15 wt %. The significant weight loss at 150° C. could be attributed to the presence of glycerin in the film Overall, the addition of SDIs did not result in any additional moisture absorption, thus resulting in low moisture content of films. The low moisture content could also aid in long-term stability of films.

Content Uniformity:

Table 21 shows the average and standard deviation values for the thickness of films and amount of drug per unit area for all formulations. Films made from formulation S had poor content uniformity, which was anticipated due to the low viscosity of the starting precursor solution. The variation in content uniformity for films containing SSG was less than 3% RSD, followed by CCS and CP. These results are also in agreement with the particle size data. Addition of XG, GG and pectin did not lead to uniform films, despite having significantly less variation in film thickness (less than 2% RSD). It is hypothesized that there could have been a phase separation between HPMC and GG, XG or pectin, which could have led to uneven distribution of GF particles. Since gums are known to be pH sensitive, the pH of suspensions S5 and S6 was measured to ensure a pH value of 6.8 to 7 was maintained. Although a few GF aggregates were observed in films containing XG, GG and pectin, no distinct phase separation was observed.

TABLE 21

Content uniformity of GF and thickness variation of film (area of sample tested about 0.712 cm$^2$, average over twelve samples is presented):

| Formulation | Additive | Thickness (μm) | % RSD | Mass of Drug in film (mg) | % RSD |
|---|---|---|---|---|---|
| S | No additive | 98.0 ± 6.0 | 6.0% | 1.47 ± 0.16 | 10.5% |
| S1 | SSG | 100.0 ± 3.0 | 3.0% | 1.51 ± 0.04 | 2.70% |
| S2 | CCS | 100.0 ± 5.0 | 5.0% | 1.52 ± 0.07 | 4.60% |
| S3 | CP | 100.0 ± 5.0 | 5.0% | 1.48 ± 0.09 | 6.15% |
| S4 | Pectin | 102.5 ± 1.4 | 1.8% | 1.60 ± 0.12 | 7.5% |
| S5 | Guar gum | 100.5 ± 1.4 | 1.4% | 1.47 ± 0.13 | 8.84% |
| S6 | Xanthan gum | 100.5 ± 1.4 | 1.4% | 1.49 ± 0.12 | 8.10% |

Mechanical Properties:

The mechanical properties of the final dosage unit are important not only for aesthetic purpose but also because it can affect the release kinetics of drug. Table 22 gives the mechanical properties of all the seven formulations. The incorporation of SDIs does not significantly affect the tensile and yield strength of HPMC film (S versus S1-S3). The addition of pectin, GG and XG leads to significant increase in strength of the film (especially for pectin and XG). This increase in strength leads to delayed disintegration thus resulting in delayed re-dispersion and dissolution of drug particles.

TABLE 22

Mechanical properties of films (average ± standard deviation over six samples is presented):

| Formulation | Additive | Yield stress (MPa) | Ultimate strength (MPa) |
|---|---|---|---|
| S | None | 19 ± 3 | 25 ± 3 |
| S1 | SSG | 20 ± 3 | 26 ± 3 |
| S2 | CCS | 19 ± 3 | 23 ± 3 |
| S3 | CP | 15 ± 3 | 21 ± 3 |
| S4 | Pectin | 29 ± 2 | 45 ± 4 |
| S5 | GG | 23 ± 4 | 33 ± 4 |
| S6 | XG | 23 ± 6 | 38 ± 5 |

Figure 32:
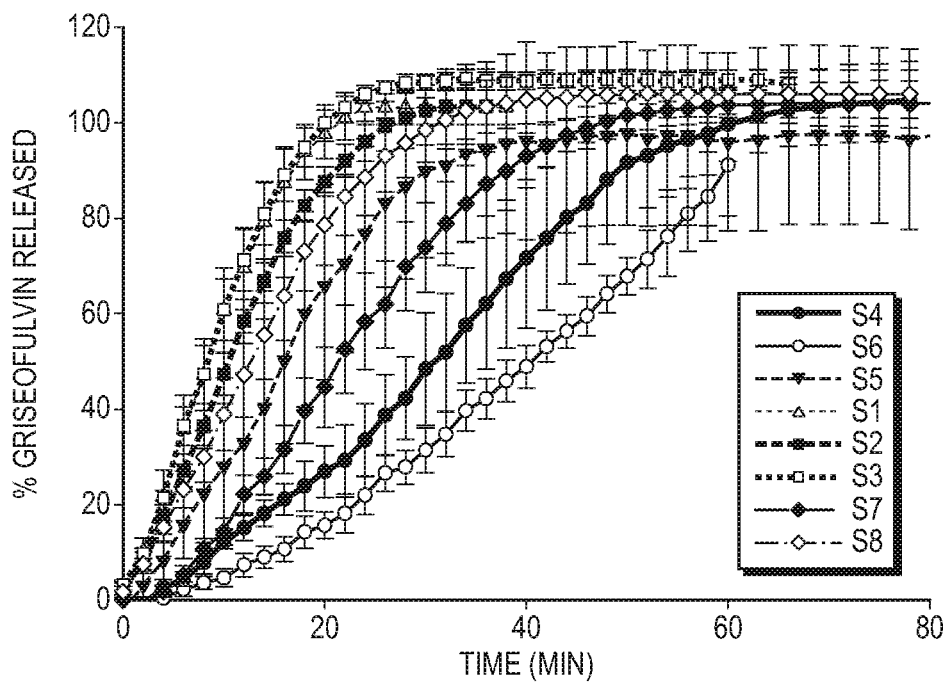
FIG. 32 shows a comparison of GF release profiles from various formulations.
Figure 33:
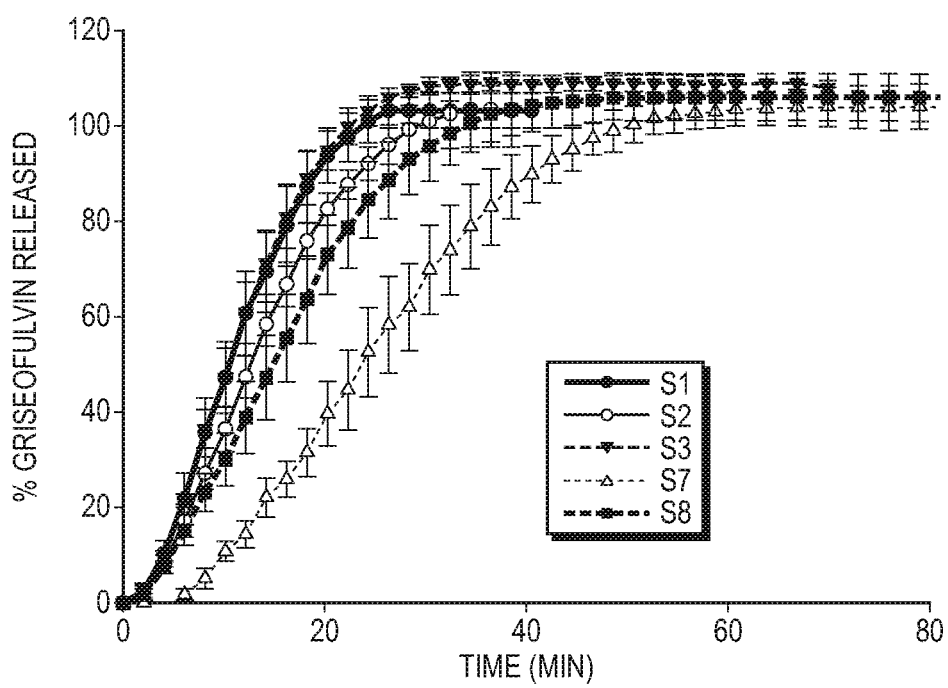
FIG. 33 shows a comparison of GF release profiles from HPMC matrices containing SDIs (SSG, CCS, CP) versus HPMC films made from high molecular weight polymer (HPMC E4M, S7) and HPMC film made with higher polymer concentration (HPMC E15LV, S8)

Dissolution and Drug Release Kinetics:

FIG. 32 shows the dissolution profile for all eight formulations S1-S8. Here, the dissolution profile of S is not included since the film was highly non-uniform and did not provide reliable measurements. Films containing SDIs (S1-S3) demonstrate fast dissolution behavior ($t_{80}$ about 16 mins), whereas films made from formulations S4-S7, displayed a sustained release type of behavior. Films containing gums and pectin swell upon contact with media, which creates a diffusion barrier for the drug resulting in extended drug release. FIG. 33 gives a comparison of dissolution curves for S1-S3 and S7-S8, here the impact of SDIs can be clearly seen, films containing SDIs have faster dissolution rate (statistically significant) than films containing higher concentration of HPMC (E15LV) or high molecular weight HPMC (E4M). It can be concluded that SDIs increase the viscosity of HPMC-GF suspensions without any adverse effects on dissolution rate. The Krosmeyer-Peppas model was found to be a good fit (R2 greater than 0.99) for all cases. The n values for films containing high molecular weight HPMC (E4M, S7) were about 1, implying a zero order release behavior. The value of n for films containing SDIs, pectin, GG and XG was greater than 1, where a combined mechanism of swelling and erosion was responsible for drug release. Calculation of similarity and difference factors demonstrated that significant differences existed between release curves from films containing SDIs (S-S3) versus films containing pectin, GG, XG, high molecular weight HPMC (E4M) and film made from higher concentration of HPM (E15LV) (S4-S8). There were no significant differences in release curves of films containing SSG, CCS or CP. Therefore for the present case the type of SDI added did not have any significant impact on the rate of GF release from films.

Conclusions:

The impact of swelling characteristics of three SDIs (SSG, CCS and CP) on HPMC based film formulations containing GF nanoparticles was investigated. Addition of SDIs resulted in enhancing the viscosity of HPMC-GF suspensions and the swelling capacities of SDIs were found to be comparable with traditionally used swelling agents like pectin, guar and xanthan gum. SDIs had no negative impact on GF crystalinity and did not demonstrate any interaction with HPMC matrix or GF nanoparticles. Through rheology, it was established that addition of SSG led to formation of most stable suspensions, implying lack of nanoparticle agglomeration, which aided in formation of films containing uniform distribution of GF nanoparticles. Films containing SSG also resulted in good particle distribution of GF nanoparticles (upon re-dispersion) and demonstrated fast release of drug.

Example 13: Role of Drug and Surfactant in Stabilization and Dissolution of BCS Class II Drug Nanoparticles in Polymer Strip Films The present disclosure provides that the polymer strip-film platform is evaluated as a means of consistent delivery of stable BCS Class II drug nanoparticles, and the role of surfactant in their stabilization and dissolution has been investigated. Model drugs include fenofibrate (FNB), griseofulvin (GF), naproxen (NPX), phenylbutazone (Pb) and azodicarbonamide (AZD). Films were prepared by casting and drying aqueous mixtures of drug nano-suspensions produced via wet stirred media milling and hydroxypropyl methylcellulose solution containing glycerin as a plasticizer. Film precursor suspensions containing surfactant were about 2000 cP more viscous than without. Polymer alone was sufficient to stabilize FNB, NPX and AZD nanoparticles within the film while surfactant was required for GF and Pb. Drug crystallinity within the film was confirmed via Raman spectroscopy. Films for all drugs containing stable nanoparticles with and without surfactant exhibited good content uniformity (less than 6% RSD for distribution of drug and film thickness). With the exception of GF, all films exhibited similar mechanical properties and USP IV dissolution rate in both SDS and deionized water media, suggesting that the polymer concentration required for film formation is sufficient to mask potential effects of varying drug properties and surfactant.

Polymer films are a robust platform for the successful delivery of several BCS Class II drug nanoparticles. Films with most drugs contained stable, uniformly distributed nanoparticles and exhibited enhanced dissolution. Not all drugs require surfactant for stabilization and enhanced dissolution of drug nanoparticles in polymer films.

With a growing number of new chemical entities classified as poorly water-soluble, successful delivery of poorly water-soluble drugs has become increasingly imperative. One common practice used to improve the dissolution rate and bioavailability of these drugs involves decreasing particle size. Wet stirred media milling (WSMM) has proven to be a robust top-down approach for the production of stable suspensions of drug nanoparticles. Thin polymer films have been demonstrated to be a promising platform for the delivery of drug nanoparticles, but the robustness of this process has not been thoroughly investigated for a wide variety of drugs. In addition, although commonly used for nanoparticle stabilization in suspensions, the role of surfactant in pharmaceutical films is not yet fully understood.

Thanks to improved patient compliance, cost-effective scale-up and continuous processing, as well as the ability to bypass the first pass metabolism in buccal applications, pharmaceutical thin films have garnered a significant amount of attention in recent years. Films offer larger available surface area over traditional dosage forms, allowing for rapid disintegration and dissolution, thereby making polymer films an ideal delivery form for poorly water soluble drugs.

Unlike hot melt extrusion which involves processing under high temperatures known to degrade thermolabile drugs and long-term stability concerns with amorphous drugs, the solvent casting technique offers a reliable film manufacturing method for drugs of varying thermal properties. It has been demonstrated that polymer strip-films are a reliable delivery form for drug nano- and micro-particles engineered from multiple approaches, both bottom-up and top-down. However, such studies focused on only one or a select few drugs, neglecting to demonstrate the robustness of the process for a wide variety of BCS Class II drugs.

Surfactant is known to enhance the dissolution and bioavailability of poorly water-soluble drugs. This effect has also been demonstrated in spray drying and solid dosage forms. In WSMM, surfactants may also be used as stabilizers to prevent freshly milled nanoparticles from aggregating back together during the milling process and storage, particularly in combination with non-ionic steric stabilizers. However, it is unknown to what extent, if any, this stabilization carries over upon incorporation into the polymer matrix of the film, or if the concentration of polymer required for film formation is sufficient to stabilize the drug nanoparticles without the use of surfactant. Although it has been demonstrated that enhanced dissolution of griseofulvin nanoparticles from nano-composites without the use of surfactant, they required the use of co-milled swellable dispersants to achieve fast and reliable nanoparticle recovery. While surfactant is known to aid the stability and delivery of BCS Class II drugs, it is desirable to minimize or eliminate their use to several negative effects. Use of surfactant in disperse systems such as nano-suspensions can promote physical instability and particle growth via Ostwald ripening, especially if the concentration of surfactant is above the critical micelle concentration. Surfactant is also known to cause gastric and pulmonary irritation.

It is a focus of this present disclosure to investigate the stabilization and dissolution of different BCS (biopharmaceutical classification system) Class II drug nanoparticles of varying properties and solubility in polymer films as well as elucidate the role of surfactant in stabilizing and enhancing the dissolution rate of drug nanoparticles within the film. Nano-suspensions of five different BCS Class II drugs were prepared via WSMM with and without surfactant (listed in order of increasing water solubility): fenofibrate (FNB), griseofulvin (GF), naproxen (NPX), phenylbutazone (Pb) and azodicarbonamide (AZD). Polymer solution consisting of low molecular weight hydroxypropyl methylcellulose (HPMC) and glycerin were prepared and shear mixed with drug nano-suspension. The viscosity of the resulting film precursor suspensions was studied using a coaxial cylinder rheometer. Strip films were fabricated via solvent casting technique and dried by a combination of conductive and convective mechanisms. The size distributions of the nanoparticles in suspension and the drug particles re-dispersed from dry films were analyzed via laser diffraction. The morphology of the embedded drug particles and the structure of the polymer matrix of the films were studied using scanning electron microscopy (SEM).

The uniformity of the dry films was examined via assay to determine variation in drug content. Mechanical properties including tensile and yield strength were studied for all film formulations. Drug crystallinity before milling and after incorporation into the dry film was confirmed using Raman spectroscopy. Thermogravimetric analysis (TGA) was employed to analyze the moisture content of the films. Finally, the dissolution rate of drug from the dry films was investigated using a USP IV flow-through cell dissolution apparatus.

Materials & Methods:
Materials:

Fenofibrate (FNB; Jai Radhe Sales, Ahmedabad, India), griseofulvin (GF; Sigma-Aldrich, Saint Louis, Mo.), naproxen (NPX; Medisca, Plattsburgh, N.Y.), phenylbutazone (Pb; Medisca, Plattsburgh, N.Y.) and azodicarbonamide (AZD) were selected as model BCS Class II drugs. Physicochemical properties of the selected drugs are shown in Table 23. Low molecular weight hydroxypropyl methylcellulose (HPMC; Methocel E15 Premium LV, The Dow Chemical Company, Midland, Mich.) was used as a stabilizer and film former. For necessary formulations, sodium dodecyl sulfate (SDS; Fisher Scientific, Pittsburgh, Pa.) was also used as a stabilizer. Glycerin (Sigma-Aldrich, Saint Louis, Mo.) was used as a plasticizer. Drug particle size was reduced via wet stirred media milling (WSMM) as described. All other materials were used without further processing.

TABLE 23

Physicochemical properties of drugs studied:

| Drug | Solubility in water at 4° C. (µg/mL) | Molecular weight (g/mol) | Melting point (° C.) | logP | pK$_a$ |
|---|---|---|---|---|---|
| FNB | 0.7 | 360.8 | 81 | 5.3 | N/A |
| GF | 8.6 | 352.8 | 220 | 2.2 | N/A |
| NPX | 15.9 | 230.3 | 153 | 3.2 | 4.2 |
| Pb | 32.0 | 308.4 | 105 | 3.2 | 4.5 |
| AZD | 35.0 | 116.1 | 225 | 5.8 | 3.9 |

Methods:
Preparation of Drug Nanosuspensions:

Surfactant-free drug nanosuspensions were produced via WSMM utilizing a Netzsch mill (Microcer, Fine particle technology LLC, Exton, Pa.) according to previously established methods. HPMC served as a stabilizer. Suspensions were milled until no appreciable change in particle size was observed. All suspensions consisted of 10% drug (on a w/v basis wrt water) and 2.5% HPMC (wrt drug). After milling, a sample was removed from the holding tank of the mill and dispersed into 15 mL of HPMC stabilizer solution via pipette. The particle size distribution of drug in the sample was then measured using a Coulter LS 13320 Laser Diffraction Particle Size Analyzer (Beckman Coulter, Miami, Fla.).

SDS served as an additional stabilizer for the corresponding surfactant-containing formulations. These suspensions contained 0.5% SDS (wrt drug) in addition to 2.5% HPMC and were milled until no appreciable change in particle size was observed. The sample removed for sizing was dispersed into 15 mL of HPMC and SDS stabilizer solution.

Preparation of Film Precursor Suspensions:

HPMC polymer solutions were prepared according to Dow protocol. Although films can be made with film precursor slurries with viscosity as low as 100 cP, sufficiently high viscosity (e.g., 5000 to 8000 cP or even more) is necessary to produce a uniform, good quality film. The starting polymer concentration was chosen such that this requirement would be met upon mixing with nano-suspension. Corresponding amounts of HPMC and glycerin were added to water at 90° C. such that the composition of the polymer solution was 17% HPMC and 5% glycerin (on a w/w basis). The polymer solution was then allowed to cool to room temperature under continuous stirring. The polymer solution was then shear mixed with drug nano-suspension in a 2:1 ratio by mass at approximately 120 rpm for 6-12 hours using a motor driven dual-propeller mixer (McMaster-Carr, USA). In the case of placebo films X1 and X2, the appropriate drug-free stabilizer solution was used instead of drug nano-suspension. The composition of the resulting polymer-nanosuspension mixtures, hereafter referred to as film precursor suspensions, are listed in Table 24.

TABLE 24

Composition of film precursor suspensions:

| Sample (Nanosuspension) | Drug | wt % drug | wt % HPMC | wt % Glycerin | wt % SDS |
|---|---|---|---|---|---|
| X1 | N/A | 0.0 | 12.1 | 3.3 | 0.00 |
| X2 | N/A | 0.0 | 12.1 | 3.3 | 0.15 |
| F1 | FNB | 3.0 | 12.1 | 3.3 | 0.00 |
| F2 | FNB | 3.0 | 12.1 | 3.3 | 0.15 |
| G1 | GF | 3.0 | 12.1 | 3.3 | 0.00 |
| G2 | GF | 3.0 | 12.1 | 3.3 | 0.15 |
| N1 | NPX | 3.0 | 12.1 | 3.3 | 0.00 |
| N2 | NPX | 3.0 | 12.1 | 3.3 | 0.15 |
| P1 | Pb | 3.0 | 12.1 | 3.3 | 0.00 |
| P2 | Pb | 3.0 | 12.1 | 3.3 | 0.15 |
| A1 | AZD | 3.0 | 12.1 | 3.3 | 0.00 |
| A2 | AZD | 3.0 | 12.1 | 3.3 | 0.15 |

Suspension Rheology:

In order to observe the effect of drug and surfactant on viscosity, the apparent shear viscosity of film precursor suspensions was measured using an R/S-CC+ Coaxial Cylinder Rheometer (Brookfield Engineering, Middleboro, Mass.) equipped with a shear rate controlled coaxial cylinder (CC25) and Lauda Eco water jacket assembly (Lauda-Brinkmann LP, Delran, N.J.) for temperature control. Film precursor suspensions were subjected to a low shear rate program (0-20 $s^{-1}$) at 25±0.5° C. to measure low shear viscosity. Raw data was analyzed using Rheo 3000 software (Brookfield Engineering, Middleboro Mass.) to obtain apparent viscosity as a function of shear rate. All experiments were performed in quadruplicate and results are reported as an average and standard deviation.

Preparation of Polymer Films Containing Drug Nanoparticles:

For each film, approximately 8-9 g of film precursor suspension was manually cast onto a stainless steel substrate at room temperature using a casting knife (Elcometer, MI). The casting thickness was fixed at 1000 μm and the final dimensions of the films were approximately 8 cm×9 cm. The wet films were then dried at 50° C. in the third zone of a Lab-Cast Model TC-71LC Tape Caster (HED International, NJ) in batch mode under laminar air flow for a period of one hour. The dry films were peeled from the substrate and stored in individual sealed plastic bags at room temperature for characterization within days of preparation.

Particle Size Analysis:

The size distribution of drug particles in suspension was measured immediately after milling and re-dispersed from films using a Coulter LS 13320 Laser Diffraction Particle Size Analyzer (Beckman Coulter, Miami, Fla.). Particle size measurement of drug nanoparticles in suspension is described herein. To re-disperse drug particles from films, circular punches of film of about 0.71 $cm^2$ in area were vortex mixed in 3 mL of DI water for 3-5 minutes. To combat the higher solubility of some drugs, additional punches were required to achieve a measurable signal (1 for FNB, 3 for GF, 7 for NPX, 10 for Pb and AZD).

Film Characterization:

Determination of Drug Content and Uniformity:

Ten circular samples of about 0.71 $cm^2$ in area were punched from each film and dissolved in 250 mL of 5.4 mg/mL SDS solution under continuous stirring for a minimum of 3 hours. A Thermo Scientific Evolution 300 UV-Vis spectrophotometer (Thermo Fisher Scientific Inc., MA) was used to measure the UV absorbance of each sample using the appropriate wavelength of maximum absorbance for each drug (290 nm for FNB, 291 for GF, 272 nm for NPX, 264 nm for Pb, 245 nm for AZD) and the concentration of each sample was calculated using a corresponding calibration curve. The average drug weight per unit area and relative standard deviation were calculated for each set of 10 samples.

Dissolution and Drug Release Kinetics:

Use of the USP IV flow-through cell dissolution apparatus for effective discrimination of nanoparticle-loaded polymer films has been previously demonstrated. A flow-through cell dissolution apparatus (USP IV; Sotax, Switzerland) with cells of 22.6 mm internal diameter and 0.2 μm Pall HT Tuffryn filters was employed for all dissolution tests (previous work has shown that use of 0.1 μm filters instead of 0.2 μm filters had no significant impact on the release profiles of films containing drug nanoparticles with mean diameter as low as 160 f 30 nm). Circular film samples of about 0.71 $cm^2$ in area were secured horizontally inside the cells within 5 g of glass beads 1 mm in diameter. Cell temperature was maintained at 37.0±0.5° C. and dissolution media was circulated at a flow rate of 16 mL/min. Two dissolution media were employed for comparison, each using 100 mL per cell: 5.4 mg/mL SDS solution (USP recommended for griseofulvin, for which these methods were established and deionized (DI) water as a surfactant-free medium. The average drug release across six samples from each film was plotted as a function of time.

Thermogravimetric Analysis (TGA):

The melting point and heat of fusion of the drug in the dry films were determined using a Mettler-Toledo POLYDSC (Mettler Toledo, Inc., Columbus, Ohio). A film sample about 0.71 $cm^2$ in area was placed in a sealed perforated aluminum pan and heated under nitrogen flow from 25° C. to 250° C. at a rate of 10° C./min.

Mechanical Properties:

A TA-XT Plus Texture Analyzer (Stable Microsystems, UK) was used to observe the effect of drug and surfactant on the mechanical properties of the films. Tensile and yield strength, elastic modulus and elongation at break were computed from the stress versus strain data. 3-5 rectangular strips with dimensions of 50 mm×15 mm were cut from a single film for testing. The strip was held in place between two grips and stretched at a test speed of 1 mm/s until the breaking point (e.g., tensile failure). The average and standard deviation were computed over all samples and tabulated for each film.

Scanning Electron Microscopy (SEM):

A field emission scanning electron microscope (FESEM) LEO1530VP GEMINI (Carl Zeiss, Inc., Peabody, Mass.) was used to examine the polymeric (network) structure and to observe the presence of any drug aggregates within the films. A small sample of the film was placed on an aluminum stub using carbon tape and carbon coated using a sputter coater prior to imaging. The cross sectional image of all films and surface image of select films were recorded.

Figure 34:
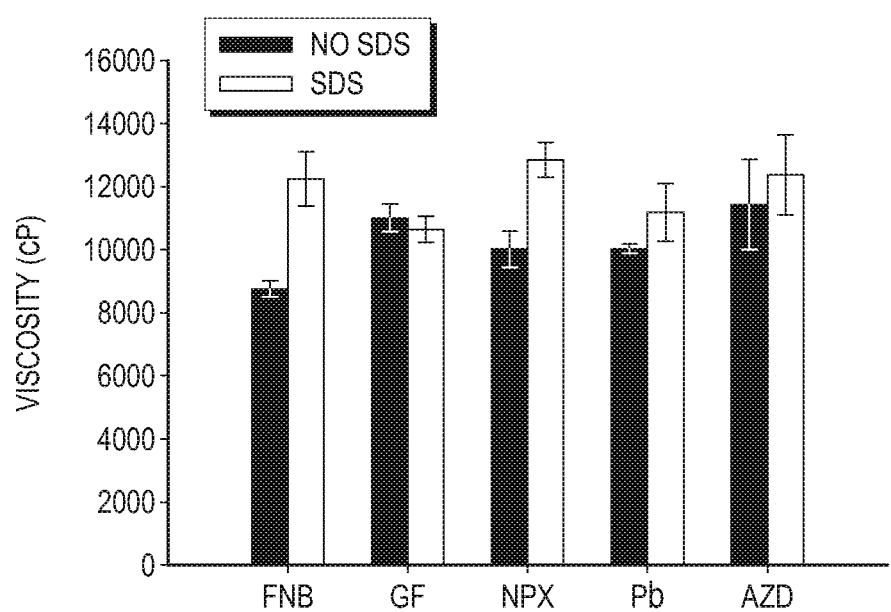
FIG. 34 shows low shear (2.2 s-1) viscosity of film precursor suspensions at room temperature.
Figure 35A:
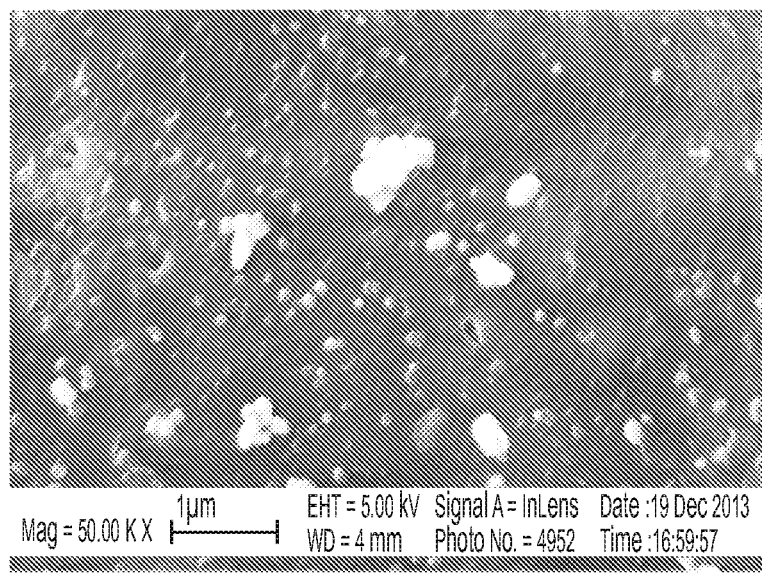
FIGS. 35A-F show cross-sectional SEM images of films containing: (A,B) GF, (C,D) NPX, (E,F) Pb and (G,H) AZD nanoparticles without SDS and with SDS, respectively.
Figure 35B:
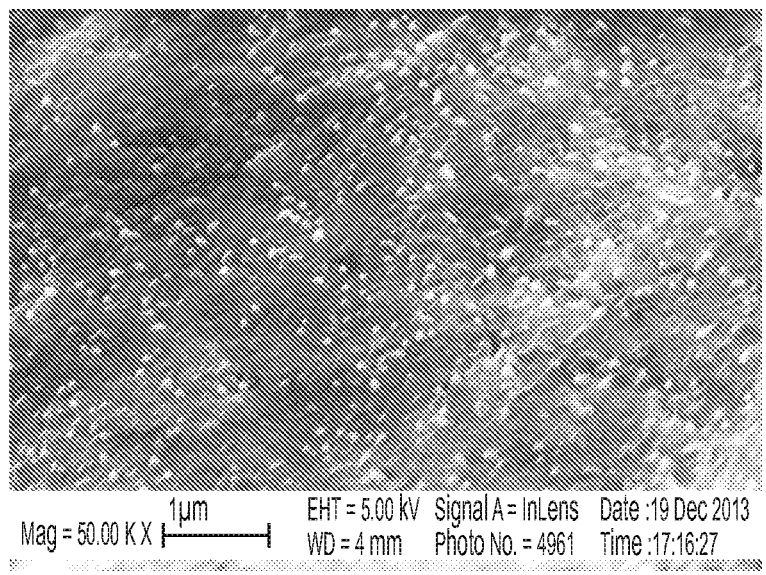
Figure 35C:
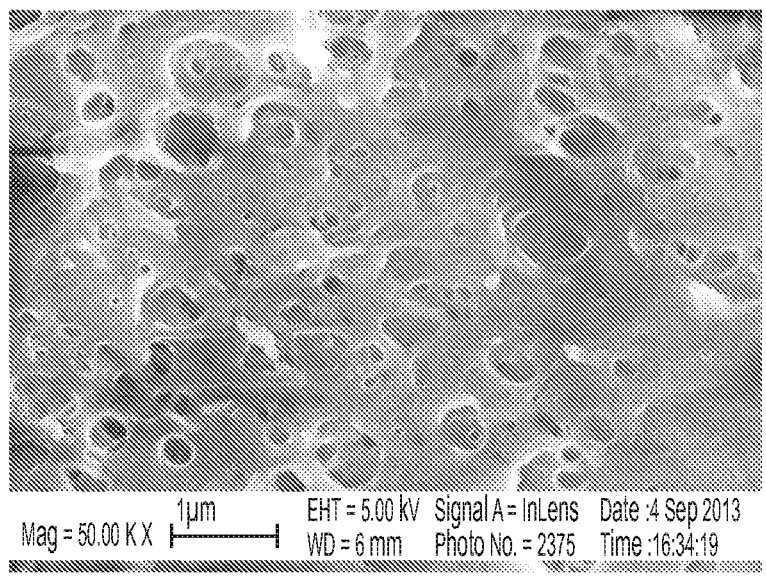
Figure 35D:
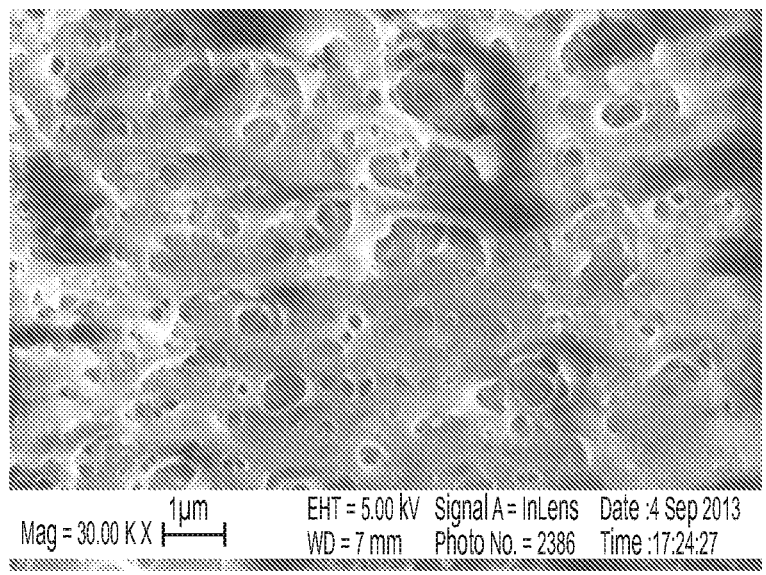
Figure 35E:
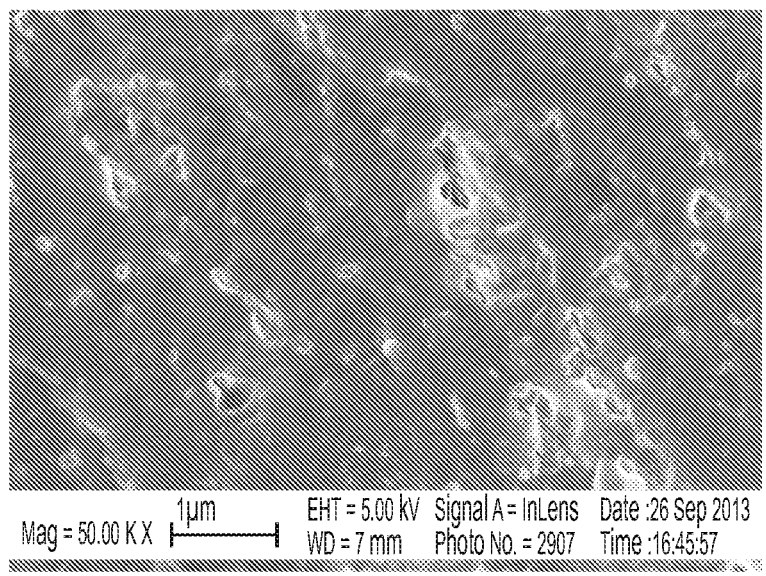
Figure 35F:
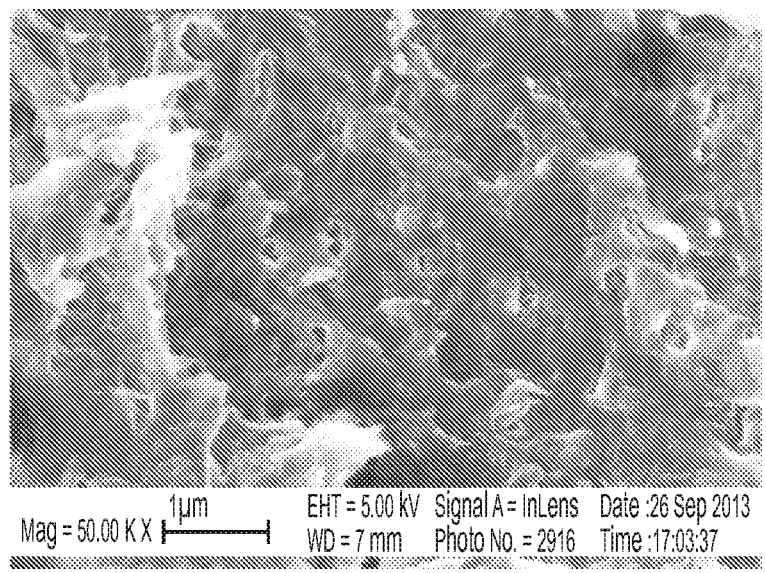
Figure 35G:
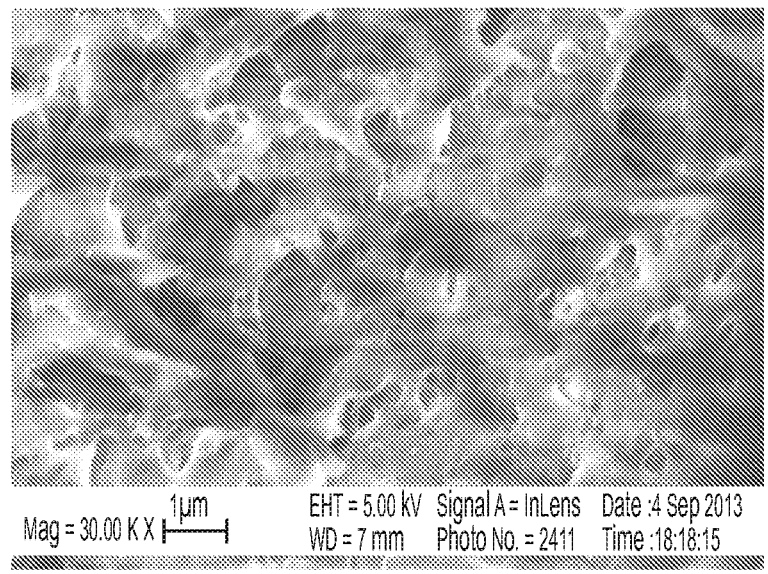
Figure 35H:
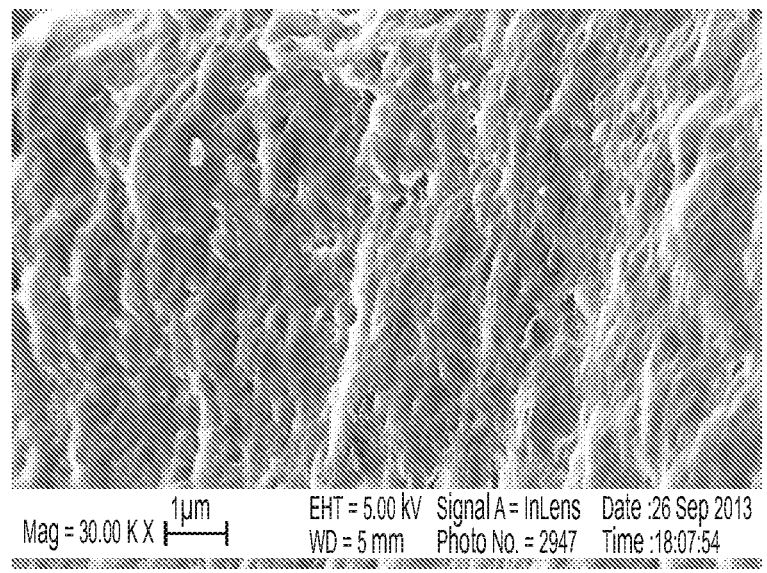

Raman Spectroscopy:

To ensure drug crystallinity within the dry films, Raman studies were performed using an EZRaman LE Raman Analyzer system (Enwave Optronics, Irvine, Calif.) with an HRP 8 high throughput fiber probe coupled to a MicroView adapter with a 10× objective 10 µm spot size. A 250 mW 785 nm was used for measurements on pure drug powder and for film samples. Raman spectra were collected every 15 s with an average of 5 scans Results and Discussion: Rheological Studies:

Viscosity of the film precursor suspension has been shown to have a significant impact on the content uniformity of the resulting dry film FIG. 34 shows the apparent shear viscosity of all film precursor suspensions at low shear rate (2.2 $s^{-1}$). Surfactant-free film precursor suspension viscosities ranged from about 9,000-11,000 cP, while those of SDS formulations ranged from 11,000-13,000 cP.

Lack of significant variation in viscosity across all five drugs suggests that the drug itself has little impact on the rheological properties of the film precursor suspension given the high concentration of polymer. FNB showed the greatest increase in viscosity with the addition of surfactant, followed by NPX, Pb, AZD and GF, which showed no statistical difference. This phenomenon has also been reported in more dilute systems, implying that a similar effect is present under the viscous conditions required for film formation. It has been observed that a general increase in viscosity and viscoelasticity of aqueous PEO solutions as SDS concentration was increased, but none of the formulations exceeded 30 cP in viscosity. Also observed was a viscosity increase with increasing SDS concentration (up to 13 mM) for weakly hydrophobic 0.5% (w/w) HPMC solutions.

Particle Size Analysis:

Nano-milled BCS Class II drugs have been shown to exhibit enhanced bioavailability thanks to the increased specific surface area of the drug particles. Consequently, it is desired that the drug particles retain their nano-size upon incorporation into and re-dispersion from films, thereby preserving their enhanced bioavailability upon delivery. Particle size distribution data for drug particles in WSMM suspension prior to shear mixing with polymer solution is given in Table 25 and for drug particles re-dispersed from dry films in Table 26. It should be noted that, despite being subjected to identical milling conditions, FNB, GF, Pb and AZD all yielded smaller particle sizes with surfactant than without, particularly with GF. This behavior was expected, as the addition of surfactant as a stabilizer for WSMM has been shown to aid in polymer adsorption on the particle surface, generally yielding smaller particle sizes. In addition, the significant fraction of particles between 1-2 µm in the AZD suspensions may be attributed to its higher solubility in water relative to the other drugs used in this study.

Although the median particle size of the WSMM suspensions ranged from 70-400 nm across most formulations, it will be demonstrated below that particle size variation within this range has no significant impact on the dissolution rate of the resulting films. Thus, the primary concern is ensuring that the drug nanoparticles do not experience any agglomeration during film production. Films containing FNB, NPX and AZD did not exhibit a significant change in particle size upon incorporation into films for both SDS and SDS-free formulations, demonstrating the ability of the polymer matrix to stabilize these drug nanoparticles with and without the aid of surfactant. Re-dispersion from P1 yielded agglomerates, whereas re-dispersion from P2 yielded nanoparticles. Re-dispersion from both GF films yielded nanoparticles despite agglomeration in the surfactant-free suspension. All drug particle re-dispersion results were confirmed visually via SEM.

TABLE 25

Particle size distribution of drug in suspension prior to shear mixing with polymer solution:

| Formulation | F1 | F2 | G1 | G2 | N1 | N2 | P1 | P2 | A1 | A2 |
|---|---|---|---|---|---|---|---|---|---|---|
| $d_{10}$ (nm) | 160 | 67 | 150 | 123 | 76 | 70 | 102 | 113 | 235 | 181 |
| $d_{50}$ (nm) | 280 | 178 | 1,460 | 161 | 141 | 136 | 156 | 176 | 370 | 278 |
| $d_{90}$ (nm) | 503 | 417 | 5,178 | 214 | 246 | 313 | 254 | 282 | 1,719 | 1,831 |

TABLE 26

Particle size distribution of drug redispersed from dry film:

| Formulation | F1 | F2 | G1 | G2 | N1 | N2 | P1 | P2 | A1 | A2 |
|---|---|---|---|---|---|---|---|---|---|---|
| $d_{10}$ (nm) | 151 | 135 | 103 | 109 | 75 | 68 | 100 | 94 | 229 | 222 |
| $d_{50}$ (nm) | 275 | 283 | 238 | 164 | 138 | 134 | 5,496 | 184 | 366 | 352 |
| $d_{90}$ (nm) | 489 | 620 | 491 | 269 | 248 | 359 | 63,004 | 430 | 1,744 | 1,685 |

Film Characterization:
Content Uniformity:

The average and relative standard deviation (RSD) for film thickness, drug mass per unit area of film and drug loading on a w/w basis for all formulations are shown in Table 27. AZD exhibited the least variation in thickness and drug distribution (about 3% RSD), followed by FNB, NPX, GF and Pb, which exhibited the most variation (up to 10% RSD). The unusually large variation in P1 is likely a result of drug particle agglomeration during film production, which is known to lead to poor content uniformity. However, no universal trend between drug particle size and content uniformity could be established for films containing stable drug nanoparticles. In addition, the addition of surfactant into the film did not have a consistent effect on content uniformity. Although NPX, Pb and AZD films exhibited less variation in drug distribution with SDS than without, GF and FNB films exhibited greater variation with SDS than without. Overall, the variation in drug distribution of surfactant-free films was 4.5% RSD and thickness variation was 2.9% RSD, demonstrating the feasibility of producing uniform films loaded with drug nanoparticles without the need for surfactant. Films containing surfactant exhibited comparable variation in drug distribution (4.4% RSD) and in thickness (2.6% RSD), suggesting that the amount of surfactant required to stabilize the drug nanoparticles in suspension does not influence the content uniformity of films made from those suspensions, positively or negatively.

TABLE 27

Content uniformity and thickness variation within films:

| Formulation | F1 | F2 | G1 | G2 | N1 | N2 | P1 | P2 | A1 | A2 |
|---|---|---|---|---|---|---|---|---|---|---|
| Thickness (μm) | 92.8 | 102.0 | 92.9 | 97.9 | 101.5 | 108.3 | 107.8 | 93.4 | 98.8 | 92.6 |
| RSD % | 2.4% | 1.4% | 2.4% | 5.5% | 5.4% | 0.8% | 2.2% | 3.8% | 2.1% | 1.4% |
| Drug mass per unit area (mg/cm$^2$) | 1.71 | 2.08 | 1.95 | 1.98 | 1.53 | 1.84 | 1.12 | 1.38 | 1.97 | 2.00 |
| RSD % | 2.8% | 4.2% | 1.8% | 5.9% | 5.0% | 3.1% | 10.1% | 6.3% | 3.1% | 2.7% |
| wt % drug | 14.9 | 17.0 | 15.2 | 14.5 | 12.7 | 14.2 | 9.2 | 11.0 | 16.6 | 17.7 |
| RSD % | 2.0% | 2.6% | 1.3% | 1.3% | 1.6% | 1.6% | 7.1% | 5.1% | 2.2% | 0.7% |

Mechanical Properties:

In addition to the importance of having flexible films with sufficient mechanical strength, the mechanical properties of films have also been demonstrated to influence dissolution kinetics. The tensile strength (TS), yield strength (YS), elastic modulus (EM) and elongation at break for all film formulations are shown in Table 28. GF exhibited the overall strongest TS, YS, highest EM and shortest percent elongation of all drugs, resulting in slowed dissolution. Interestingly, although placebo films with SDS exhibited significantly lower TS and elongation than those without SDS, no significant difference was observed between SDS and SDS-free films containing drug. It is thought that the introduction of drug into the system has a greater impact on the mechanical properties of the film than the surfactant at these concentrations, masking this effect.

TABLE 28

Mechanical properties of films:

| Formulation | Tensile strength (MPa) | Yield strength (MPa) | Elastic modulus (MPa) | Elongation at break (%) |
|---|---|---|---|---|
| X1 | 36.8 ± 0.8 | 25.3 ± 1.1 | 18.8 ± 0.8 | 27.6 ± 1.2 |
| X2 | 26.1 ± 1.9 | 23.5 ± 2.0 | 17.2 ± 0.7 | 14.6 ± 3.6 |
| G1 | 42.3 ± 2.2 | 34.4 ± 0.3 | 24.9 ± 1.6 | 20.5 ± 2.8 |
| G2 | 48.8 ± 4.2 | 42.1 ± 2.7 | 27.1 ± 1.2 | 16.9 ± 2.5 |
| N1 | 26.4 ± 3.5 | 22.3 ± 2.1 | 16.1 ± 1.7 | 23.2 ± 3.8 |
| N2 | 35.4 ± 0.6 | 29.4 ± 1.0 | 21.2 ± 0.9 | 23.4 ± 2.0 |
| P1 | 31.1 ± 1.0 | 27.4 ± 0.7 | 19.6 ± 0.7 | 20.4 ± 1.9 |
| P2 | 30.8 ± 2.1 | 26.4 ± 0.4 | 20.6 ± 0.5 | 22.2 ± 1.3 |
| A1 | 29.9 ± 0.2 | 22.1 ± 0.8 | 21.9 ± 1.0 | 25.4 ± 0.6 |
| A2 | 27.5 ± 0.8 | 21.6 ± 0.0 | 21.1 ± 0.7 | 21.4 ± 2.1 |

Figure 36A:
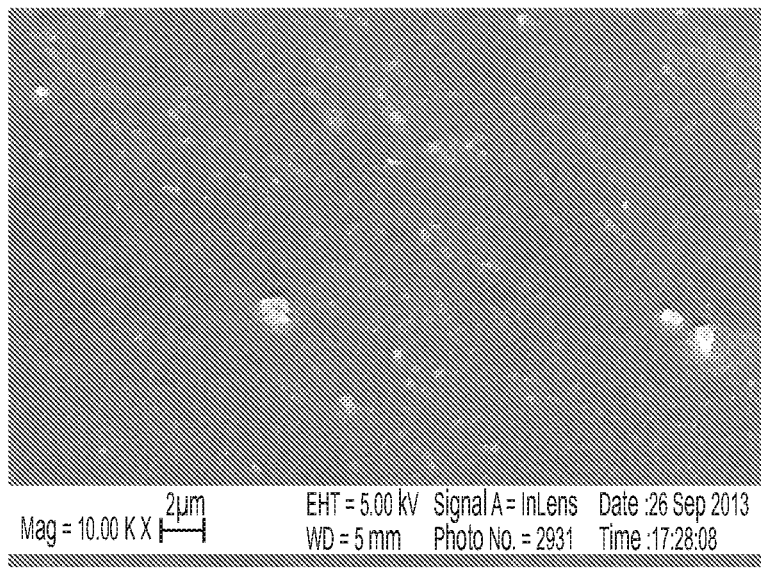
FIGS. 36A-B show SEM surface images of films: (A) P1, and (B) A2.
Figure 36B:
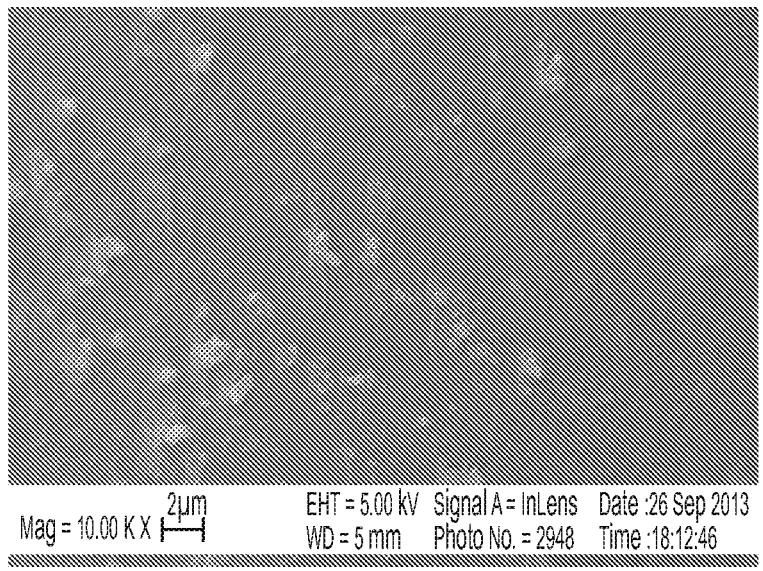

Scanning Electron Microscopy (SEM):

SEM images were taken to qualitatively confirm drug nanoparticle size and morphology within the polymer matrix of the dry films. Cross sectional images for each film are shown in FIGS. 35A-H, and surface images for select films are shown in FIGS. 36A-B. With the exception of GF, no agglomeration was observed in the cross sectional images. In agreement with suspension sizing data, G1 (FIG. 35A) exhibited agglomeration of nanoparticles in the film whereas G2 (FIG. 35B) did not. The ability to recover GF nanoparticles after re-dispersion from the surfactant-free film is indicative of soft agglomerates which are not expected to impact the dissolution rate as they break apart to reform the original nanoparticles under light mechanical forces or hydrodynamic stress. P1 surface images revealed minor agglomeration, although the presence of particles larger than a few microns in size suggested by redispersion could not be visually confirmed (FIG. 36A). Agglomeration was also apparent in AZD films due to the relatively high solubility of the drug in water, although no drug particles larger than the original nanoparticles in suspension could be found in the film (FIG. 36B). These findings confirm the robustness of the film format to stabilize drug nanoparticles formed via WSMM with and without surfactant, as the drug particles observed in every film (excluding P1) were consistent with the size of the drug particles in the suspensions from which they were taken.

Figure 37A:
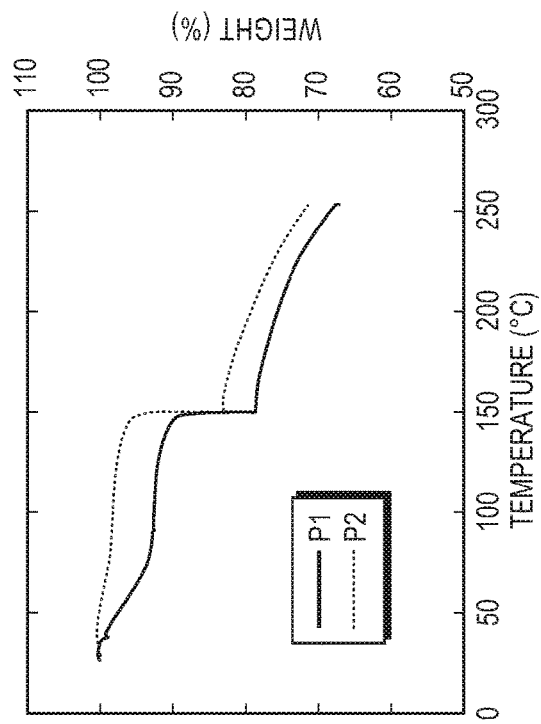
FIGS. 37A-C show normalized TGA curves for: (A) NPX, (B) Pb, and (C) AZD films without SDS and with SDS.
Figure 37B:
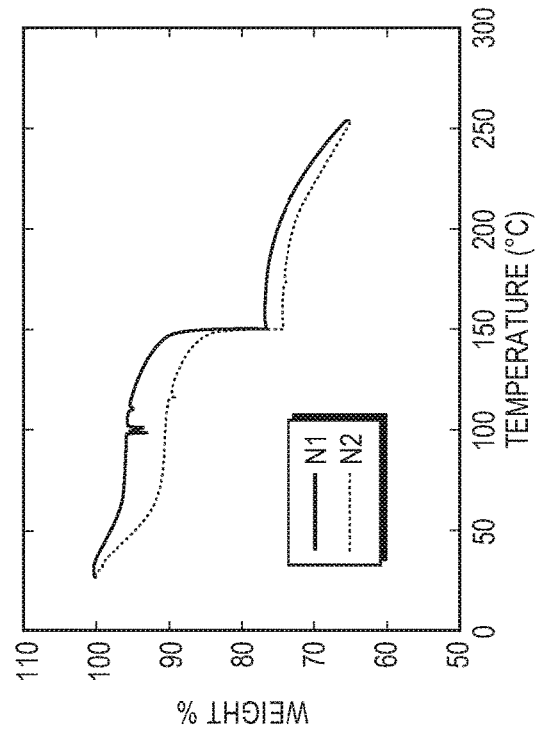
Figure 37C:
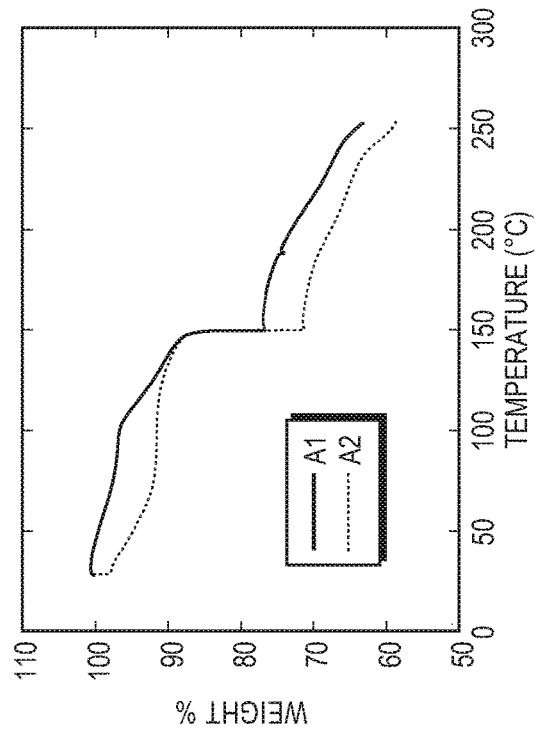
Figure 38A:
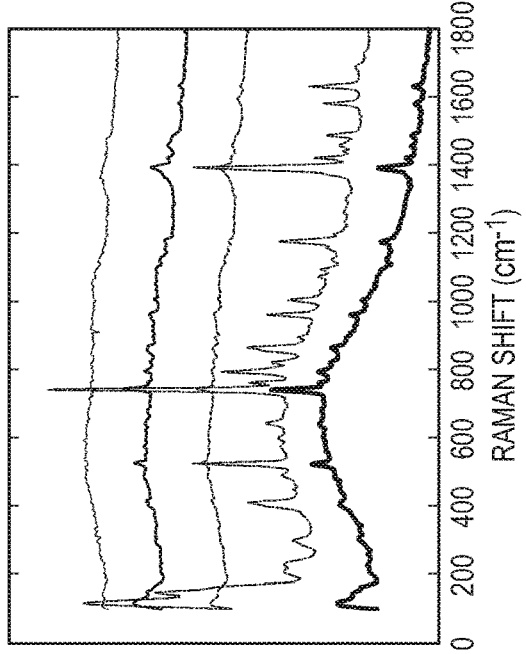
FIGS. 38A-D show Raman spectra of pure drug and films containing: (A) FNB, (B) NPX, (C) Pb, and (D) AZD.
Figure 38B:
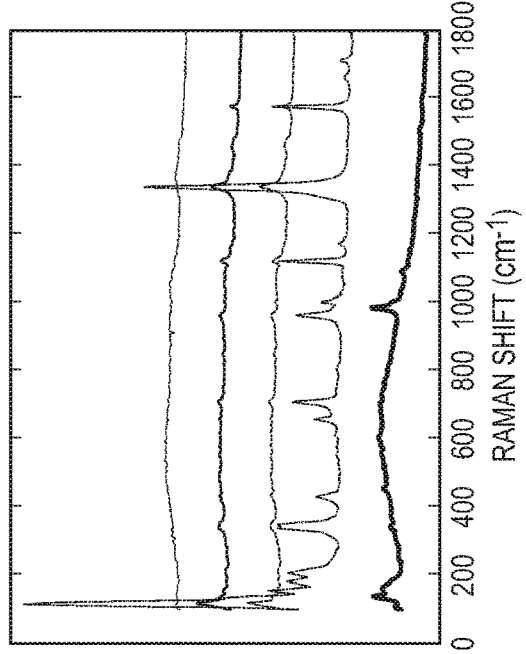
Figure 38C:
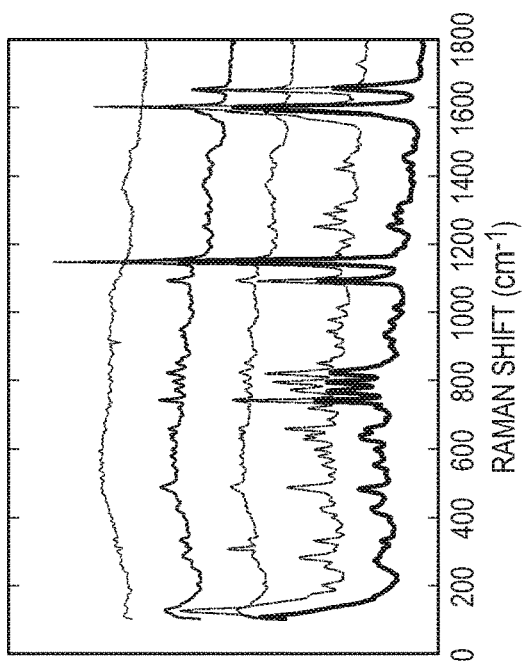
Figure 38D:
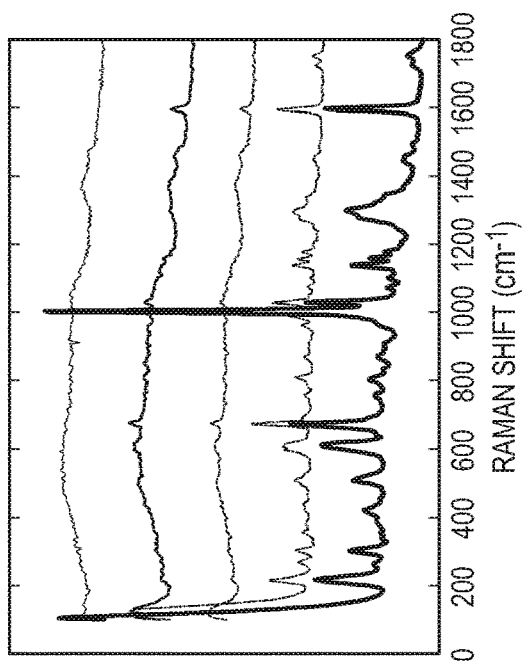
Figure 39A:
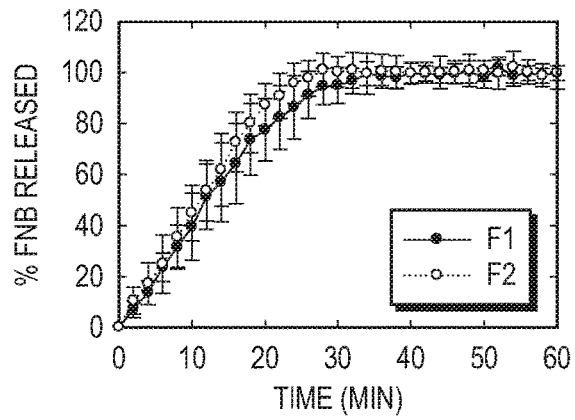
FIGS. 39A-E show comparisons of release profiles from films containing: (A) FNB, (B) GF, (C) NPX, (D) Pb, and (E) AZD in SDS media.
Figure 39B:
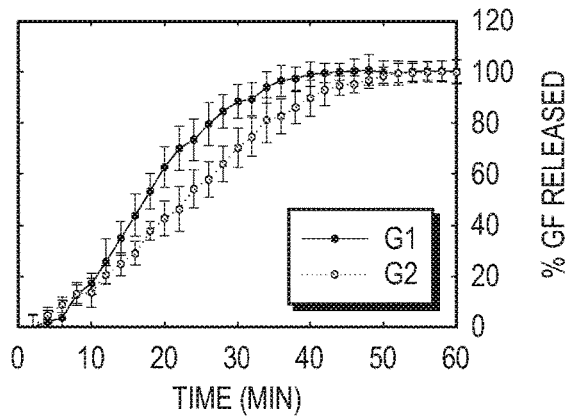
Figure 39C:
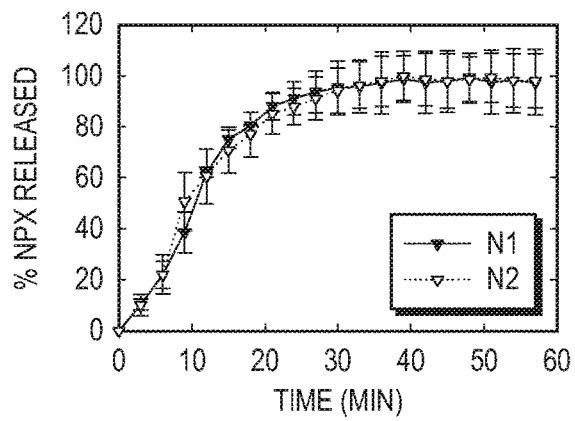
Figure 39D:
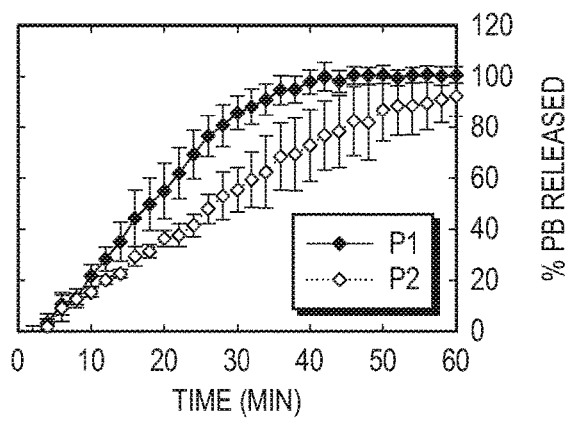
Figure 39E:
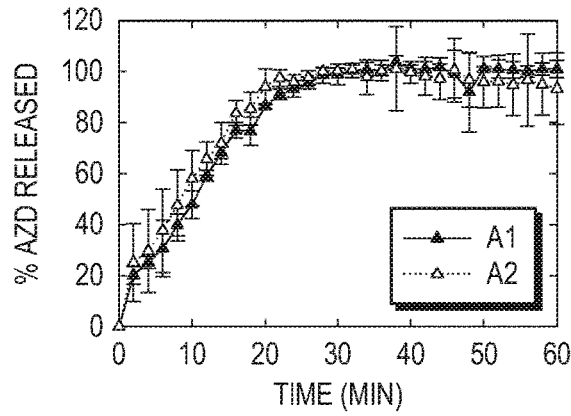

Thermogravimetric Analysis (TGA):

TGA curves were measured for select films and normalized to account for varying drug and SDS content between films (FIGS. 37A-C). Weight loss up to 100° C. was between 2-8 wt % for all films, primarily due to the loss of free or bound water. 15 minute exposure to 150° C. resulted in additional weight loss of 10-15 wt %, mainly attributed to the loss of glycerin in the film.

Raman Spectroscopy

Raman spectroscopy was employed to confirm the crystallinity of the drug within the films. Raman spectra for pure amorphous drug, as-received crystalline drug powder, drug-loaded film without SDS, drug-loaded film with SDS, and placebo film without drug are shown in FIGS. 38A-D. Alignment of the spectral peaks for both drug-loaded films with those of their respective crystalline drug spectra as opposed to those of the amorphous drug spectra demonstrates that the crystallinity of the drug was maintained throughout the film making process for all drugs under investigation.

Figure 40A:
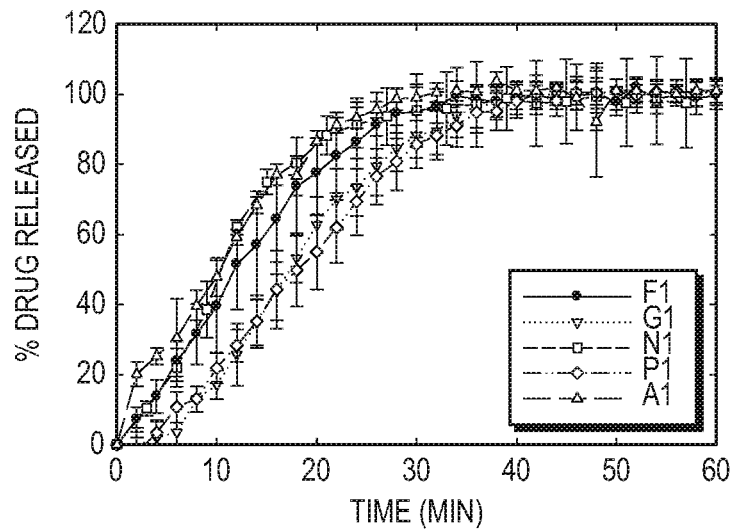
FIGS. 40A-B show comparisons of drug release profiles in SDS media from films: (A) without SDS, and (B) with SDS.
Figure 40B:
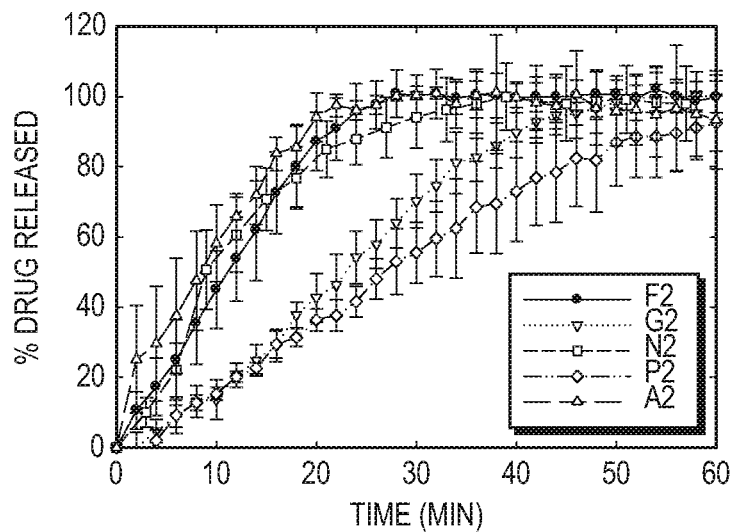

Dissolution and Drug Release Kinetics:

A comparison between the dissolution profiles of films without SDS and with SDS for each of the five drugs in SDS media is shown in FIGS. 39A-E. FNB, NPX and AZD all exhibited statistically similar dissolution profiles with and without SDS according to similarity and difference factors, indicating that the presence of surfactant in the film had little influence on the rate of drug release from the film. This is reinforced by a direct comparison of the dissolution profiles for all five drugs with and without surfactant in FIGS. 40A-B, where differing drug solubility and properties are shown to have little impact on the rate of drug release. The exception to this was GF, which exhibited a more delayed release due to the higher mechanical strength of the resulting films. It is hypothesized that, due to the high polymer concentration necessary for film formation, drug release is limited by erosion of the polymer matrix, masking any potential effects of drug properties or surfactant on dissolution rate.

Figure 41B:
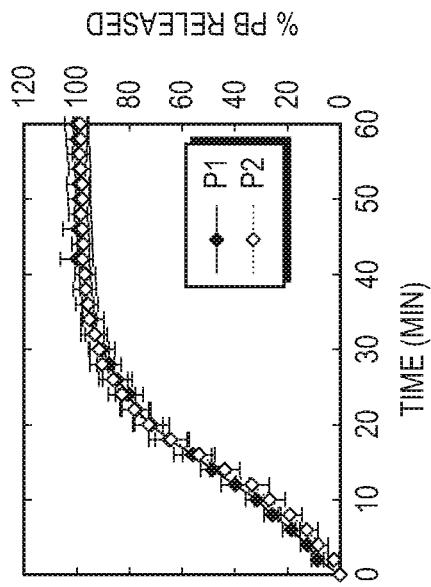
FIGS. 41A-C shows comparisons of release profiles from films containing: (A) NPX, (B) Pb, and (C) AZD in DI water media.
Figure 41A:
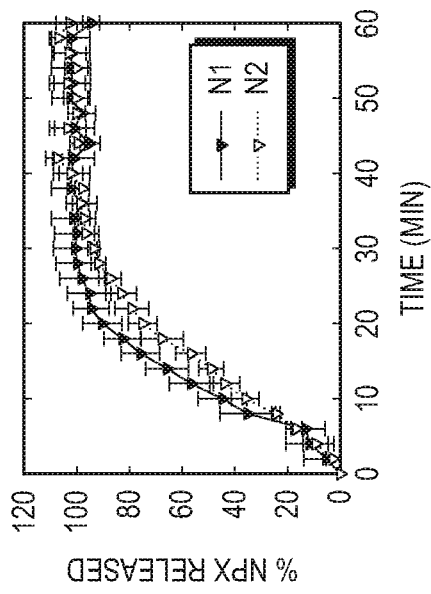
Figure 41C:
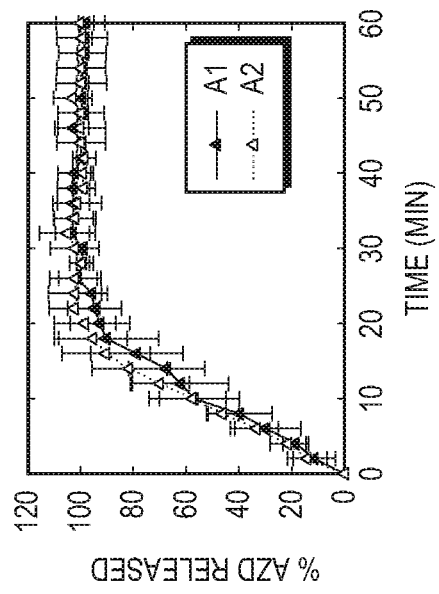
Figure 42A:
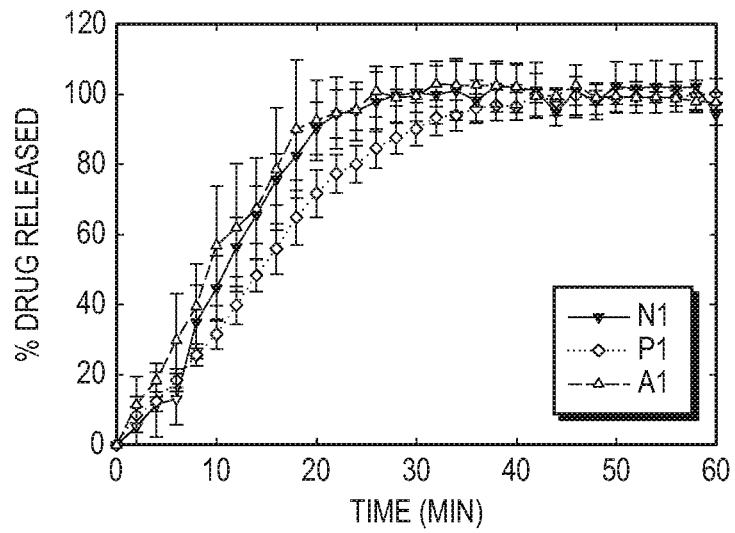
FIGS. 42A-B show comparisons of drug release profiles in deionized water media from films: (A) without SDS, and (B) with SDS.
Figure 42B:
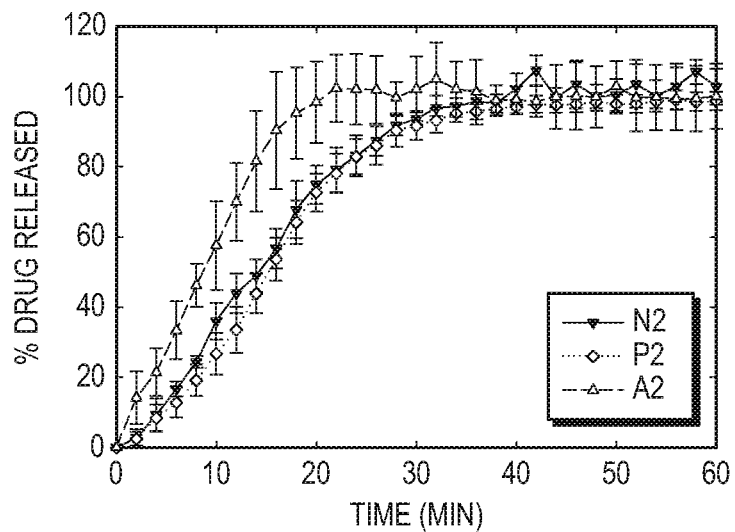

To further magnify the potential impact of surfactant on dissolution, similar tests were performed in DI water media for all films, with the exception of FNB and GF whose solubility in water (8.6 and 0.7 µg/mL, respectively) was too low to make such a test practical. As shown in FIGS. 41A-C, despite being released into a surfactant-free medium, Pb and AZD films exhibited statistically similar dissolution profiles with and without SDS, further emphasizing that surfactant is unnecessary to achieve enhanced dissolution of drug nanoparticles from films. The difference between NPX films may be attributed to the greater mechanical strength of N2 compared to N1, leading to slower dissolution in DI water.

Conclusions:

The robustness of polymer films as a platform for the delivery of BCS Class II drug nanoparticles and the role of surfactant in their stabilization and dissolution were investigated. The presence of SDS in the film precursor suspension resulted in a significant increase in overall viscosity across all five drugs studied. Drug nanoparticle size was maintained upon re-dispersion from FNB, NPX and AZD films with and without SDS, suggesting surfactant is not required to stabilize these drugs within the polymer film. In contrast, agglomerates were observed in Pb and GF films made without SDS, indicating the necessity for surfactant to stabilize them within the film, although the GF agglomerates yielded nanoparticles upon re-dispersion. Nearly all films exhibited good content uniformity in terms of drug distribution and thickness variation, demonstrating that quality films can be made incorporating a variety of BCS Class II drugs. The presence or absence of SDS was found to have little impact on the content uniformity of the films overall. FNB, NPX, Pb and AZD films all exhibited similar mechanical properties with and without SDS, indicating that neither drug nor surfactant had a noticeable impact on the mechanical properties of the film. The exception to this was GF, whose films exhibited greater mechanical strength than the others. TGA revealed no distinct trend between drug or surfactant content and final moisture content of the films. Aside from GF films which released more slowly due to their higher mechanical strength, there was little difference between dissolution profiles for FNB, NPX, Pb and AZD with and without surfactant in both SDS and DI water media, demonstrating that the drug itself and the presence of surfactant had little influence on the dissolution kinetics.

Example 14: Fast Drying of Biocompatible Polymer Films Loaded with Poorly Water-Soluble Drug Nano-Particles Via Low Temperature Forced Convection Fast drying of nano-drug particle laden strip-films formed using water-soluble biocompatible polymers via forced convection was investigated in order to form films having uniform drug distribution and fast dissolution. Films were produced by casting and drying a mixture of poorly water soluble griseofulvin (GF) nanosuspensions produced via media milling with aqueous hydroxypropyl methylcellulose (HPMC E15LV) solutions containing glycerin as a plasticizer. The effects of convective drying parameters, temperature and air velocity, and film-precursor viscosity on film properties were investigated. Two major drying regimes, a constant rate period as a function of the drying conditions, followed by a single slower falling rate period, were observed. Films dried in an hour or less without any irreversible aggregation of GF nanoparticles with low residual water content. Near-infrared chemical imaging (NIR-CI) and the content uniformity analysis indicated a better drug particle distribution when higher viscosity film-precursors were used. Powder X-ray diffraction showed that the GF in the films retained crystallinity and the polymorphic form. USP IV dissolution tests showed immediate release (about 20 minutes) of GF. Overall, the films fabricated from polymer-based suspensions at higher viscosity dried at different conditions exhibited similar mechanical properties, improved drug content uniformity, and achieved fast drug dissolution.

Drug size reduction is commonly employed for improving the dissolution and bioavailability of poorly water-soluble drugs since a decrease in the particle size increases the drug dissolution rate. Wet stirred media milling (WSMM) has proven to be a robust top-down process for producing drug nanoparticles in the form of stable suspensions. The nanosuspensions are usually dried for incorporation of the drug nanoparticles into a solid dosage form. Incorporating them in a thin film form may provide a promising route for the delivery of nano-sized drug particles, provided that drying takes place in a reasonably short amount of time while drug particles are not irreversibly agglomerated, causing loss of their high surface area. Therefore, in this disclosure, fast drying via using forced convection at gentler temperatures to form novel stripfilm based pharmaceutical products containing uniformly distributed drug particles was considered with an objective of enhancing dissolution and hence bioavailability of poorly water soluble drugs, typically those belonging to BCS (Biopharmaceutical Classification System) Class II.

Pharmaceutical thin films have attracted much attention recently because of the improvement of patient compliance and the potential for scaling up, continuous processing and cost-effective manufacturing. Thin films also offer the ability to deliver drugs via buccal route, thereby avoiding first pass metabolism and enhancing the drug dissolution and bioavailability. Important quality attributes for drug nanoparticle-laden pharmaceutical films include uniform drug distribution in the film without irreversible particle agglomeration and the physical stability of the drug. As noted, two commonly used procedures for the fabrication of pharmaceutical films are hot melt extrusion (HME) and solvent casting technique (SCT). In HME, drug is mixed with a polymer and then both are melted and extruded through an orifice or die, typically resulting in amorphous form. HME has been used to form crystalline drug in polymer matrix at temperatures below the drug melting point resulting in very stable systems and the added shear forces by the extruder can be an advantage over SCT.

However, applications of HME for amorphous forms may be limited by difficulty in preserving the drug amorphous form and its long-term stability. Most studies pertaining to SCT involve dissolving a poorly water-soluble drug in an organic solvent and mixing the resultant solution with polymer precursors, followed up by casting and drying. While a number of papers have explored the incorporation of crystalline drug nano/micro particles into films via SCT, they did not consider the effects of drying regimes on the drug content uniformity and drug distribution in a film and the film properties. Most of such studies utilized conventional methods for drying polymer solutions loaded with drug particles that took from five to twelve hours to form a solid film Such long drying times may limit their suitability for industrial applications. In an earlier works on SCT, researchers proposed the use of conventional drying methods for fabrication of orally dissolving films loaded with drugs. However, it was observed in a later study that the processing regimes suggested caused drug particles to agglomerate and form a non-uniform drug distribution within the film. This drawback was attributed to long drying times. An increase in the film precursor viscosity and modifications of various processing parameters were suggested to overcome the drug agglomeration in the course of drying. However, in those studies the effectiveness of the proposed changes was not demonstrated since the distribution of drug particles in a film and the film properties were not investigated.

The present disclosure advantageously provides an SCT process for achieving high drug loadings of nano-sized particles of poorly water-soluble drugs into hydroxypropyl methylcellulose (HPMC) films, and provides that use of stable nano-suspensions produced by WSMM results in fast dissolution, although drying took about 12 h in certain embodiments. In the present disclosure, by examining the use of convective drying and higher viscosity film forming precursors, this methodology is significantly advanced so that it becomes practical and industrially relevant. Specific objectives were to evaluate the effects of drying regimes and the film precursor viscosity on the film structure, homogeneity and drug release profiles. Two aqueous HPMC-based drug-polymer film formulations with different viscosities were considered. Convective drying was carried out in an exemplary unit designed to provide uniform yet gentle heating, leading to reduced drying times from about 12 h to 1 h or less. Analysis of drying kinetics was done to examine the drying regimes for films with and without drug nanoparticles, produced at low as well as high intensity drying by changing the air-flow velocity and drying temperature. As per one of the main objectives, the drug distribution uniformity was examined at various scales of scrutiny using NIR-CI, as well as assay of film samples to determine the drug content variation.

NIR-CI analysis was also used to examine pairwise influence of three main factors, precursor viscosity, drying air velocity, and drying temperature so that most dominating factor could be identified. The state of the drug particles in dry films, as may be impacted by processing, was examined using powder X-ray diffraction analysis. Re-dispersion of films in water is carried out to find out the extent of recovery of the original nano-particles hence the level of irreversible nanoparticle agglomeration during processing. Mechanical properties such as the tensile strength and yield strength were measured for films produced under different conditions. In order to understand the impact of drying conditions on the dry film moisture content, thermo-gravimetric analysis was also performed. Finally, the drug dissolution from films was measured using an USP IV apparatus. As will be shown, the films fabricated from higher viscosity polymeric precursors and dried under different conditions exhibited improved drug content uniformity and achieved fast drug dissolution, demonstrating the robustness of the developed film forming procedures.

Materials and Methods:
Materials:

Griseofulvin (GF; Sigma-Aldrich, Saint Louis, Mo.) was utilized as a model BCS Class II drug. Sodium dodecyl sulfate (SDS) (Sigma-Aldrich, Saint Louis, Mo.) and low molecular weight hydroxypropyl methylcellulose (HPMC; Methocel E15LV) (Dow Chemical) were used as stabilizers; the latter was also used as a film former. Glycerin (Sigma-Aldrich, Saint Louis, Mo.) was used as a plasticizer. GF particle size was reduced using a wet stirred media mill as explained in the next section. The other materials were used without further processing.

Methods:
Preparation of Drug Nanosuspensions Via Wet Media Milling:

HPMC and SDS were selected based on their synergistic stabilizing action on the drug nanoparticle suspensions and their concentrations were set at 2.5% w/w (wrt water) and 0.5% w/w (wrt water), respectively. HPMC was dissolved in 200 g de-ionized water using a shear mixer running at a fixed speed of 300 rpm for 30 min., followed by addition of SDS under stirring for 15 min. The drug (GF 10% w/w, wrt. water) was then dispersed into the stabilizer solution with the shear mixer running for 30 min. A suspension sample was taken at the end of mixing to determine the initial particle size of the drug. The GF suspensions prepared via mixing were subsequently milled for 60 min in a Netzsch wet media mill (Microcer, Fine particle technology LLC, Exton, Pa., USA).

Particle Size Distribution:

The particle size distribution of GF in the nano-suspensions was measured by laser diffraction in Coulter LS13320 (Beckman Coulter, Miami, Fla., USA). A sample of the suspension was taken at the end of milling from the holding tank of the mill. The sample was dispersed in 15 ml HPMC-SDS stabilizer solution by stirring with a pipette. The sample was added drop-wise until the polarization intensity differential scattering (PIDS) reached 40%.

The same method was used to measure the particles size of GF nanoparticles re-dispersed in water from films. Circular films with an area of 0.712 $cm^2$ and an average thickness of 80 μm were put in approximately 15 ml of de-ionized water (concentration above the solubility for all samples) for film disintegration. The sample particle size was measured after 10 min of magnetic stirring.

Preparation of Films Containing Nanoparticles:

The preparation of films containing nanoparticles with low viscosity film precursors and without use of convective drying has been presented previously. Briefly stated, the polymer solution, prepared by adding weighed amount of HPMC and glycerin to water (on w/w basis) at 90° C., was allowed to cool down to room temperature while being stirred continuously, and left overnight for deaeration. This polymer solution (50 g) was added to the drug nano-suspension (25 g) in 2:1 ratio and mixed for 4 h using a motor driven dual-propeller mixer (McMaster, USA).

The compositions of the film-precursor slurries, chosen based on preliminary viscosity measurements, are given in Table 1, above. It is expected that viscosity would play a major role for uniformity of film thickness as well as drug distribution. Two compositions, A and B, both containing glycerin (5% w/w) as a plasticizer, were formed by mixing about 12% HPMC and 15% HPMC solutions with GF nanosuspension, respectively. Their viscosity was measured using an R/S plus Rheometer (Brookfield Engineering, USA) at a shear rate of 2.2 $s^{-1}$, having a water jacket assembly kept constant at 25±0.5° C. The shear viscosities, measured in duplicate, for the two suspensions were 2400 cP and 6200 cP respectively (Table 1). Approximately 6 g of the final viscous suspensions were manually cast at room temperature onto a stainless steel substrate using a casting knife (Elcometer, USA) at a draw ratio much below the critical value such that variations of the film thickness were less than 6% with casting thickness set at 1000 μm. The cast film sample, about 8 cm×9 cm, was placed into the convective drying unit (FIG. 4), and dried under different drying conditions as shown in the experimental matrix (Table 2, above). The dried films were placed in a desiccator to avoid any further moisture absorption.

Convective Drying Unit:

A convective drying unit, FIG. 4, is equipped with a heating element mounted on the chamber floor, an air blower with a heating coil mounted at the chamber inlet to control the air velocity and temperature, a rotating vane anemometer (outlet) and an automated balance connected to the sample stage controlled by a data acquisition system to record the sample weight every 15 s in the course of drying. The air blower settings help control the temperature and velocity (laminar conditions) of the air that is fed into the chamber at relative humidity of 40-60%. The flow rate and temperature of air exiting the chamber were recorded. A film sample cast on a 0.4-mm stainless steel plate was introduced into the chamber after the drying system was at a desired set temperature. Use of the stainless steel plate helps keep the temperature variation across the sample during the course of drying to within 1.2° C.; sufficient to suppress the formation of defects and the buildup of stress as the polymer-based film forms. The sample was held in the chamber until its weight stopped changing.

Film Characterization:

Film Thickness:

The thickness of the films was measured using a digital micrometer with an accuracy of 0.001 mm. Thickness was measured at 4 different locations across the film and used for calculating the average and relative standard deviation. The average thickness of the films (A1-A4 and B1-B4) was found to be around 80 microns with relative standard deviation of about (6%).

SEM:

A field emission scanning electron microscope (FESEM) LEO1530VP GEMINI (Carl Zeiss, Inc., Peabody, Mass., USA) was used to observe the morphology of GF particles produced from WSMM and the distribution of particles in the films. For the analysis of particles from WSMM, a drop of the nano-suspension was placed on the silicon chip placed on top of carbon tape and left overnight to dry under vacuum. Similarly for analysis of GF particle distribution in the polymer film a small piece of the film was placed on the carbon tape for the analysis of the films. Samples were carbon coated using a sputter coater before imaging in both the cases.

Powder X-Ray Diffraction (XRD):

The powder X-ray diffraction patterns of GF powder and GF loaded HPMC film samples (A1-A4 and B1-B4) were measured on Bruker D8 AXS (Bruker GmBH, Karlsruhe, Germany) equipped with a vertical goniometer using Bragg-Brentano geometry (θ/2θ). In this configuration the detector employs GÖBEL mirrors and a LYNXEYE linear detector. A monochromated Cu Kα radiation ($\lambda$=1.5406 Å) was used at an operating voltage and amperage set of 40.0 kV and 40.0 mA respectively (1.6 kW). For powders, a sample of approximately 100 mg was placed on a low volume low background sample holder (quartz 511 plane) and pressed gently with a glass slide to obtain co-planarity between the sample and holder surface. The sample was scanned from 5° to 35° 2θ with a step size of 0.01° 2θ and scanning rate of 1.2° 2θ per min. For films, a section of approximately 1 cm$^2$ was cut from the sample and was placed on the same low background holder, insuring the samples all lay flat and the same conditions were used to collect the pattern. The powder patterns were compared to a simulated powder pattern generated from the single crystal structure in the Cambridge Structural Database System (Refcode: GRISFL) (Cambridge Structural Data System (CSDS)).

NIR Chemical Imaging:

Near infrared Hyperspectral images in transflectance mode were acquired using the Malvern SyNIRgi NIR-CI System (Malvern, UK). The films were analyzed with a 131 μm/pixel objective having a field of view of 34×42 mm and permitted chemical imaging of the entire film sample. All raw reflectance data was converted to absorbance, log (1/R), and pixel correction was applied in order to remove areas of non-uniform illumination and the effect of unresponsive pixels. The spectra were normalized using Standard Normal Variate (SNV) and a Savitzky-Golay second derivative (filter order 3, filter width 7). Pure component imaging data was collected from powder samples of the GF and excipients where spectral pretreatment was performed in the same manner.

Pure components (GF, HMPC, SDS, Glycerin) references were used to build a partial least squares-discriminant analysis (PLS-DA) classification model for GF. Based on the evaluation of the full spectral range (1300-2300 nm), the best calibration model was obtained with the 2000-2300 nm range, where the areas of pure GF would have a score value of 1.0 or 100%, and without GF a score of value of 0. The score values were used to estimate the drug abundance, denoting the presence of GF at a specific localized area. These score images were evaluated using the ISys Version 5.0.0.14 software, capable of determining particle/domain size and distribution of individual chemical species within chemical images.

For better visualization of the drug rich areas in score images, thresholding was applied to obtain binary images, where pixels with abundance values greater than the mean plus 2 standard deviations are marked with the black color. Comparison of binary images developed with a previously described method based on the second derivative intensity of the GF band at 2080 nm (Jerez-Rozo et. al., 2011) and used for films, validated the drug rich areas indicated by the PLS-DA classification model.

Determination of Drug Content in Films:

An Agilent 1100 series HPLC system consisting of a pump and a UV detector were employed for determining the drug content in films. A 1-cm wide region of a complete film sample close to the edges was trimmed off and ten circular shape samples, each with an area of 0.712 cm$^2$, were punched out from the remaining portion (about 40 cm$^2$). The samples were dissolved in 250 ml of 0.025 M SDS solution and the concentration was calculated using UV detection at 291 nm. The temperature was maintained at 25° C. The mobile phase was a mixture of water and acetonitrile (50:50, v/v) with a flow rate of 1.0 ml/min. The samples were put into HPLC vials and 20 μL automatically injected into the HPLC system. The concentration was determined from a calibration curve. The average GF weight and relative standard deviation over ten samples was calculated.

Thermo-Gravimetric Analysis:

Thermo-gravimetric analysis (TGA) of films with and without GF nanoparticles was performed with a TGA/DSC1/SF Stare system (Mettler Toledo, Inc., Columbus, Ohio, USA). A small sample of a film (about 2.0 mg) was placed in a ceramic crucible, heated from 25° C. to 150° C. in nitrogen atmosphere at a constant heating rate of 5° C./min, kept at 150° C. for 15 min and then heated up to 200° C. at a rate of 5° C./min. Finally, the sample was brought back to room temperature (25° C.) at a cooling rate of 10° C./min. Measurements were conducted on two different samples for each film.

Mechanical Properties:

Mechanical tests were conducted using a TA-XT Plus Texture Analyzer (Stable Microsystems, UK) to measure mechanical properties, tensile strength and yield strength. Four rectangular strips having dimensions of 50 mm×15 mm were cut from a single film and tested. The strip was held in place between the two grips and stretched at a test speed of 1 mm/s until the breaking point (e.g., tensile failure). The engineering tensile and yield strengths were computed (measured force divided by the initial cross-sectional area) from the stress versus strain data. The average and the standard deviation computed over the four samples were tabulated.

Dissolution Testing and Drug Release Kinetics:

Dissolution experiments were performed using a flow-through cell dissolution apparatus (USP IV, Sotax, Switzerland) with cells of an internal diameter of 22.6 mm. Circular film samples (having an area of 0.712 $cm^2$) were horizontally positioned in the cells with 6.5 g of glass beads (1 mm in diameter) filling up the conical part at the bottom of each cell. Pall HT Tuffryn membrane disc filters (0.2 μm) were used. The issue of using large pore size filters in comparison with the size of nanoparticles has been also addressed before in the literature. The temperature was maintained at 37±0.5° C. and a flow rate of 16 ml/min was used. During testing, a 100 ml dissolution medium (SDS solution (5.4 mg/ml)) was circulated by pumping it through each cell. Six samples were used and the average drug release was plotted as a function of time. As a comparison, dissolution test of physical mixture containing HPMC, GF and SDS (in powder form) and as received GF powder (about 20 μm) was also done. Physical mixture of GF, HPMC and SDS were prepared. The concentration of all the mixture components was kept similar to that in the film (Table 1). For as received GF, powder of weight equivalent to that of the drug in the film was used.

The release kinetics of GF from HPMC films were determined by finding the best fit for the release profiles. Zero-order release Equation, first-order release equation, Higuchi equation and Korsmeyer-Peppas (KP) equation were used to analyze the release kinetics of GF. The linear portions of the release curves (corresponding to 60% of drug release based on drug assay analysis) were fitted using the models mentioned above. Similarity and difference factors were also computed between dissolution profiles of GF from films to determine the effect of drying conditions and starting suspension viscosities on drug release.

Figure 43:
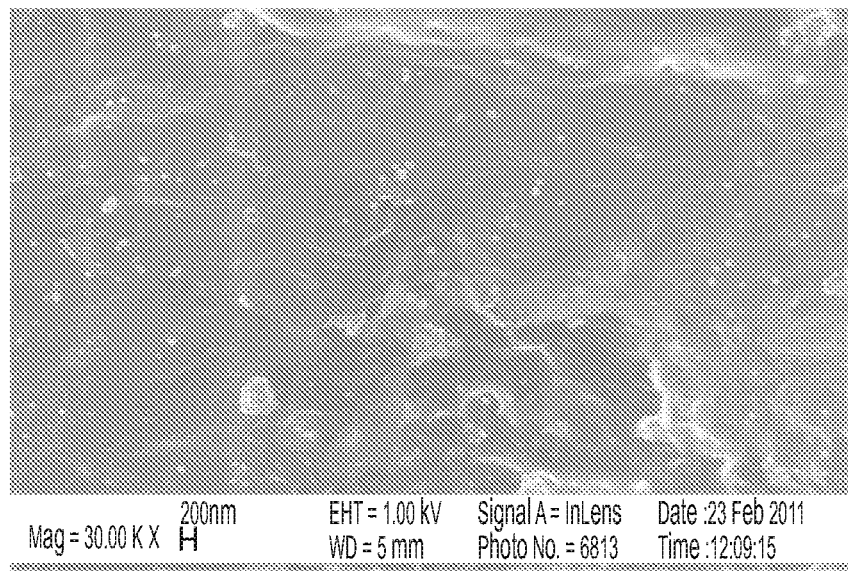
FIG. 43 is a cross-sectional SEM image of a dried HPMC film loaded with GF nanoparticles.
Figure 44A:
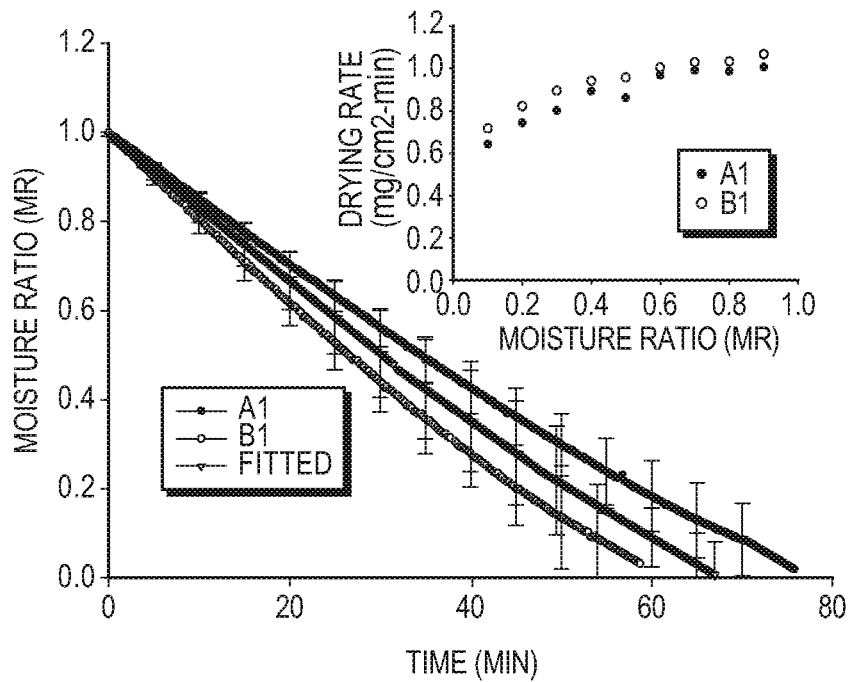
FIGS. 44A-D shows drying curves of samples (MR vs. drying time t (min)); sample compositions are listed in Table 1, drying regimes are listed in Table 2; points on the curves are the mean of three samples with error bars of one standard deviation; insets show the drying rate vs. MR.
Figure 44B:
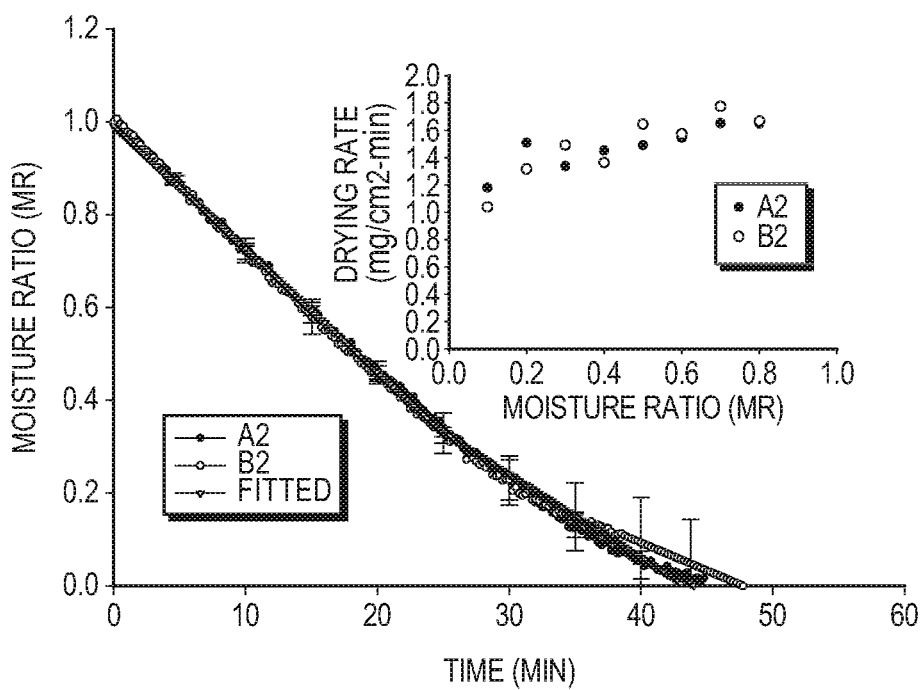
Figure 44C:
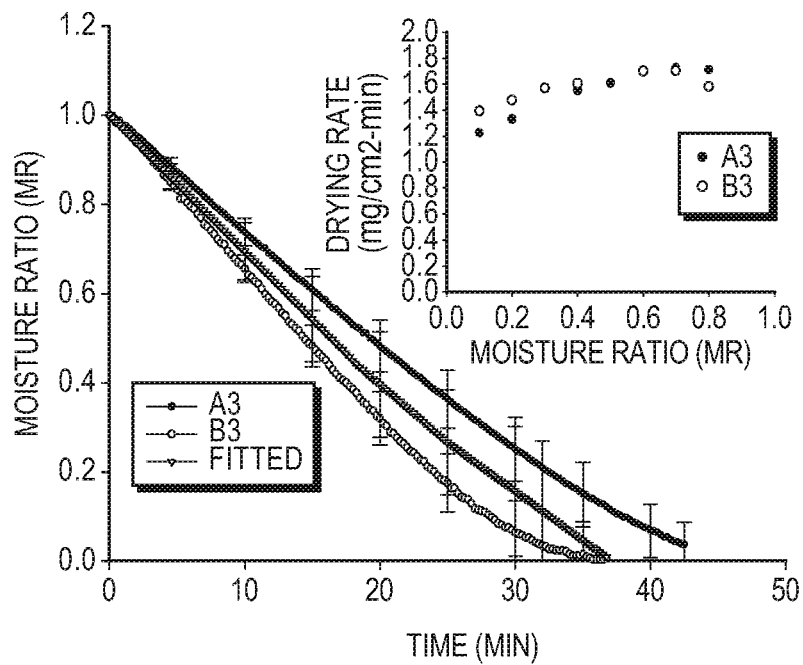
Figure 44D:
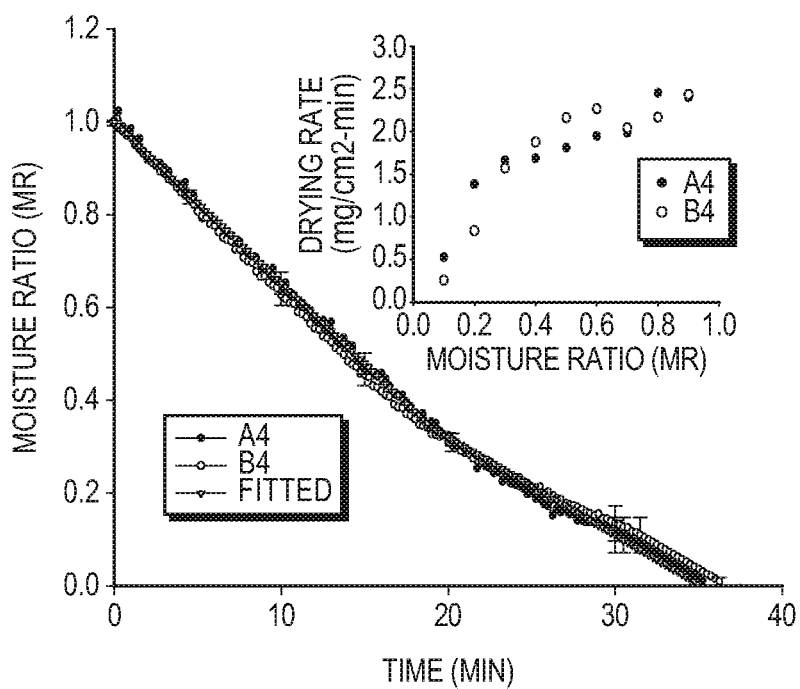

Results and Discussion:
Production and Characterization of Drug Nano-Suspensions:

Physically stable GF nano-suspensions were produced using HPMC and SDS as stabilizers during wet stirred media milling. After 60 min of milling, the median particle size of GF particles was reduced from 11.8 μm to 163 nm, and the particle size was stable after 7 days of storage. FIGS. 1 and 43 show a scanning electron micrographs for the nanoparticles produced by the media milling. After milling, the nanoparticles were partially covered by the adsorbed polymer (HPMC), which was part of the milling formulation. Milled particles are rounded as seen in FIG. 1.

Drying Kinetics:

Drying conditions can impact the final product quality significantly. If the drying is not effective then the final residual moisture in the film can be large, impacting the long term stability of the film. Moreover, if the drying temperatures or conditions are too harsh, Ostwald ripening of drug particles could also occur. In addition a major challenge with convective drying is skin formation or ripple effect, which could lead to inhomogeneous film with aggregated drug particles. Bearing these in mind gentle drying temperatures of 40±0.1° C. and 60±0.1° C. and air flow velocities of 0.5±0.02 m/s and 1.5±0.02 m/s (Table 2) were employed. These temperatures were also well below the phase transition temperature of HPMC solutions. Subsequently, the employed drying regimes (isothermal laminar air flow with temperature uniformity within 1.2° C.) aided in fabrication of uniform GF particle loaded thin polymer films.

The instantaneous water content of a sample in the course of drying was computed as the difference between the recorded sample weight and its final weight at the end of drying (often referred to as dry weight). The fraction of water remaining in the sample at a given time, hereafter called moisture ratio, MR, was computed as the ratio between the recorded water content and the initial water content. The film drying curves, MR vs. drying time t (min), are plotted in FIGS. 44A-D, where each point represents the mean of three samples. As can be seen in FIGS. 44A-D, the impact of starting solution viscosity was found to be statistically insignificant. The drying curves for HPMC solutions are not presented because the difference between the drying curves of HPMC solutions with and without GF particles lies within the error of measurements shown in FIGS. 44A-D. To filter noisy MR data (having the level of noise about 0.05), the measurements were fitted over a time period for which MR varied by 0.1 using a linear equation, MR=b·t (min)+c, thus obtaining b as the drying rate. The use of a quadratic equation did not improve the fit and the drying rate values from linear and quadratic components were found to be statistically the same. The drying rates of HPMC-based GF suspensions are presented in insets in FIGS. 44A-D as a function of MR. These plots display a typical two-stage drying regime with an approximately constant initial drying rate period down to about MR=0.5 followed by a falling drying rate period. The drying rates of HMPC solutions with and without GF particles are summarized in Table 29. The relative standard deviations (RSD) between these values and the mean of drying rates plotted over the range 1>MR>0.5 in insets in FIGS. 44A-D rise with increasing the drying intensity, from 0.7% for A1 and B1 to 6.1% for A4 and B4.

The constant drying rate period occurs as the water transport to the sample surface and evaporation from the surface is faster than the removal of the water vapor by air flow. To elucidate the effects of the HPMC content, GF particles and additives on water transport, the rate of water removal from a shallow dish of dimensions 8×9 cm filled with water was measured under tested drying regimes. The rate of water removal was computed from the dish weight until the water broke into droplets (Table 29). As can be seen in Table 29, rates of water removal from the dish and the solutions and suspensions are nearly the same (differences are statistically insignificant based on the 95% confidence interval), thus the additives, including the surfactants, do not impact the first constant stage of drying, indicating the existence of a continuous water network through film precursor samples down to about MR=0.5. As the water content of HMPC solutions with and without GF particles reduces below about MR=0.4 (FIGS. 44A-D), the drying rate gradually decreases due to a hindrance to water transport caused by the polymer network that forms as drying progresses.

Trying linear and quadratic regression equations demonstrates that a linear regression, drying rate ($mg/cm^2$·min)=b ($mg/cm^2$·min) MR+c ($mg/cm^2$·min), fits the drying curves well over the period from MR=0.4 down to about 0.1 (Table 30) as the quadratic component was found to be statistically insignificant. The drying rate of samples decreases faster with decreasing MR (Table 30, FIGS. 44A-D) as the drying intensity increases from 40° C./0.5 m/s for A1 and B1 to 60° C./1.5 m/s for A4 and B4. The fact that drying rates of samples having different initial HPMC contents appear to be very close suggests that the structure of a polymer network (density, cluster size, tortuosity, etc.) forming in a sample in the course of drying for MR>0.1 depends mainly on the rate of water removal governed by the air flow velocity and temperature.

TABLE 29

Comparisons of drying rates during the constant rate period for HPMC films with and without GF nanoparticles:

| Sample | Air temperature (° C.) | Air velocity (m/s) | Drying rate (mg/cm$^2$min) | Coeff. of determination, $R^2$ |
|---|---|---|---|---|
| Water | 40 ± 0.1 | 0.5 ± 0.02 | 1.03 ± 0.01 | 0.99 |
| A1, B1 | 40 ± 0.1 | 0.5 ± 0.02 | 1.04 ± 0.03 | 0.99 |
| Water | 40 ± 0.1 | 1.5 ± 0.02 | 1.70 ± 0.01 | 0.99 |
| A2, B2 | 40 ± 0.1 | 1.5 ± 0.02 | 1.50 ± 0.11 | 0.99 |
| Water | 60 ± 0.1 | 0.5 ± 0.02 | 1.70 ± 0.01 | 0.99 |
| A3, B3 | 60 ± 0.1 | 0.5 ± 0.02 | 1.60 ± 0.07 | 0.99 |
| Water | 60 ± 0.1 | 1.5 ± 0.02 | 2.50 ± 0.01 | 0.99 |
| A4, B4 | 60 ± 0.1 | 1.5 ± 0.02 | 2.45 ± 0.03 | 0.99 |

TABLE 30

Comparisons of drying rates during the falling rate period for HPMC films with and without GF nanoparticles. Linear fit (drying rate (mg/cm$^2$ · min) = b(mg/cm$^2$ · min) MR + c(mg/cm$^2$ · min)) parameters for the period from MR 0.40 ± 0.05 down to about 0.1 are shown:

| Sample | b (mg/cm$^2$ · min) | c (mg/cm$^2$ · min) | Coefficient of determination $R^2$ |
|---|---|---|---|
| A1, B1 | 0.79 ± 0.13 | 0.55 ± 0.20 | 0.97 ± 0.01 |
| A2, B2 | 1.25 ± 0.36 | 0.89 ± 0.05 | 0.78 ± 0.02 |
| A3, B3 | 1.35 ± 0.15 | 1.05 ± 0.04 | 0.95 ± 0.01 |
| A4, B4 | 2.75 ± 0.67 | 0.95 ± 0.43 | 0.95 ± 0.04 |

Characterization of Particles in Film:
SEM:

SEM images for the surface of films are shown in FIGS. 1 and 43. Here, GF nanoparticles within the film matrix may be observed without the presence of any significant agglomeration. Since an SEM image can only provide a qualitative picture of the particle distribution, more detailed analysis via NIR-CI is considered next.

NIR Chemical Imaging:

Distribution of the GF particles within the 34×42 mm film was evaluated with the abundance values determined with the PLS-DA method. The use of binary images facilitated the identification of drug rich areas. Thresholding was employed to obtain binary images for all possible combinations of airflow, viscosity and temperature (images presented in supplemental information), and helped identify viscosity as the most significant processing parameter. For the sake of brevity, only pairwise comparison for viscosity is shown in FIG. 5. The dark areas in FIG. 5 correspond to the GF abundances exceeding two standard deviations from the mean, hence all white areas are those where GF is within two standard deviations from the mean. Thus FIG. 5 provides qualitative visual information regarding drug distribution and variation within the film sample; images with mostly white areas qualitatively indicate absence of drug rich areas and better overall drug distribution, which is observed for all higher viscosity samples.

Table 31, representing significant amount of image statistics at a very small scale of scrutiny, shows the results of the statistical analysis of binary images from FIG. 5. The first two rows of the table (Number of Drug Rich Areas and their Mean Area) for each pair of higher (B sample) and lower (A sample) viscosity cases with other parameters held constant, show that the higher viscosity case has not only fewer drug rich areas, but also their average sizes are smaller; the lowest average size being the case for a viscosity of 6200 cP, temperature of 60° C., and an air flow of 1.5 m/s.

NIR-CI imaging along with PLS-DA allowed the comparison of the abundance results obtained throughout the surface of the films. Each pixel in NIR-CI imaging covers a diameter of at least 131 μm within the 34×42 mm film analyzed, thus the entire sample consists of about 80,000 pixels. The mean value of those pixels is comparable to the concentration value that could be obtained with a single standard non-imaging NIR spectrum of the film. The mean abundance value determined by the PLS-DA model was comparable with the nominal value of the films, estimated from the individual film compositions. The drug distribution was better in higher viscosity "B" samples with a standard deviation of 1.3-1.5%, versus 1.8-2.1% values in the lower viscosity "A" samples. The samples obtained from higher viscosity precursors also had lower one and three std values, and estimated relative standard deviation for all "A" samples based on over 80,000 pixels is about 7.4%, while that from "B" samples is about 6.2%, suggesting that film formulations may be optimized to achieve films with very good drug distribution within each sample, considering this RSD is at a very fine scale of spatial distribution with each sample at a diameter of 131 μm.

In summary, NIR-CI provided significant information on the distribution of drug particles. In terms of drug rich areas, a smaller number of smaller drug rich particles is observed at 6200 cP and 60° C., whereas significant number of larger clusters or agglomerates are observed at 2400 cP and 40° C. The standard deviations of the abundance values also indicate that these films have uniform drug distribution, with less variation in the films manufactured with higher viscosity precursors. Overall, the results demonstrate that the viscosity has the most dominating effect on the drug distribution.

TABLE 31

Domain size statistic results of drug based on binary images generated from scores images; highlighting viscosity as the major variable from the design of experiments:

| Temperature-Velocity | 40° C. - 0.6 m/s | | 40° C. - 1.5 m/s | | 60° C. - 0.6 m/s | | 60° C. - 1.5 m/s | |
|---|---|---|---|---|---|---|---|---|
| Viscosity (cPs) | 2400 | 6200 | 2400 | 6200 | 2400 | 6200 | 2400 | 6200 |
| Films | A1 | B1 | A2 | B2 | A3 | B3 | A4 | B4 |
| Number of Drug Rich Areas | 186 | 71 | 147 | 66 | 198 | 48 | 317 | 20 |

TABLE 31-continued

Domain size statistic results of drug based on binary images generated from scores images; highlighting viscosity as the major variable from the design of experiments:

| | | | | | | | | |
|---|---|---|---|---|---|---|---|---|
| Mean Area (mm$^2$) | 0.317 | 0.191 | 0.228 | 0.138 | 0.358 | 0.159 | 0.314 | 0.083 |
| Area STD (mm$^2$) | 0.905 | 0.305 | 0.296 | 0.172 | 1.05 | 0.165 | 0.576 | 0.108 |
| Largest domain size (mm$^2$) | 9.49 | 1.7 | 2.04 | 0.841 | 11.9 | 0.755 | 6.57 | 0.515 |
| Lowest domain size (mm$^2$) | 0.0172 | 0.0172 | 0.0172 | 0.0172 | 0.0172 | 0.0172 | 0.0172 | 0.0172 |

Figure 45A:
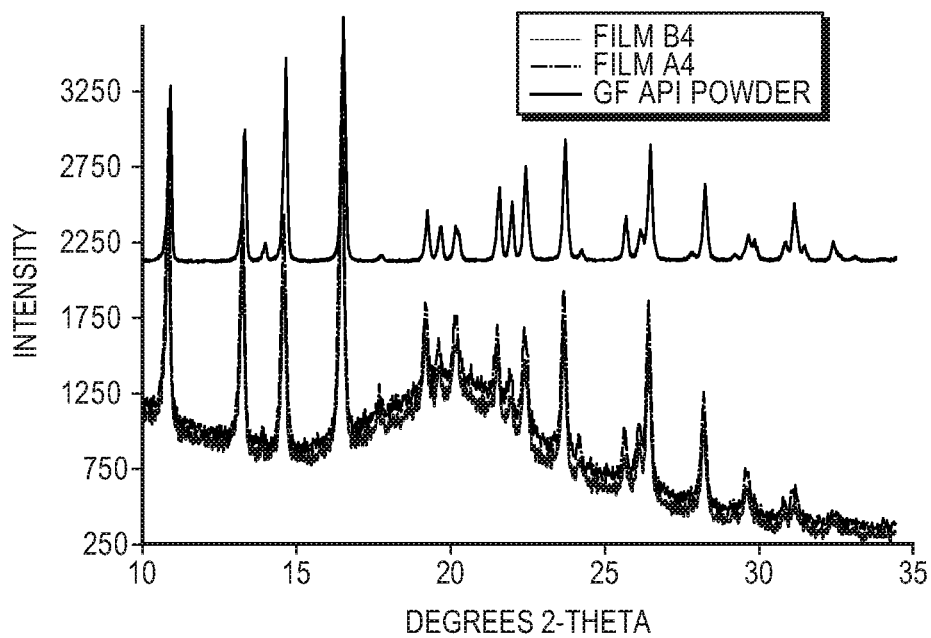
FIG. 45A-B show: 45A—PXRD patterns for GF powder and two cast films of varying initial composition showing the same crystal structure is maintained; 45B—PXRD patterns for eight films showing the same crystal structure is retained irrespective of the film drying conditions.

Drug Solid State Analysis Using Powder X-Ray Diffraction (XRD):

The powder XRD analysis of the cast/dried films was performed to determine if the drug was 1) maintained in a crystalline form, 2) if so, what form and 3) if there was significant variation in the solid drug characteristics as a function of the film formation conditions. FIG. 45A shows the PXRD for the bulk griseofulvin drug and two cast films containing the drug (samples A4, B4). It is clear from the patterns that the initial drug crystal form is retained in the films (which is the form verified as griseofulvin's from CSDS crystal structure). Comparing the cast films with and without drug also indicates that the majority of the drug is in the crystalline state, e.g., the diffuse scattering observed in the patterns closely matches the "placebo" films pattern in shape and area. Also comparison of the relative peak intensities in the bulk drug's pattern to those from the films is consistent with a random presentation of crystal faces to the beam which is a characteristic often associated with uniform particle shapes displayed in FIG. 1.

Figure 45B:
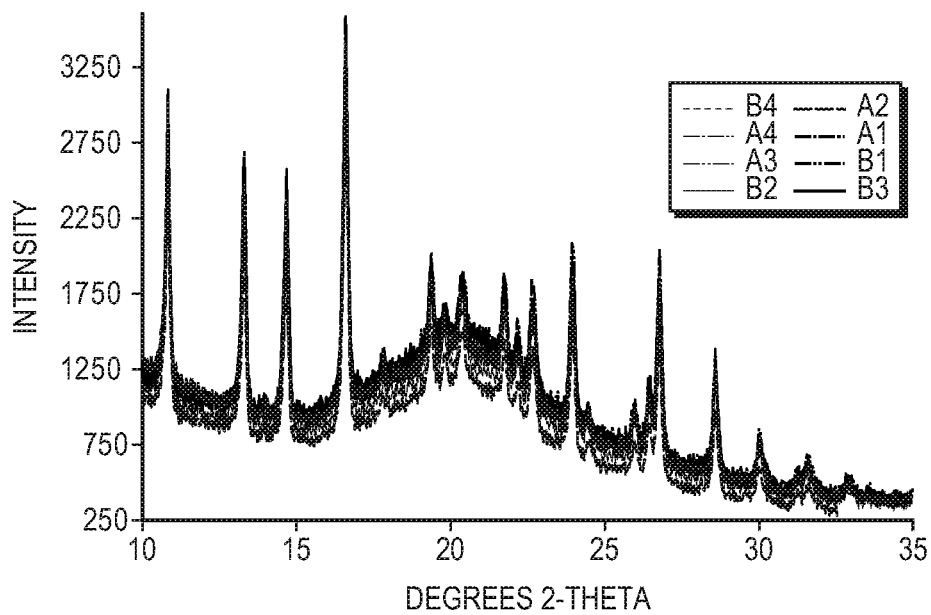

FIG. 45B shows the powder patterns for all of the films (A1-A4 and B1-B4) prepared for the study. The patterns are very similar and show that the form remains unchanged across all the samples. In addition, the inter-sample variation is very small, expected from minor differences in film dimensions and/or distribution of particles. Extensive characterization of wet-milled and dried GF particles via DSC, XRD, and Raman spectroscopy showed no impact of wet milling on GF crystallinity; therefore, we can infer from FIG. 45A and FIG. 45B that film formation via convective drying had no impact on the GF crystallinity.

Re-Dispersion of Particles from Films:

A concern regarding the formation of dry dosage forms from drug nano-suspensions is that after drying, nanoparticles incorporated in solid dosage forms may not be recovered from the solid dosage form during dissolution either in vitro (standard dissolution test) or in vivo (gastrointestinal fluids in the body). The poor drug nanoparticle recovery can lead to reduced dissolution rate and bioavailability of the drug. In re-dispersion studies, it is customary to compare the particle size distribution of the nano-suspension with that resulted from re-dispersion of dried nano-suspensions in water to assess the recovery and re-dispersion behavior of drug nanoparticles.

Figure 46:
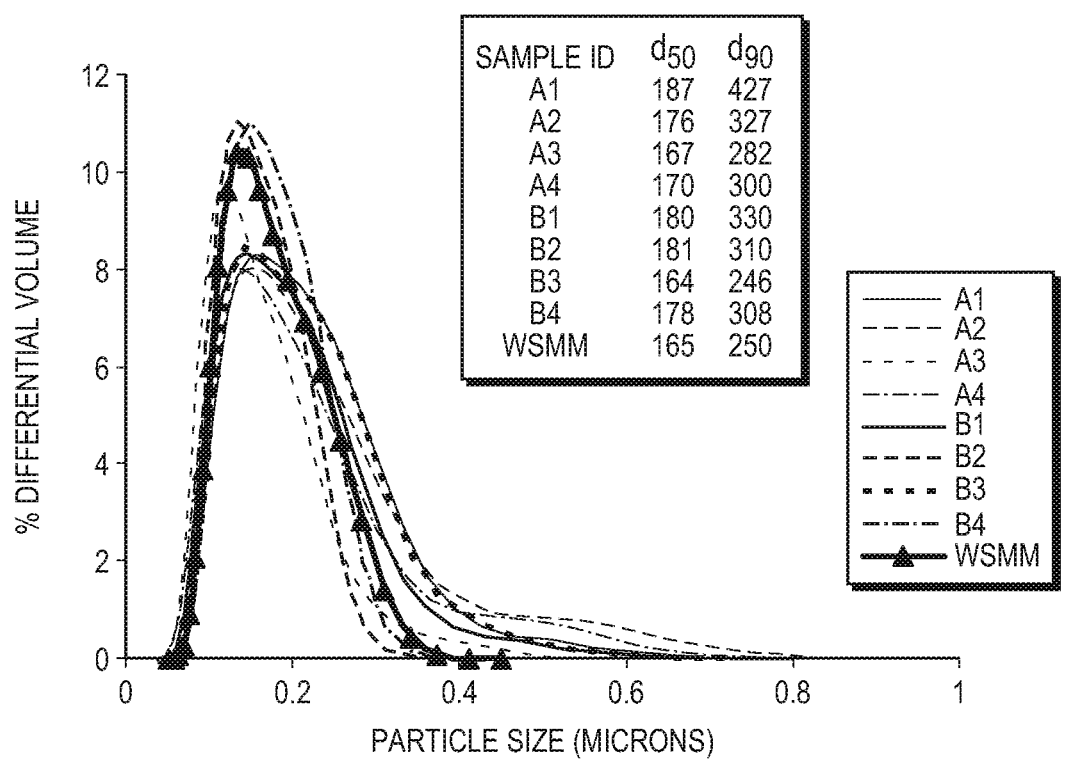
FIG. 46 shows a comparison of particle size distribution curves for GF nanoparticles re-dispersed from dried HPMC films (all eight samples) and original GF nanosuspension produced via WSMM.

FIG. 46 shows the nanoparticles (GF) size distribution for the starting nano-suspensions (produced from WSMM) as well as nanoparticles (GF) size distribution after film re-dispersion in deionized water. In the differential distribution curves, it is clear that the principal mode in all cases occurs below 200 nm, and the $d_{50}$ values are also comparable. As can be seen from the table inset in FIG. 46, the d50 values for both the WSMM suspensions and all the eight samples are very similar, ranging from 165 to 187 nm. The $d_{90}$ values are slightly higher for some cases upon re-dispersion; however, overall there is low extent of agglomeration at the sub-micron scale, and the film-precursor viscosity and/or drying conditions had minor impact. These results also suggest that irreversible nanoparticle agglomeration did not occur during the drying.

Content Uniformity:

Table 32 shows the average content of drug per area for all the films. The relative standard deviations (RSD) for all the GF loaded HPMC films were low, with the highest measured value being 6.3%. Overall the RSDs for films formed from high viscosity suspensions (composition B) were lower than those for films formed from low viscosity suspensions (composition A). Further, the RSD values for GF films formed from composition B and dried at lower temperature (B1 and B2) were well under 3%. These observations are also supported by the NIR CI results. For the current study, due to manual casting procedure, there was no specific attempt made to control film thickness. However, based on the analysis of the films obtained, there were some variations in thickness between samples (thickness RSD was as high as 6%) that could lead to the variations in content uniformity. If the correction for the film thickness variation was taken in to account, the computed RSD values (for weight percent of drug) reduced to less than 2% for all the samples. In summary, the proposed approach of film formation and drying along with higher film-precursor viscosity inherently leads to low RSD values.

TABLE 32

Content uniformity result for HPMC films containing GF nanoparticles. Each sample is 0.712 cm$^2$, corresponding to about 1.4 mg dose:

| Sample ID | RSD (%) | Average amount of drug (mg) | Average amount of drug per area (mg/cm2) |
|---|---|---|---|
| B1 | 2.67 | 1.38 | 1.95 |
| A1 | 5.77 | 1.64 | 2.31 |
| B2 | 2.03 | 1.57 | 2.20 |
| A2 | 4.97 | 1.44 | 2.03 |
| B3 | 4.93 | 1.33 | 1.87 |
| A3 | 6.30 | 1.32 | 1.85 |
| B4 | 5.63 | 1.32 | 1.85 |
| A4 | 5.11 | 1.34 | 1.89 |

Mechanical Properties:

The mechanical properties of pharmaceutical thin films play an important role in product development and it is important to have flexible films with good mechanical strength. The mechanical strength of pure HPMC films (without any GF nanoparticles) and HPMC films containing GF nanoparticles were measured. The tensile (19±3.1 MPa) and yield strength (25±3.3 MPa) values in both cases were found to be statistically the same. Researchers examined the impact of poorly water soluble drug nanoparticles on the mechanical strength of HPMC films. It was observed that GF nanoparticles did not have strong interactions with HPMC matrix and therefore no significant impact on the mechanical strength of HPMC films was found. FTIR of the GF-HPMC films indicated that GF did not show any change in band position indicating weak interaction with the HPMC matrix. The results of the present disclosure are in good agreement with their results.

Further, although the mechanical properties of polymer films are known to vary with amount of additives and also with drying conditions such as temperature and humidity, here, there were no significant differences observed between strength of samples dried under different conditions. This is further examined via thermo-gravimetric analysis.

Thermo-Gravimetric Analysis:

TGA measurements were done for films with and without GF particles and subjected to low- and high-intensity drying regimes (corresponding to samples A1, B1 and A4, B4 in Table 29, respectively). The presence of GF particles, the solution viscosity and the drying regime did not significantly affect the TGA results. Weight losses appeared to be about 5 wt % for heating a sample from room temperature up to 100° C., representing mostly the loss of water. The exposure of samples to 150° C. for 15 min resulted in a weight loss of about 10-15 wt %. The significant weight loss at 150° C. can be attributed to the presence of glycerin in the film Overall the drying process is effective in keeping the free moisture content at low value of about 5 wt %, expected to aid in long-term stability of films.

Figure 47:
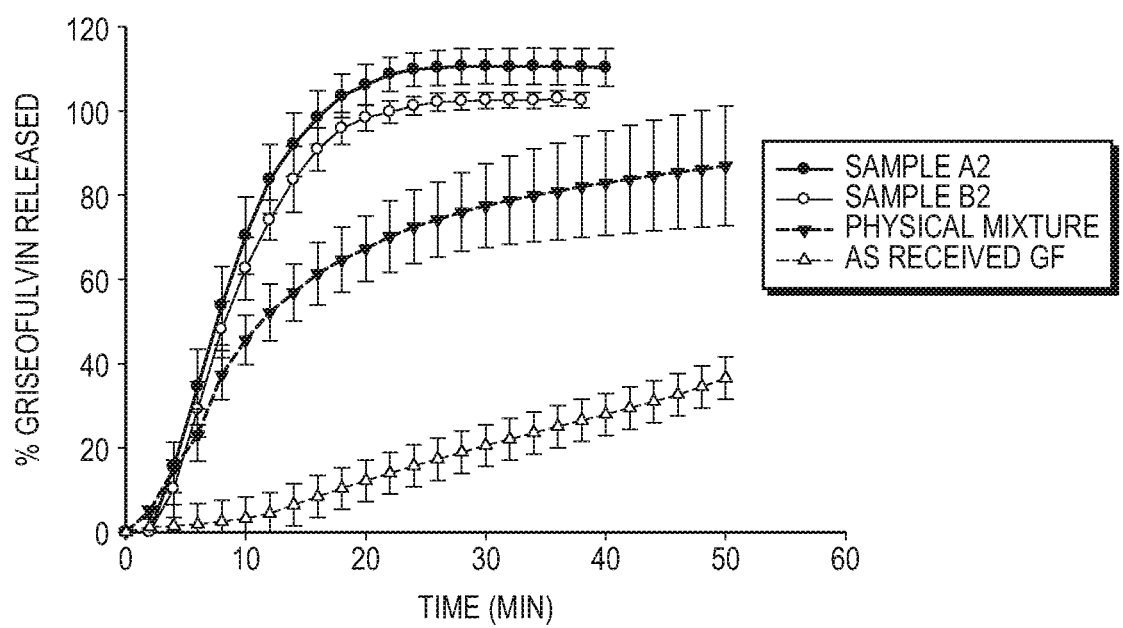
FIG. 47 shows a comparison of GF release profiles from HPMC films of varying initial composition, physical mixture (HPMC, SDS, GF microparticles) and as received GF powder.

Dissolution and Drug Release Kinetics:

It was observed that for all the films, most of the drug was released in about 20 min, indicating that these thin films could potentially be used as oral immediate release dosage forms for poorly water soluble drugs. FIG. 47 compares the dissolution profile of GF from representative film samples (compositions A2 and B2), physical mixture and pure GF powder.

The physical mixture took about 50 minutes to release about 85% of GF, whereas only 40% of GF was released in 50 minutes from as received powder. As can be seen, the release of GF from films is very fast when compared with physical mixture or as received powder. This appears in part due to preservation of the large surface area of GF nano-particles. Similarity and difference factors were computed between drug release profiles from all eight film samples (A1-A4 and B1-B4) to analyze the impact of compositions, drying temperature and air velocity on dissolution behavior of GF from HPMC matrix. It was found that the drug release profiles for all the compositions (A1-A4 and B1-B4) were found to be similar, thus corroborating the re-dispersion results presented here. Therefore, it can be concluded that the effects of drying conditions and initial composition on the GF release profiles were negligible. The dissolution kinetics for the films were analyzed and Korsmeyer-Peppas (KP) model was found to be a good fit for the release profiles, with $R^2$ values greater than 0.98. The n values for GF films from this study were found to be greater than 1, suggesting super case II transport type of a release behavior. Hence the release kinetics from GF films appears to be controlled by erosion and swelling phenomena.

Summary and Conclusions:

Through use of relatively mild drying temperatures (40 and 60° C.) and forced air, the feasibility of convective drying of nano-drug particle laden strip-films formed from water-soluble polymeric film formers was demonstrated. Films can be dried in about 70 min even at the gentlest drying condition, and within 30 to 45 min at all other conditions; in contrast to oven drying that takes over 12 h. Although drying rates were a strong function of drying conditions, they were not significantly dependent on the precursor composition, viscosity or the absence or presence of drug particles. Typical adverse impacts of faster drying such as skin or ripple formation were absent, and films exhibited good appearance and uniformly good mechanical properties. Thermo-gravimetric analysis revealed that irrespective of drying intensity the water content in these films is fairly low at about 5 wt % resulting in the uniform level of drying for all types of films, thus also leading to uniformity in mechanical properties.

The nanoparticles were fully recovered upon re-dispersion in water from all convection-dried films, suggesting that the film formation process, including faster drying, does not lead to irreversible drug nanoparticle agglomeration. The powder XRD results showed that both the drug's degree of crystallinity and crystal form were retained during the film formation process. Dissolution tests conducted in the USP IV apparatus showed that drug was released from films within 20 minutes and the convective drying conditions did not significantly influence the dissolution response. Thus these films can be used as an immediate release form for poorly water-soluble drugs.

Detailed drug distribution evaluation done via Near-IR based chemical imaging showed that GF particles were fairly well-distributed, indicated by very low std values of drug amount in tens of thousands samples of about 131 µm diameter. The results also showed that the film-precursor viscosity had the strongest influence; higher viscosity exhibited better drug uniformity. Complimentary content uniformity analysis done via film assay showed that the RSD values were at about 6% or lower, and even below 3% for higher viscosity precursors. Lower RSD values for films made from higher viscosity film precursors corroborated the results from Near-IR chemical imaging. When the RSD values were corrected for the film thickness variation, it was found that all RSD values were under 2%; suggesting that thickness control may be employed in a high performance manufacturing process.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A method for fabricating a pharmaceutical product, comprising:
   providing an aqueous film forming precursor composition that includes one or more superdisintegrants;
   providing active agent nano-particles;
   mixing the aqueous film forming precursor composition and the one or more superdisintegrants with the active agent nano-particles to form a mixture, the mixture formed prior to formation of a stripfilm fabricated from the mixture, the mixture of the aqueous film forming precursor composition and the active agent nano-particles having a viscosity of from about 100 cP to about 25,000 cP; and drying and fabricating the mixture to form the stripfilm fabricated from the mixture;

wherein the mixture is dried at about 0° C. to about 80° C. for about 10 minutes to about 90 minutes to form the stripfilm.

2. The method of claim 1, wherein the film forming precursor composition includes one or more water-soluble polymers, or one or more water-insoluble polymers;

wherein the active agent nano-particles include one or more pharmaceutical active agent nano-particles;

wherein the active agent nano-particles include one or more poorly water-soluble drug nano-particles; and wherein the mixture is a suspension of the aqueous film forming precursor composition and the active agent nano-particles.

3. The method of claim 1, wherein the active agent nanoparticles include one or more nano-particles that are soluble in the mixture.

4. The method of claim 1, wherein the drying step includes convective drying in laminar flow conditions to form the stripfilm.

5. The method of claim 1, wherein the drying step includes drying the mixture at about 20% relative humidity to about 90% relative humidity.

6. The method of claim 1, wherein the step of providing the active agent nano-particles includes preparing a suspension of the active agent nano-particles by utilizing a top down approach or a bottom up approach.

7. The method of claim 1, wherein the active agent nano-particles are distributed uniformly within an interior of the stripfilm; and wherein about 80% or more of the active agent nano-particles from the dried stripfilm dissolve within thirty minutes in an in vitro dissolution test.

8. The method of claim 1, wherein the step of providing the active agent nano-particles includes preparing a suspension of the active agent nano-particles by an emulsion step.

9. The method of claim 1, wherein the step of providing the active agent nano-particles includes providing the active agent nano-particles in dry powder form; and wherein the active agent nano-particles are surface modified with one or more hydrophilic substances.

10. The method of claim 1, wherein the stripfilm has an active agent nano-particle loading of from about 0.01 weight % to about 50 weight %.

11. The method of claim 1, wherein the active agent nano-particles are in crystalline or amorphous form or combinations thereof;

wherein the film forming precursor composition includes one or more viscosity enhancers or disintegrants; and wherein the stripfilm is formed by casting the mixture onto a substrate.

12. The method of claim 1, wherein the stripfilm has an active agent nano-particle loading uniformity throughout an interior of the stripfilm, the active agent nano-particle loading uniformity varying in uniformity of active agent loading by less than 6% relative standard deviation over average active agent nano-particle mass per unit area of the stripfilm.

13. The method of claim 1, wherein the stripfilm has an active agent nano-particle loading uniformity throughout an interior of the stripfilm, the active agent nano-particle loading uniformity varying in uniformity of active agent loading by less than 3% relative standard deviation over average active agent nano-particle mass per unit area of the stripfilm; and wherein the fabricated stripfilm has a water content of from about 5 weight % to about 8 weight %.

14. The method of claim 1, wherein the mixing step includes mixing the aqueous film forming precursor composition and the active agent nano-particles with a vibratory or planetary mixer.

15. The method of claim 1, wherein the mixture of the aqueous film forming precursor composition and the active agent nano-particles has a viscosity of from about 4,000 cP to about 25,000 cP;

wherein due to a high swelling capacity of the one or more superdisintegrants, their addition to the aqueous film forming precursor composition raises the viscosity of the mixture.

16. The method of claim 1, wherein the stripfilm has an active agent nano-particle loading of from about 0.50 weight % to about 30 weight %; and wherein the content uniformity of the active agent nano-particles in the stripfilm indicated by the relative standard deviation of the active agent nano-particle content in the stripfilm is less than about 6%.

17. The method of claim 1, further comprising the step of re-dispersing the fabricated stripfilm in a medium to form a re-dispersion, the re-dispersing step including re-dispersing about a 0.7 cm$^2$ circular area of the stripfilm: (i) in about three ml to about 10 ml of water via vortex mixing for about one minute to about five minutes, or (ii) in about 15 ml of water via magnetic stirring for about 10 minutes;

wherein the active agent particles, prior to mixing with the aqueous film forming precursor composition, have a first D50 particle size distribution value and the re-dispersion of the fabricated stripfilm in the medium has a second D50 particle size distribution value, the first and second D50 particle size distribution values varying from one another by about 20% or less.

18. The method of claim 1, wherein the active agent nano-particles are about 5 nm to about 20,000 nm in size.

19. The method of claim 18, wherein the active agent nano-particles are about 30 nm to about 5,000 nm in size.

20. The method of claim 18, wherein the active agent nano-particles are about 50 nm to about 5,000 nm in size.

21. The method of claim 18, wherein the active agent nano-particles are about 50 nm to about 300 nm in size.

22. The method of claim 1, further comprising the step of re-dispersing the fabricated stripfilm in a medium to form a re-dispersion.

23. The method of claim 1, wherein due to a high swelling capacity of the one or more superdisintegrants, their addition to the aqueous film forming precursor composition increases stabilization of the mixture, aids in heterogenous uniformity of mixing of the active agent non-particles in a non-aggregated state, and contributes with re-dispersion and full-fast dissolution of the mixture.

24. A method for fabricating a pharmaceutical product comprising:

providing a film forming precursor composition that includes one or more superdisintegrants;

providing active agent nano-particles;

mixing the aqueous film forming precursor composition and the one or more superdisintegrants with the active agent nano-particles to form a mixture, the mixture formed prior to formation of a stripfilm fabricated from the mixture, the mixture having a viscosity of from about 4,000 cP to about 25,000 cP, wherein due to the high swelling capacity of the one or more superdisintegrants, their addition to the aqueous film forming precursor composition raises the viscosity of the mixture; and drying and fabricating the mixture to form the stripfilm fabricated from the mixture;

wherein the mixture is dried at about 0° C. to about 80° C. and at about 20% relative humidity to about 90% relative humidity for about 10 minutes to about 90 minutes to form the stripfilm;

wherein the film forming precursor composition includes one or more water-soluble polymers, or one or more water-insoluble polymers;

wherein the active agent nano-particles include one or more pharmaceutical active agent nano-particles; and wherein the stripfilm has an active agent nano-particle loading of from about 0.01 weight % to about 50 weight %.

25. The method of claim 24, wherein the stripfilm has an active agent nano-particle loading uniformity throughout an interior of the stripfilm, the active agent nano-particle loading uniformity varying in uniformity of active agent loading by less than 6% relative standard deviation over average active agent nano-particle mass per unit area of the stripfilm; and wherein the fabricated stripfilm has a water content of from about 5 weight % to about 8 weight %.

26. The method of claim 24, further comprising the step of re-dispersing the fabricated stripfilm in a medium to form a re-dispersion, the re-dispersing step including re-dispersing about a 0.7 cm$^2$ circular area of the stripfilm: (i) in about three ml to about 10 ml of water via vortex mixing for about one minute to about five minutes, or (ii) in about 15 ml of water via magnetic stirring for about 10 minutes;

wherein the active agent particles, prior to mixing with the aqueous film forming precursor composition, have a first D50 particle size distribution value and the re-dispersion of the fabricated stripfilm in the medium has a second D50 particle size distribution value, the first and second D50 particle size distribution values varying from one another by about 20% or less.

27. The method of claim 24, wherein the active agent nano-particles are distributed uniformly within an interior of the stripfilm; and wherein about 80% or more of the active agent nano-particles from the dried stripfilm dissolve within thirty minutes in an in vitro dissolution test.

28. The method of claim 24, further comprising the step of re-dispersing the fabricated stripfilm in a medium to form a re-dispersion.

29. A method for fabricating a pharmaceutical product comprising:

providing a film forming precursor composition and active agent particles;

mixing the aqueous film forming precursor composition with the active agent particles to form a mixture, the mixture formed prior to formation of a stripfilm fabricated from the mixture, the mixture having a viscosity of at least 6,000 cP;

re-dispersing the fabricated stripfilm in a medium to form a re-dispersion; and drying and casting the mixture to form the stripfilm fabricated from the mixture;

wherein the mixture is dried at about 0° C. to about 80° C. and at about 30% relative humidity to about 70% relative humidity for about 15 minutes to about 45 minutes to form the stripfilm;

wherein the film forming precursor composition includes one or more water-soluble polymers, or one or more water-insoluble polymers;

wherein the active agent particles include one or more active agent micro-particles, or one or more active agent nano-particles;

wherein the active agent particles include one or more BCS Class II or IV poorly water-soluble drug particles;

wherein the mixture is a suspension of the aqueous film forming precursor composition and the active agent particles;

wherein the drying step includes convective drying in laminar flow conditions to form the stripfilm;

wherein the stripfilm has an active agent particle loading of from about 0.50 weight % to about 30 weight %;

wherein the stripfilm is formed by casting the mixture onto a substrate;

wherein the stripfilm has an active agent particle loading uniformity throughout an interior of the stripfilm, the active agent particle loading uniformity varying in uniformity of active agent loading by less than 6% relative standard deviation over average active agent particle mass per unit area of the stripfilm; and wherein the fabricated stripfilm has a water content of from about 5 weight % to about 8 weight %.

30. The method of claim 29, wherein the re-dispersing step includes re-dispersing about a 0.7 cm$^2$ circular area of the stripfilm: (i) in about three ml to about 10 ml of water via vortex mixing for about one minute to about five minutes, or (ii) in about 15 ml of water via magnetic stirring for about 10 minutes;

wherein the active agent particles, prior to mixing with the aqueous film forming precursor composition, have a first D50 particle size distribution value and the re-dispersion of the fabricated stripfilm in the medium has a second D50 particle size distribution value, the first and second D50 particle size distribution values varying from one another by about 20% or less.

31. The method of claim 29, wherein the active agent nano-particles are distributed uniformly within an interior of the stripfilm; and wherein about 80% or more of the active agent nano-particles from the dried stripfilm dissolve within thirty minutes in an in vitro dissolution test.

32. A method for fabricating a pharmaceutical product, comprising:

providing an aqueous film forming precursor composition;

providing active agent particles;

mixing the aqueous film forming precursor composition with the active agent particles to form a mixture, the mixture formed prior to formation of a stripfilm fabricated from the mixture, the mixture of the aqueous film forming precursor composition and the active agent particles having a viscosity of from about 100 cP to about 25,000 cP;

re-dispersing the fabricated stripfilm in a medium to form a re-dispersion; and drying and fabricating the mixture to form the stripfilm fabricated from the mixture;

wherein the mixture is dried at about 0° C. to about 80° C. for about 10 minutes to about 90 minutes to form the stripfilm.

33. A method for fabricating a pharmaceutical product, comprising:

providing a film forming precursor composition that includes one or more superdisintegrants;

providing active agent particles;

mixing the aqueous film forming precursor composition and the one or more superdisintegrants with the active agent particles to form a mixture, the mixture formed prior to formation of a stripfilm fabricated from the mixture, the mixture having a viscosity of from about 4,000 cP to about 25,000 cP, wherein due to the high swelling capacity of the one or more superdisintegrants, their addition to the aqueous film forming precursor composition raises the viscosity of the mixture;

re-dispersing the fabricated stripfilm in a medium to form a re-dispersion; and drying and fabricating the mixture to form the stripfilm fabricated from the mixture;

wherein the mixture is dried at about 0° C. to about 80° C. and at about 20% relative humidity to about 90% relative humidity for about 10 minutes to about 90 minutes to form the stripfilm;

wherein the film forming precursor composition includes one or more water-soluble polymers, or one or more water-insoluble polymers;

wherein the active agent particles include one or more pharmaceutical active agent particles; and wherein the stripfilm has an active agent particle loading of from about 0.01 weight % to about 50 weight %.

* * * * *

UNITED STATES PATENT AND TRADEMARK OFFICE
CERTIFICATE OF CORRECTION

| | |
|---|---|
| PATENT NO. | : 10,646,452 B2 |
| APPLICATION NO. | : 14/777191 |
| DATED | : May 12, 2020 |
| INVENTOR(S) | : Rajesh N. Dave et al. |

It is certified that error appears in the above-identified patent and that said Letters Patent is hereby corrected as shown below:

In the Specification

At Column 1, Line 18 delete:
"The research leading to the present disclosure was supported in part by federal grants, including the NSF Grant #EEC-0540855. Accordingly, the United States Government may have certain rights in the disclosure."

Insert:
--This invention was made with government support under Grant number 0540855 awarded by the National Science Foundation. The government has certain rights in the invention.--

Signed and Sealed this
Thirty-first Day of January, 2023

Katherine Kelly Vidal
*Director of the United States Patent and Trademark Office*